(12) United States Patent
Kusaka et al.

(10) Patent No.: US 10,907,012 B2
(45) Date of Patent: Feb. 2, 2021

(54) POLYCARBONATE DIOL AND PRODUCING METHOD THEREOF, AND POLYURETHANE AND ACTIVE ENERGY RAY-CURABLE POLYMER COMPOSITION BOTH FORMED USING SAME

(71) Applicant: MITSUBISHI CHEMICAL CORPORATION, Chiyoda-ku (JP)

(72) Inventors: Haruhiko Kusaka, Yokohama (JP); Kazuki Wakabayashi, Yokohama (JP); Masanori Yamamoto, Kitakyushu (JP); Kazunao Kusano, Kitakyushu (JP); Hiroto Ito, Yokkaichi (JP); Takashi Komaya, Chiyoda-ku (JP); Teruhiko Ohara, Chiyoda-ku (JP); Kentaro Uchino, Yokkaichi (JP); Haruo Iiduka, Yokkaichi (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 9 days.

(21) Appl. No.: 13/652,070

(22) Filed: Oct. 15, 2012

(65) Prior Publication Data
US 2013/0109804 A1   May 2, 2013

Related U.S. Application Data

(63) Continuation of application No. PCT/JP2011/059206, filed on Apr. 13, 2011.

(30) Foreign Application Priority Data

Apr. 14, 2010 (JP) ................................. 2010-093155
Aug. 30, 2010 (JP) ................................. 2010-191858

(51) Int. Cl.
| | | |
|---|---|---|
| C08G 64/16 | (2006.01) |
| C08G 18/44 | (2006.01) |
| C08G 18/67 | (2006.01) |
| C09J 175/04 | (2006.01) |
| C09D 175/04 | (2006.01) |
| C09D 175/16 | (2006.01) |
| C08G 18/75 | (2006.01) |
| C09D 175/14 | (2006.01) |
| C08G 18/66 | (2006.01) |
| C08G 64/02 | (2006.01) |

(Continued)

(52) U.S. Cl.
CPC .......... *C08G 64/1608* (2013.01); *B32B 27/40* (2013.01); *C07D 493/04* (2013.01); *C08F 20/36* (2013.01); *C08F 290/067* (2013.01); *C08G 18/44* (2013.01); *C08G 18/664* (2013.01); *C08G 18/672* (2013.01); *C08G 18/755* (2013.01); *C08G 64/02* (2013.01); *C08G 64/0208* (2013.01); *C08G 64/302* (2013.01); *C08G 64/305* (2013.01); *C08L 75/04* (2013.01); *C09D 175/04* (2013.01); *C09D 175/14* (2013.01); *C09D 175/16* (2013.01); *C09J 175/04* (2013.01); *C09J 175/14* (2013.01)

(58) Field of Classification Search
CPC .... C08G 64/00; C08G 64/0208; C08G 64/20; C08G 64/302; C08G 64/305; C08G 64/1608; C08G 18/44; C08G 18/664; C08G 18/672; C08G 18/755; C08G 64/02; C08F 290/067; C08F 20/36; C09D 175/04; C09D 175/14; C09D 175/16; C09J 175/04; C07D 493/04; B32B 27/40; C08L 75/04
USPC .................................................. 528/370, 371
See application file for complete search history.

(56) References Cited

U.S. PATENT DOCUMENTS

| | | | | |
|---|---|---|---|---|
| 4,605,681 A | * | 8/1986 | Grey .................. | C08G 18/2805 521/159 |
| 6,548,623 B2 | * | 4/2003 | Brunelle ................ | C08G 64/04 528/196 |

(Continued)

FOREIGN PATENT DOCUMENTS

| | | |
|---|---|---|
| CN | 101120034 A | 2/2008 |
| CN | 101155852 A | 4/2008 |

(Continued)

OTHER PUBLICATIONS

Machine English translation of JP 2008-024919, Fuji et al., Feb. 2008.*
Odian, G., "Principles of Polymerization", Third Edition, 1991, pp. 19-33.*
Katsuji Matsunaga, "Polyurethane No Kiso to Ouyou", CMC Publishing Co., Ltd., Nov. 2006, pp. 96-107 plus cover page.

(Continued)

*Primary Examiner* — Patrick D Niland
(74) *Attorney, Agent, or Firm* — Oblon, McClelland, Maier & Neustadt, L.L.P.

(57) ABSTRACT

A novel polycarbonate diol is useful as a raw material for producing a polycarbonate diol-based polyurethane with a high degree of hardness, superior abrasion resistance, and superior hydrophilicity. The polyurethane is useful in paints, coating agents, synthetic leathers, artificial leathers, and highly-functional elastomers, or the like. The polycarbonate diol is also useful for producing an active-energy radiation curable polymer composition giving a cured film having superior contamination resistance and high degree of hardness. The curable polymer composition contains a urethane (meth)acrylate oligomer obtained from the polycarbonate diol. The polycarbonate diol is obtained, for example, by reacting two specific types of diols with diester carbonate in the presence of a transesterification catalyst. The catalyst has a metal of Group 1 or 2 on the periodic table. A metal content of the transesterification catalyst is 100 weight ppm or less.

18 Claims, No Drawings

(51) Int. Cl.
*C08F 290/06* (2006.01)
*C07D 493/04* (2006.01)
*C08G 64/30* (2006.01)
*B32B 27/40* (2006.01)
*C09J 175/14* (2006.01)
*C08L 75/04* (2006.01)
*C08F 20/36* (2006.01)

(56) References Cited

U.S. PATENT DOCUMENTS

| | | |
|---|---|---|
| 2004/0241553 A1 | 12/2004 | Abe et al. |
| 2006/0149024 A1* | 7/2006 | Ono et al. .................... 528/196 |
| 2009/0023823 A1* | 1/2009 | Kim .................. C08G 18/4018 521/48.5 |
| 2009/0105393 A1* | 4/2009 | Jansen .................. C08G 63/64 524/502 |
| 2010/0048854 A1 | 2/2010 | Miyake et al. |
| 2010/0190953 A1 | 7/2010 | Fuji et al. |
| 2011/0034616 A1 | 2/2011 | Noordover et al. |
| 2011/0092643 A1 | 4/2011 | Frijns et al. |
| 2011/0257362 A1 | 10/2011 | Fuji et al. |

FOREIGN PATENT DOCUMENTS

| | | | |
|---|---|---|---|
| CN | 101448871 A | 6/2009 | |
| EP | 2 036 937 A1 | 3/2009 | |
| EP | 2036937 A1 * | 3/2009 | ............. C08G 18/44 |
| EP | 2 112 187 A1 | 10/2009 | |
| JP | 55-56124 A | 4/1980 | |
| JP | 2000-95854 A | 4/2000 | |
| JP | 2002-69166 A | 3/2002 | |
| JP | 2003-292603 A | 10/2003 | |
| JP | 2004-247274 A | 9/2004 | |
| JP | 2008-024919 * | 2/2008 | |
| JP | 2008-56844 A | 3/2008 | |
| JP | 2009-63976 A | 3/2009 | |
| JP | 2009-161745 A | 7/2009 | |
| JP | 2009-167296 A | 7/2009 | |
| JP | 2009-227915 A | 10/2009 | |
| TW | 200951154 A1 | 12/2009 | |
| WO | WO 2004/111106 A1 | 12/2004 | |
| WO | WO 2008/029746 A1 | 3/2008 | |
| WO | WO 2008/069725 * | 6/2008 | |
| WO | WO 2008/069725 A1 | 6/2008 | |
| WO | WO 2008/093860 A1 | 8/2008 | |
| WO | WO 2009/033934 A1 | 3/2009 | |
| WO | WO 2009/057609 A | 5/2009 | |

OTHER PUBLICATIONS

Makito Yokoe, et al., "Biodegradable Polymers Based on Renewable Resources. VII. Novel Random and Alternating Copolycarbonates from 1,4:3,6-Dianhydrohexitols and Aliphatic Diols", Journal of Polymer Science: Part A: Polymer Chemistry, vol. 41, 2003, pp. 2312-2321.
Combined Chinese Office Action and Search Report dated Dec. 19, 2013 in Patent Application No. 201180019088.6 (with English language translation).
Office Action dated Oct. 20, 2014 in Chinese Patent Application No. 201180019088.6 (with English language translation).
Office Action dated Apr. 30, 2015 in Chinese Patent Application No. 201180019088.6 (with English translation).
Extended European Search Report dated Oct. 29, 2015 in Patent Application No. 11768898.6.
Taiwanese Office Action dated May 5, 2015 in Patent Application No. 100113101 (with English Translation).
Office Action dated Feb. 7, 2017, in corresponding European Patent Application No. 11768898.6.
Combined Office Action and Search Report dated Nov. 28, 2017 in Chinese Patent Application No. 201610023560.8 (with English translation).
Korean Office Action dated May 23, 2017 in Patent Application No. 10-2012-7027712 (with English translation).
Second Office Action dated Oct. 24, 2018, in corresponding Chinese Patent Application No. 201610023560.8 with English translation retrieved by Global Dossier.
Extended European Search Report dated Feb. 1, 2019 in Patent Application No. 18192402.8, 7 pages.

* cited by examiner

POLYCARBONATE DIOL AND PRODUCING METHOD THEREOF, AND POLYURETHANE AND ACTIVE ENERGY RAY-CURABLE POLYMER COMPOSITION BOTH FORMED USING SAME

CROSS REFERENCE TO RELATED APPLICATION

This application is a continuation application of PCT/JP2011/059206, filed on Apr. 13, 2011, and claims priority to Japanese Patent Application No. 2010-095155, filed on Apr. 14, 2010, and Japanese Patent Application No. 2010-191858, filed on Aug. 30, 3010.

BACKGROUND OF THE INVENTION

Field of the Invention

The present invention relates to a novel polycarbonate diol. This invention further relates to a polycarbonate-type polyurethane, which is made of this polycarbonate diol and which is useful for various applications such as paints, coating agents, synthetic/artificial leathers, and highly-functional elastomer, etc. with excellent balance of physical properties.

This invention further relates to an active-energy radiation curable polymer composition containing an urethane(meth) acrylate oligomer, a cured film obtained by irradiating the active energy ray to the composition, and a laminated product using the same.

Description of the Related Art

Conventional raw materials of a soft segment part of an industrial scale-produced polyurethane resin are mainly classified into an ether type typified by polytetramethyleneglycol, an ester type typified by adipate-based ester, polylactone type typified by polycaprolactone and polycarbonate type typified by polycarbonate diol (Katsuji Matsunaga (editor) "POLYURETHANE NO KISO TO OUYOU" CMC Publishing CO., LTD., November 2006, pp. 96-106.).

Among them, the ether type is excellent in hydrolysis resistance, flexibility and stretching properties, while is said to be inferior in heat resistance and light resistance. On the other hand, the ester type has better heat resistance and weather resistance, while its ester part is inferior in hydrolysis resistance and can not be used in some applications. On the other hand, the polylactone type is regarded as a more excellent grade in hydrolysis resistance when relative to the ester type, while it also contains an ester group therefore the complete control of hydrolysis suppression is impossible. An application of combining the ester type, the ether type and the polylactone type is proposed, however any conventional method cannot fully complement those weakness.

On the other hand, the polycarbonate-type polyurethane using a polycarbonate diol is recognized as the best quality durable grade in terms of heat resistance and hydrolysis resistance, which is widely used as a durable film, an artificial leather for cars and furnitures, a coating material (especially an water-based coating material), a coating agent, and an adhesive agent.

However, a polycarbonate diol being commercially and broadly available is mainly a polycarbonate diol that be synthesized from a 1,6-hexanediol, and the polyurethane produced with said polycarbonate diol has a defect in which it is flexible because of a chained soft segment part and its surface is easily bruised physically. Therefore, when the obtained polyurethane is used as a painting material or a coating agent, it may be easily bruised due to physical factors and result in an inferior appearance.

In order to solve these problems, as a polycarbonate diol which can provide a polyurethane with higher rigidity, a polycarbonate diol obtained from 1,4-cyclohexanedimethanol (Japanese laid open Sho-55-56124 A) as well as a polycarbonate diol obtained from 1,4-cyclohexanedimethanol and a 1,6-hexanediol (Japanese laid open 2002-69166 A) are proposed.

However, the 1,4-cyclohexanedimethanol is a mixture of a cis-isomer and a trans-isomer due to its producing limitation, and when its mixture ratio is changed, physical properties of the polycarbonate diol itself being synthesized and the polyurethane to be induced will change, therefore its quality control becomes difficult. In addition, a polycarbonate diol, that is obtained by combining the 1,4-cyclohexane dimethanol and the 1,6-hexanediol, exhibits higher hydrophobic property due to its structure, so when water-based polyurethane, which has been known these days in terms of reduction in environmental burden, is produced, the hydrophilic structure must be introduced in producing a polyurethane in order to render the polyurethane water-soluble. As a result, this has been a constraint on polyurethane designing.

The 1,4-cyclohexane dimethanol also has a cyclohexane ring in a molecule as a ring structure, while the cyclohexane dimethanol is a flexible ring structure and its hydroxyl is bound to the cyclohexane dimethanol via a methylene group, so its molecular structure is not very rigid and it was not enough in terms of the polyurethane hardness to be obtained. Furthermore, the 1,4-cyclohexane dimethanol is derived from a fossil source, and burning a polymer substance made of this may cause a problem which could promote global warming.

Consequently, the development of a polycarbonate diol, which can be easily produced without those limitations, of which environmental burden is small, and which exhibits rigid and scratch resistant characteristic when a polyurethane is made thereof, has been expected.

On the other hand, isosorbide is a plant-derived diol which is obtained by cyclodehydrating a sorbitol which is a natural sugar, and is still a compound with small environmental burden even after it is burnt. Therefore, its application has been greatly considered these days as a monomer source for obtaining a polycarbonate with smaller effect on global warming (WO 08/029,746, for example). According to this WO 08/029,746, a copolymerized polycarbonate can be produced from a diol mixture containing the isosorbide, which could produce a polycarbonate having both handling property and rigid physical property together.

However as a matter of course, a large number of known documents related to producing a polycarbonate from the isosorbide all aim to obtain a high-molecular weight polycarbonate. Further these documents do not describe any isolation approach with high purity of polycarbonate having smaller molecular weight and a hydroxyl structure at both ends thereof, and do not describe using isosorbide as a polyol material for producing a polyurethane, either.

On the other hand, coating by paint is a common practice with an aim for protecting the surface of base material and for maintaining its appearance. For these paints, a paint material cured by an energy ray irradiation is developed and has been in practical use in terms of higher productivity and better working environments, etc.

As a paint material like this, known is an energy ray curable polymer composition containing an urethane acrylate which is obtained by reaction of an organic polyisocyanate, a polycarbonate polyol having an alicyclic structure, a (meth)acrylate having one or more hydroxyl(s) in a molecule, for example (Japanese laid open 2009-227915A). A paint material like this is required various kinds of characteristics according to applications.

SUMMARY OF THE INVENTION

The first problem of the present invention is to develop a polyurethane which is rigid, is not physically easily bruised, and has no designing limitation for introducing a hydrosoluble structure in producing a polyurethane, and is consequently to design and produce a polycarbonate diol raw material which can exhibit those characteristics for this purpose. In particular, the second problem is to design and produce a polycarbonate diol raw material to obtain a homogeneous polyurethane. In addition, the third problem is to design and produce a polycarbonate diol raw material to obtain a polyurethane having the characteristics being designed.

The forth problem of the present invention is to establish a method for producing the polycarbonate diol and polyurethane on an industrial scale.

Furthermore, the fifth problem of the present invention is to provide an active-energy radiation curable polymer composition giving a cured film having an excellent contamination resistance and high degree of hardness. In particular, the sixth problem is to provide an active-energy radiation curable polymer composition excellent in coating properties.

The inventors of the present invention devoted themselves to researches to solve the above first, second and forth problems, found that the above first, second and forth problems can be solved by a polycarbonate diol which is obtained by reacting a specific compound under the presense of a catalyst, and which has a certain amount of the aforementioned catalyst, and a polyurethane which is produced by using this polycarbonate diol, and reached the present invention.

The inventors of the present invention devoted themselves to researches to solve the above first, third and forth problems, found that the above first, third and forth problems can be solved by a polycarbonate diol, which has a specific repeating unit in a molecular chain and which has the specific ratio of the aforementioned specific repeating unit ratio to the molecular chain terminals, and a polyurethane which is produced by using this polycarbonate diol, and reached the present invention.

The inventors of the present invention devoted themselves to consideration to solve the aforementioned 5 and 6 problems, found that an active-energy radiation curable polymer composition containing an urethane(meth)acrylate oligomer which is obtained from a raw material containing a polycarbonate diol, in which the average number of hydroxyl groups of the aforementioned polycarbonate diol per one molecule is specified to a predetermined amount, could result in better coating properties. Further the inventors of the present invention found that when a cured film is obtained by curing this, its contamination resistance and degree of hardness are more particularly excellent than a conventional one, and reached the present invention.

Therefore, the first aspect of the present invention consists in the following [1] to [33].
[1] A polycarbonate diol being obtained by reacting (i) at least one of diols selected from isosorbide, isomannide and isoidide, (ii) a diol having 1 to 15 carbons which may contain hetero atom, and (iii) a diester carbonate, by use of a transesterification catalyst,
in which the transesterification catalyst is either a compound using a metal of Group 1 or a compound using a metal of Group 2 on the periodic table and,
the amount of the transesterification catalyst contained in the polycarbonate diol is 100 ppm or less as the weight ratio of the metal.
[2] The polycarbonate diol according to [1], the amount of the transesterification catalyst contained in the polycarbonate diol is 0.1 ppm or more as the weight ratio of the metal.
[3] The polycarbonate diol according to [1] or [2], the transesterification catalyst is a compound using a metal of Group 2 on the periodic table.
[4] The polycarbonate diol according to any one of [1] to [3], in which at least part of a molecular chain includes a repeating unit represented by the following formula (A) and a repeating unit represented by the following formula (B) and,
the number average molecular weight is 250 or more and 5,000 or less, and
the terminal (A) ratio represented by the following formula (I) is 1.2 or more and 1.9 or less.

[Chemical formula 1]

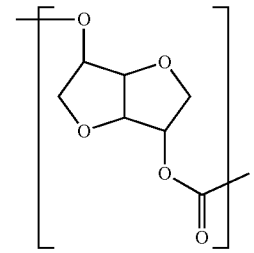
(A)

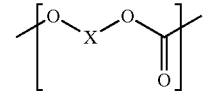
(B)

Terminal (A) ratio (I)={(The number of structure (A) in molecular chain terminal)/(The total number of structures (A) and (B) in molecular chain terminal)}/{(The number of structure (A) in molecular chain)/(The total number of structures (A) and (B) in molecular chain)}[Mathematical formula 1]

In formula (B), X represents a divalent group having 1 to 15 carbons which may contain hetero atom.
[5] The polycarbonate diol according to any one of [1] to [4], in which the highest temperature of the reaction is lower than 180° C.
[6] A polycarbonate diol, in which at least part of a molecular chain includes a repeating unit represented by the formula (A) and a repeating unit represented by the formula (B), while the number average molecular weight is 250 or more and 5,000 or less, and the terminal (A) ratio represented by the formula (I) is 1.2 or more and 1.9 or less.
[7] The polycarbonate diol according to [6], in which the number average molecular weight is 500 or more and 5,000 or less.
[8] The polycarbonate diol according to [6] or [7], being obtained by reacting (i) at least one of diols selected from isosorbide, isomannide and isoidide, (ii) a diol having 1 to 15 carbons which may contain hetero atom, and (iii) a diester carbonate, by use of a transesterification catalyst.

[9] The polycarbonate diol according to [8], in which the transesterification catalyst is a compound using a metal of Group 1 or metal of Group 2 on the periodic table.

[10] The polycarbonate diol according to [9], in which the transesterification catalyst is a compound using a metal of Group 2 on the periodic table.

[11] The polycarbonate diol according to any one of [8] to [10], in which the highest temperature of the reaction is lower than 180° C.

[12] A polycarbonate diol producing method, comprising;
reacting (i) at least one of diols selected from isosorbide, isomannide and isoidide, (ii) a diol having 1 to 15 carbons which may contain hetero atom, and (iii) a diester carbonate, by use of a transesterification catalyst, and
in which the highest temperature during the reaction is lower than 180° C.

[13] The polycarbonate diol producing method according to [12], in which the transesterification catalyst is a compound using a metal of Group 1 or metal of Group 2 on the periodic table.

[14] The polycarbonate diol producing method according to [13], the transesterification catalyst is a compound using a metal of Group 2 on the periodic table.

[15] The polycarbonate diol obtained by the polycarbonate diol producing method according to any one of [12] to [14].

[16] The polycarbonate diol according to any one of [1] to [5], [8] to [11], and [15], in which the diester carbonate is a diphenyl carbonate.

[17] The polycarbonate diol according to any one of [1] to [5], [8] to [11], [15] and [16], in which the content of the diphenyl carbonate is 1 weight % or less.

[18] The polycarbonate diol according to any one of [1] to [5], [8] to [11], and [15] to [17], in which the diol of the aforementioned (i) contains 20 ppm or less of formic acid.

[19] The polycarbonate diol according to any one of [1] to [5], [8] to [11], and [15] to [18], in which 5% or less of molecular chain terminals are either an alkyloxy group or an aryloxy group among all terminals of the molecular chains.

[20] The polycarbonate diol according to any one of [1] to [11], and [15] to [19], in which the value of Hazen color number (APHA value: according to JIS K0071-1) is 100 or less.

[21] The polycarbonate diol according to any one of [1] to [11] and [15] to [20], in which the molecular weight distribution is 1.5 to 3.5.

[22] A polyurethane obtained by using the polycarbonate diol according to any one of [1] to [11] and [15] to [21].

[23] The polyurethane according to [22], in which by using a strip as a sample of the polyurethane having 10 mm in width, 100 mm in length, and about 50 to 100 μm in thickness, a tensile elongation at break thereof is 400% or less measured under conditions of the distance between chucks of 50 mm, a tensile speed of 500 mm/min., a temperature of 23° C. and a relative humidity of 55%.

[24] The polyurethane according to [22] or [23], in which by using a strip as a sample of the polyurethane having 10 mm in width, 100 nm in length, and about 50 to 100 μm in thickness, a 100% modulus is 10 MPa or more measured under conditions of the distance between chucks of 50 mm, a tensile speed of 500 mm/min., a temperature of 23° C. and a relative humidity of 55%.

[25] The polyurethane according to any one of [22] to [24], in which by using a film-like sample of the polyurethane having about 50-100 μm in thickness, a weight reduction ratio is 2% or less at friction testing with 4.9 N (500 reciprocations) according to JIS L0849.

[26] A polyurethane producing method, comprising; reacting the polycarbonate diol according to any one of [1] to [11] and [15] to [21] and a polyisocyanate thereby obtaining a prepolymer, and reacting the prelolymer with a chain extender.

[27] A polyurethane producing method, comprising; mixing the polycarbonate diol according to any one of [1] to [11] and [15] to [21], a polyisocyanate, and a chain extender at one time, followed by reacting them.

[28] A paint material or a coating agent produced by using the polyurethane according to any one of [22] to [25].

[29] An artificial leather or a synthetic leather produced by using the polyurethane according to any one of [22] to [25].

[30] A water-based polyurethane paint material produced by using the polyurethane according to any one of [22] to [25].

[31] A medical material produced by using the polyurethane according to any one of [22] to [25].

[32] An adhesive produced by using the polyurethane according to any one of [22] to [25].

[33] An active-energy radiation curable polymer composition containing an urethane(meth)acrylate oligomer obtained from a raw material containing the polycarbonate diol according to any one of [1] to [11] and [15] to [21], polyisocyanate, and hydroxyalkyl(meth)acrylate.

The second aspect of the present invention consists in the following [34] to [44].

[34] An active-energy radiation curable polymer composition containing urethane(meth)acrylate oligomer obtained from a raw material containing polyisocyanate, polycarbonate diol and hydroxyalkyl(meth)acrylate,
in which the polycarbonate diol contains 10 mass % or more of repeating unit represented by the formula (A), the number average molecular weight of the polycarbonate diol is 500 or more and 5,000 or less, and the average number of hydroxyl groups of the polycarbonate diol per one molecule is 2.2 or less.

[35] The active-energy radiation curable polymer composition according to [34], the polycarbonate diol further contains repeating unit represented by the formula (B).

[36] The active-energy radiation curable polymer composition according to [35], X in the formula (B) represents a divalent group having 6 carbons.

[37] An active-energy radiation curable polymer composition containing urethane(meth)acrylate oligomer obtained from a raw material containing polyisocyanate, polycarbonate diol and hydroxyalkyl(meth)acrylate,
in which the polycarbonate diol is obtained by reacting (i) at least one of diols selected from isosorbide, isomannide and isoidide, (ii) diol having 1 to 15 carbons which may contain hetero atom, and (iii) diester carbonate, by use of a transesterification catalyst, and in which the number average molecular weight of the polycarbonate diol is 500 or more and 5,000 or less, and the average number of hydroxyl groups of the polycarbonate diol per one molecule is 2.2 or less.

[38] The active-energy radiation curable polymer composition according to [34] to [37], in which the number average molecular weight of the polycarbonate diol is 3,000 or less.

[39] The active-energy radiation curable polymer composition according to any one of [34] to [38], in which the calculated crosslinking points molecular weight is 500 to 10,000.

[40] The active-energy radiation curable polymer composition according to any one of [34] to [39], in which the raw material further contains a high-molecular weight polyol having number average molecular weight of over 500 excluding the polycarbonate diol.

[41] The active-energy radiation curable polymer composition according to any one of [34] to [40], in which the raw material further contains a low-molecular weight polyol having number average molecular weight of 500 or less excluding the polycarbonate diol.

[42] The active-energy radiation curable polymer composition according to any one of [34] to [41], in which the urethane(meth)acrylate oligomer has a structure obtained by an urethane reaction of an urethane prepolymer having isocyanate group at terminals and hydroxyalkyl(meth)acrylate, and in which the urethane prepolymer is obtained by an urethane reaction of the polyisocyanate and the polycarbonate diol.

[43] A cured film obtained by irradiating the active-energy ray to the active-energy radiation curable polymer composition according to any one of [34] to [42].

[44] A laminated body having layer comprised of the cured film according to [43] on a base material.

According to the first aspect of the present invention, a polyurethane produced by using a polycarbonate diol is more excellent in degree of hardness and friction-resistance, compared to a polyurethane made of polycarbonate diol derived from a conventionally used 1,6-hexanediol. Therefore the polyurethane is suited for such an application that resistance is required to physical external factors such as paints, coating agents, adhesive, etc., and this is quite industrially useful.

Also, an active-energy radiation curable polymer composition related to the second aspect of the present invention contains an urethane(meth)acrylate oligomer having a specific polycarbonate diol as mentioned above, and thus can form a cured film having an excellent contamination resistance and high degree of hardness.

DESCRIPTION OF THE EMBODIMENTS

Embodiment of the present invention is described in detail below, but the present invention is not limited to the following embodiments, but it can be applied by changing its form in various ways within the scope of the invention.

In the present description, (meth)acrylate refers to a collective term for acrylate and methacrylate, and the term means both of/either the acrylate and/or the methacrylate. This is true to (meth)acryloyl group and (meth)acrylic acid.

In the present description, "-" means including the values before and after the symbol as its lowest value and the highest value.

[Polycarbonate Diol]

A polycarbonate diol related to the first aspect of the present invention is preferred to be made of a diol and a diester carbonate, and produced by using a transesterification catalyst. The diol includes at least one of isosorbide, isomannide and isoidide which are stereoisomers of isosorbide, and isoidide as well as a diol having 1-15 carbons which may contain hetero atom. The diester carbonate includes alkyl carbonate, aryl carbonate, and alkylene carbonate, for example.

The transesterification catalyst includes a single metal generally recognized having transesterification of esters and a metallic compound such as a hydroxide or a salt of metal. Preferably, a catalyst including an acetate salt, a carbonate salt, and a hydroxide of a metal of Group 1 or 2 on the periodic table, and using a Group 2 metal on the periodic table is more preferred.

A catalyst used during producing may remain in a polycarbonate diol, and it may promote urethane reaction too much, so no catalyst being left is more preferred. Based on this viewpoint, the amount of catalyst left in the polycarbonate diol is preferably 100 weight ppm or less when converted into a catalyst metal. Any smaller value is preferred as the lower limit of the catalyst remained amount, but 0.1 weight ppm or more can be specified in terms of simplification of a producing method.

The polycarbonate diol related to the first aspect of the present invention is preferred to be a polycarbonate diol including a repeating unit represented by the following formula (A) in at least part of the molecular chain (hereinafter, a structure represented by the formula (A) may be indicated as "structure (A)"), and having number average molecular weight of 250 or more, or more preferably 500 or more and 5,000 or less.

[Chemical formula 2]

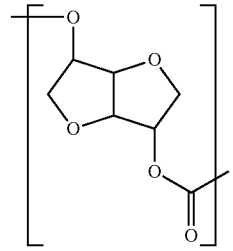

(A)

The polycarbonate diol related to the first aspect of the present invention is preferred to have the Structure (A) in at least part of the molecular chain, and may include other structures. Amount of the aforementioned other structure may be in the range which can exhibit an effect by those other structures in addition to the effect of the present invention, so it can be decided arbitrarily according to those other structures.

The aforementioned other structure may have a structure represented by the following formula (B) (hereinafter, a structure represented by the formula (B) may be referred to as "structure (B)"), for example:

[Chemical formula 3]

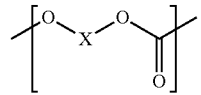

(B)

In formula (B), X represents a divalent group having 1 to 15 carbons which may contain hetero atom.

{Structural Feature}

The first structural feature of the Structure (A) related to the first aspect of the present invention is a less-flexible rigid structure with two condensed furan rings. Therefore in the polycarbonate diol related to the first aspect of the present invention, rigidity appears in this Structure (A) part. The second feature is an extremely rigid structure with less freedom in a binding portion of a carbonate group and the condensed furan rings as well, because the carbonate group is directly bound to the condensed furan rings without a freely rotatable group such as a methylene group therebetween. The third feature is higher hydrophilic property because two hydrophilic furan rings are placed with high-density and therefore affinity with a polar group such as water molecule is recognized.

The polycarbonate diol related to the first aspect of the present invention is preferred that the aforementioned 5% or less of molecular chain terminals are either an alkyloxy group or an aryloxy group among all terminals of the aforementioned molecular chains and is more preferred that the aforementioned 5% or less of molecular chain terminals are either an alkyloxy group or an aryloxy group among all terminals of the aforementioned molecular chains and further 95% or more is a hydroxyl group among both terminals of the molecular chain. In the structure, this hydroxyl group can react with a polyisocyanate during polyurethane forming reaction.

The structure (A) may be continuing in the aforementioned polycarbonate diol, may consist in regular intervals, or may be unevenly distributed. The content of the aforementioned Structure (A) in the aforementioned polycarbonate diol is 10 mass % or more, preferably 20 mass % or more, and further preferably 40 mass % or more in terms of rigidity, hydrophilic property, etc. Introducing a structure other than the structure (A) in the molecular chain decreases a melting point and viscosity and results in better handling property because of the poor regularity of polycarbonate diol in addition to effects brought by the previously described rigidity and hydrophilic property, etc. Therefore, in the first aspect of the present invention, any structure other than Structure (A) may be introduced to a polycarbonate diol in the range in which effect of the present invention can be obtained.

{Structure (B)}

X in formula (B) representing Structure (B) indicates a divalent group having 1 to 15 carbons which may contain hetero atom, and may include a straight or branched chain or ring group or any of these structures.

The carbon number of elements constituting X is preferably 10 or less, and more preferably 6 or less.

A hetero atom which may be included in X is oxygen atom, sulfur atom, nitrogen atom, etc., while oxygen atom is more preferred in terms of chemical stability.

A specific example of X group includes a group which is generated by using a compound exemplified as below as a Structure (B)—giving compound in producing a polycarbonate diol related to the first aspect of the present invention, while more preferred group includes a group obtained by reacting a preferred compound among the following exemplified compounds.

The Structure (B) may be continuing in the aforementioned polycarbonate diol, may consist in regular intervals, or may be unevenly distributed. The content of the aforementioned Structure (B) in the aforementioned polycarbonate diol is preferred to consist at 80 mass % or less in terms of poor polycarbonate diol regularity and better handling due to decreased melting point and viscosity, while 60 mass % or less is more preferred, 40 mass % or less is further preferred, and 20 mass % or less is specially preferred.

{Ratio of Structure (A) and Structure (B)}

The ratio of Structure (A) and Structure (B) constituting the polycarbonate diol-molecular chain related to the first aspect of the present invention (hereinafter, may be referred as "(A)/(B) ratio") is usually Structure (A)/Structure (B)=100/0 to 1/99 by mol ratio. Introducing Structure (B) into a molecular chain disarranges the polycarbonate diol regularity, lowers the melting point and viscosity, and therefore improves handling property. Effects of the present invention such as the aforementioned rigidity and hydrophilic property, etc. are mainly introduced by the Structure (A) part, so if the ratio of Structure (A) part is too small in the polycarbonate diol related to the first aspect of the present invention, its effects may not be enough. (A)/(B) ratio of 100/0 to 10/90 is preferred, 80/20 to 20/80 is more preferred, while 70/30 to 30/70 is further preferred.

In the polycarbonate diol related to the first aspect of the present invention, the ratio of Structure (A)/Structure (B) in the molecular chain terminals, which is ratio of a part forming the molecular chain terminals by combining the structured represented by formula (A) and hydrogen atom, or an alkyloxy group or an aryloxy group, and a part forming the molecular chain terminals by combining the structure represented by formula (B) and hydrogen atom, or an alkyloxy group or an aryloxy group (hereinafter, this ratio may be referred as "Terminal ratio of (A)/(B)"), is preferably 95/5 to 20/80, more preferably 90/10 to 30/70, and further preferably 80/20 to 40/60. In this molecular chain terminal, if Structure (B) part is larger than this range, designed features such as hardness may not be obtained.

The ratio of the molecular chain terminal's Structure (A) with the total number of the molecular chain terminal's Structure (A) and (B), as well as the ratio of Structure (A) in all molecular chains to the total number of Structure (A) and (B) in all molecular chains obtained by the following formula (I) (hereinafter, it may be referred as "Terminal (A) ratio (I)" is not specifically limited, but usually, 1.1 or more, preferably 1.2 or more, more preferably 1.3 or more, and specially preferably 1.4 or more, while is usually 5.0 or less, preferably 3.0 or less, more preferably 2.0 or less, further preferably 1.9 or less, and specially preferably 1.8 or less. When this terminal (A) ratio (I) exceeds the above upper limit, the urethane reaction speed becomes too fast and therefore designed physical property such as hardness may not be obtained, while it lowers the above lower limit, practically enough urethane reaction speed may not be obtained for industrial practice. The terminal (A) ratio (I) may be adjusted by the ratio of diol which is a raw material of Structure (A) and (B), types or amount of catalysts, and maximum temperature and times of reaction.

Terminal (A) ratio (I)={(The number of structure (A) in molecular chain terminal)/(The total number of structures (A) and (B) in molecular chain terminal)}/{(The number of structure (A) in molecular chain)/(The total number of structures (A) and (B) in molecular chain)[Mathematical formula 2]

{Raw Material Monomer}

The polycarbonate diol related to the first aspect of the present invention is, as discussed later, is made from raw materials of diol and diester carbonate.

[Diester Carbonate]

Available diester carbonate is not limited as long as an effect of the present invention is exhibited, but includes an alkyl carbonate, an aryl carbonate, or an alkylene carbonate. Among them, adopting the aryl carbonate exhibits an advantage of speedy reaction. On the other hand, phenols having a high boiling point and which are made of the aryl carbonate are obtained as a by-product, but any lower residual volume of the phenols in the polycarbonate diol products is preferred. It can be a polymerization inhibitor because of a monofunctional compound and an irritating material.

Specific examples of the dialkyl carbonate, the diaryl carbonate, and the alkylene carbonatethe which are diester carbonates which can be used for producing the polycarbonate diol related to the first aspect of the present invention are as follows:

Examples of the dialkyl carbonate includes dimethyl carbonate, diethyl carbonate, dibutyl carbonate, dicyclohexyl carbonate, diisobutyl carbonate, ethyl-n-butyl carbonate, and ethyl-isobutyl carbonate, while dimethyl carbonate and diethyl carbonate are preferred.

Examples of the diaryl carbonate includes diphenyl carbonate, ditolyl carbonate, bis(chlorophenyl) carbonate, di-m-cresyl carbonate, while diphenyl carbonate is preferred.

Further, alkylene carbonate example includes, ethylene carbonate, trimethylene carbonate, tetramethylene carbonate, 1,2-propylene carbonate, 1,2-butylene carbonate, 1,3-butylene carbonate, 2,3-butylene carbonate, 1,2-pentylene carbonate, 1,3-pentylene carbonate, 1,4-pentylene carbonate, 1,5-pentylene carbonate, 2,3-pentylene carbonate, 2,4-pentylene carbonate, and neopentyl carbonate, while ethylene carbonate is preferred.

These may be used by one type alone, or by two or more types together.

Among them, diaryl carbonate is excellent in reaction property and preferred because of its effectiveness in industrial producing, while diphenyl carbonate is easily available inexpesively as an industrial raw material, so it is more preferred.

[Diol]

On the other hand, among the diol, followings are specific diol examples giving the Structure (A) and (B) included in the polycarbonate diol related to the first aspect of the present invention.

(Raw Material Diol of Structure (A))

Specific raw material diol examples giving the Structure (A) includes isosorbide, isomannide and isoidide, which are stereoisomers of isosorbide, while these may be used by one type alone or by two types or more together. Among them, the isosorbide is preferred since it is easily obtained by dehydration of sorbitol and is commercially available by industrial volume.

(Structure (B) Raw Material Diol)

Specific raw material diol examples giving Structure (B) include the aforementioned diols having 1 to 15 carbons which may contain hetero atom, or preferably the diols having 2 to 10 carbons as follows:

Terminal diols of straight chain hydrocarbons including ethylene glycol, 1,3-propane diol, 1,4-butane diol, 1,5-pentane diol, 1,6-hexanediol, 1,7-heptane diol, 1,8-octane diol, 1,9-nonane diol, 1,10-decane diol, 1,11-undecane diol and 1,12-dodecane diol;

Chain diols having ethers including diethylene glycol, triethylene glycol, tetraethylene glycol, pentaethylene glycol, polyethylene glycol, polypropylene glycol, and polytetramethylene glycol;

Thioether diols including bishydroxyethylthioether;

Diols having a branched chain including 2-methyl-1,3-propane diol, 2-ethyl-1,3-propane diol, 2-butyl-1,3-propane diol, 2,2-dimethyl-1,3-propane diol, 2-ethyl-2-butyl-1,3-propane diol, 2,2-diethyl-1,3-propane diol, 2-pentyl-2-propyl-1,3-propane diol, 3-methyl-1,5-pentane diol, 3,3-dimethyl-1,5-pentane diol, 2,2,4,4-tetramethyl-1,5-pentane diol, 2-ethyl-1,6-hexanediol, and 2,2,9,9-tetramethyl-1,10-decane diol;

Diols having alicyclic structure including 1,3-cyclohexanediol, 1,4-cyclohexanediol, 1,4-cyclohexanedimethanol, 4,4-dicyclohexyl dimethylmethane diol, 2,2'-bis(4-hydroxycyclohexyl)propane, 1,4-dihydroxyethylcyclohexane, 4,4'-isopropylidenedicyclohexanol, and 4,4'-isopropylidenebis(2,2'-hydroxyethoxycyclohexane), norbornane-2,3-dimethanol;

Diols having ring group with hetero atoms in its ring including 2,5-bis(hydroxymethyl)tetrahydrofuran, 3,4-dihydroxytetrahydrofuran, 3,9-bis(1,1-dimethyl-2-hydroxyethyl)-2,4,8,10-tetraoxaspiro[5.5]undecane (cas number: 1455-42-1), and 2-(5-ethyl-5-hydroxymethyl-1,3-dioxane-2-yl)-2-methylpropane-1-ol (cas number: 59802-10-7);

Nitrogen-containing diols including diethanolamine, and N-methyl-diethanolamine;

Sulfur-containing diols including bis(hydroxyethyl)sulfide;

Among these diols, more preferable raw material diols in terms of industrial availability, excellent physical property regarding the obtained-polycarbonate diol and polyurethane include ethylene glycol, 1,3-propanediol, 1,4-butane diol, 1,5-pentane diol, 1,6-hexanediol, and 1,7-heptane diol for straight chain carbon terminal diols, while diethylene glycol, triethylene glycol, tetraethylene glycol, polypropylene glycol, and polytetramethylene glycol for chain diols having ether group, while 2-methyl-1,3-propane diol, 2-ethyl-1,3-propane diol, 2,2-dimethyl-1,3-propane diol, 2-ethyl-2-butyl-1,3-propane diol, 2,2-diethyl-1,3-propane diol, 3-methyl-1,5-pentane diol, 3,3-dimethyl-1,5-pentane diol, 2,2,4,4-tetramethyl-1,5-pentane diol, and 2-ethyl-1,6-hexanediol for diols having branched chains, while 1,3-cyclohexanediol, 1,4-cyclohexanediol, 1,4-cyclohexanedimethanol, 4,4-dicyclohexyl dimethylmethane diol, 2,2'-bis(4-hydroxycyclohexyl) propane, 4,4'-isopropylidenedicyclohexanol, and norbornane-2,3-dimethanol for diols having alicyclic structure, while 3,4-dihydroxytetrahydrofuran, 3,9-bis(1,1-dimethyl-2-hydroxyethyl)-2,4,8,10-tetraoxaspiro[5.5]undecane (cas number: 1455-42-1), 2-(5-ethyl-5-hydroxymethyl-1,3-dioxane-2-yl)-2-methylpropane-1-ol (cas number: 59802-10-7) for diols having ring group with hetero atoms in its ring;

These diols may be used by one type alone, or by two or more types together.

{Diol for Structure (A)}

The characteristics of the polycarbonate diol related to the first aspect of the present invention is including Structure (A), while the aforementioned diols giving this Structure (A) (hereinafter, it may be referred as "Diol for Structure (A)") may be unstable, and must be careful for saving and usage. For example, isosorbide is gradually oxidized with oxygen, so for storage and handling during producing, a deoxygenating agent must be used or a nitrogen atmosphere must be prepared to prevent decomposition by oxygen. Also, water must not be mixed in. When isosorbide is oxidized, a decomposition product including a formic acid is generated. For example, when a polycarbonate diol is produced by using isosorbide containing the decomposition product, the obtained polycarbonate diol may have colors or its physical properties may be noticeably deteriorated. It also affects polymerization reaction, and a polymer with its target molecular weight may not be obtained.

As a countermeasure against these, an approach described in known documents may be arbitrarily adopted. For example, Japanese patent laid open 2009-161745 A regulates a preferable amount of formic acids to be contained in a raw material of dihydroxy compound such as isosorbide used for producing a polycarbonate, and describes that using the defined amount or less of dihydroxy compound results in a polycarbonate with better physical properties.

This is true for producing the polycarbonate diol related to the first aspect of the present invention, and the amount of formic acids to be contained in the Diol for Structure (A) is not specifically limited, but its upper limit is usually 20 ppm, preferably 10 ppm, more preferably 5 ppm, while the lower limit is 0.1 ppm or preferably 1 ppm.

These diols for Structure (A) generate acid substances such as formic acid when deteriorated due to oxidization, which tends to result in lower pH. Therefore, pH may be used for evaluation as an index for available diol for Structure (A). For example, as described in WO 09/057,609, pH may be measured as an aqueous solution containing 40% of raw material diol by a pH indicator.

The lower limit of pH of the aqueous solution containing 40% of diol for Structure (A) necessary for producing the polycarbonate diol related to the first aspect of the present invention is not specifically limited, but is usually pH 3, preferably pH 4, and more preferably pH 5, while its upper limit is pH 11, and preferably pH 10.

Diol for Structure (A) generates a peroxide by oxidative degradation. Any lower amount of this peroxide is preferred because it may cause coloration in producing a polycarbonate diol or during urethane reaction. The amount of peroxide in diol for Structure (A) relative to the weight of diol for Structure (A) is usually 10 ppm or less, preferably 5 ppm or less, more preferably 3 ppm or less, and further preferably 1 ppm or less. Its lower limit is not specifically limited, but usually, 0.01 ppm or more.

When diol for Structure (A) contains a metal of Group 1 and/or 2 on the periodic table, the reaction speed may be influenced during reaction for forming polycarbonate or the polyurethane reaction of the obtained polycarbonate diol. Therefore, the content of the metal of Group 1 and/or 2 on the periodic table in the diol for Structure (A) is not specifically limited, but any lower content is preferred, while its upper limit of the metal weight ratio, relative to weight of diol for Structure (A), is usually 10 ppm, preferably 5 ppm, more preferably 3 ppm, further preferably 1 ppm, or specially preferably nothing of the metal of Group 1 and/or 2 on the periodic table.

When a halogen component such as a chloride ion or a bromide ion is contained in the Diol for Structure (A), it may influence on reactions or causes coloration during reaction for forming polycarbonate or the polyurethane reaction of the obtained polycarbonate diol, therefore, smaller content is preferred. Usually, the upper limit of halogen component content in diol for Structure (A) is, relative to diol for Structure (A) weight, 10 ppm, preferably 5 ppm, and more preferably 1 ppm as halogen content.

The diol for Structure (A) which is deteriorated by oxidation, or which contains the above impure substance, can be purified by distillation, etc., for example. Therefore, when the diol is distilled before polymerization usage and contains the impurities within the above range, the diol can be used. In order to prevent it from oxidative degradation again after distillation, adding a stabilization agent is useful. Any usually and generally used organic compound as anti-oxidant can be used without limitation as a specific stabilization agent, which includes phenol stabilization agent such as butylhydroxytoluene, butylhydroxyanisole, 2,6-di-t-butyl-4-methylphenol, 2-[1-(2-hydroxy-3,5-di-t-pentylphenyl)ethyl]-6-di-t-pentylphenylacrylate (manufactured by Sumitomo Chemical, product name: Sumilizer (registered trademark) GS), and a phosphorous stabilization agent such as a 6-[3-(3-t-butyl-4-hydroxy-5-methylphenyl)propoxy]-2,4,8,10-tetra-t-butyldibenz [d,f][1,3,2] dioxaphosphepin (manufactured by Sumitomo Chemical, product name: Sumilizer (registered trademark) GP), bis(2,4-di-t-butylphenyl) pentaerythritol diphosphite, for example.

{Molecular Weight/Molecular Weight Distribution}

The lower limit of the number average molecular weight (Mn) of polycarbonate diol related to the first aspect the present invention is usually 250, preferably 500, more preferably 700, and especially preferably 1,000. On the other hand, the upper limit is usually 5,000, preferably 4,000 or more preferably 3,000. When the number average molecular weight of polycarbonate diol is lower than the aforementioned lower limit, enough hardness which is a characteristic of the present invention may not be obtained after urethanization. On the other hand, when it exceeds the aforementioned upper limit, a problem is paused during polyurethanization handling.

The molecular weight distribution of the polycarbonate diol related to the first aspect of the present invention (Mw/Mn) is not specifically limited, but its lower limit is usually 1.5, and preferably 2.0. Usually the upper limit is 3.5, and preferably 3.0.

When the molecular weight distribution exceeds the above range, the physical properties of the polyurethane produced by using this polycarbonate diol tends to be deteriorated such as hardening under low temperature, or poor stretching, while trying to produce a polycarbonate diol of which molecular weight distribution is lower than the above range, a high-level purification such as excluding oligomer may be required.

Where, Mw represents the weight-average molecular weight and Mn represents the number average molecular weight, which can be usually obtained by gel permeation chromatography (GPC) measurement.

{The Proportion of Numbers where Molecular Chain Terminal of the Polycarbonate Diol is Either an Alkyloxy Group or an Aryloxy Group and Hydroxy Value Thereof}

The polycarbonate diol related to the first aspect of the present invention has basically hydroxyl group for its polymer terminal structure. However, the polycarbonate diol product obtained by the reaction of a diol and a diester carbonate, may partially include an impurity of which polymer terminal does not have a hydroxyl group structure. A specific example of that structure has a molecular chain terminal which is either an alkyloxy group or an aryloxy group, most of which has a structure derived from a diester carbonate.

For example, when a diphenyl carbonate is used as a diester carbonate, a phenoxy group (PhO—) may remain as an aryloxy group, when a dimethyl carbonate is used methoxy group (MeO—) may remain as alkyloxy group, when a diethyl carbonate is used ethoxy group (EtO—) may remain as a terminal group, and when ethylene carbonate is used hydroxyethoxy group (HOCH$_2$CH$_2$O—) may remain as a terminal group (where Ph represents a phenyl group, Me represents a methyl group and Et represents an ethyl group).

In the present invention, the proportion of the structure, in which a molecular chain terminal included in a polycarbonate diol products is either an alkyloxy group or an aryloxy group, is usually 5 mol % or less of all terminals as the number of its terminal groups, preferably 3 mol % or less, and more preferably 1 mol % or less. The lower limit of the proportion of numbers where its molecular chain terminal is either an alkyloxy group or an aryloxy group is not specifically limited, and usually is 0.01 mol %, preferably 0.001 mol %, and most preferably 0 mol %. When the proportion of alkyloxy or aryloxy group terminals is large, a problem such as degree of polymerization remaining low during polyurethanization may occur.

The polycarbonate diol related to the first aspect of the present invention is, as discussed above, the proportion of numbers where its molecular chain terminal is either an alkyloxy group or an aryloxy group is usually 5% or less, both terminal groups of the molecular chain are basically hydroxyl groups, which is the structure where this hydroxyl group can be reacted with isocyanate during polyurethanization reaction.

The hydroxyl value of the polycarbonate diol related to the first aspect of the present invention is not specifically limited, but the lower limit is usually 10 mg-KOH/g, preferably 20 mg-KOH/g, and more preferably 35 mg-KOH/g. And the upper limit is usually 230 mg-KOH/g, preferably 160 mg-KOH/g, and more preferably 130 mg-KOH/g. When the hydroxyl value is lower than the above lower limit, viscosity of the polycarbonate diol is too high and its polyurethanization handling may become difficult, while it is higher than the above upper limit strength and hardness of the obtained-polyurethane may not be enough after polyurethanization.

{Ether Structure}

The polycarbonate diol related to the first aspect of the present invention is based on a structure in which a raw material diol is polymerized by a carbonate group. However, some producing method may partially mix an ether structure which is not the aforementioned Structure (A), while when that amount increases, its weather and heat resistance may be deteriorated, so it is preferred that the proportion of non-Structure (A) ether structure is not too large.

In terms of ensuring characteristics such as weather and heat resistance by reducing the proportion of non-Structure (A) ether structure in the polycarbonate diol, the ratio of non-Structure (A) ether binding and the carbonate binding in the polycarbonate diol molecular chains related to the first aspect of the present invention is not specifically limited, but is usually 2/98 or less by mol ratio, preferably 1/99 or less, and more preferably 0.5/99.5 or less.

When Structure (B) also contains an ether binding, it is preferred to have not too large ratio of an ether structure which is neither Structure (A) nor (B).
In such a case, the ratio of the ether binding which is neither Structure (A) nor (B) and the carbonate binding in the polycarbonate diol molecular chain related to the first aspect of the present invention is not specifically limited, but is usually 2/98 or less by mol ratio, preferably 1/99 or less, and more preferably 0.5/99.5 or less.

{Viscosity/Solvent Dissolution Property}

The polycarbonate diol related to the first aspect of the present invention usually shows a property of a liquid-like to wax-like white turbidity solid substance around a room temperature, while heating it can lower its viscosity for better handling. It can also be dissolved into amide solvent such as dimethylformamide, dimethylacetamide, ester solvent such as γ-butyrolactone, sulfoxide solvent such as dimethyl sulfoxide for easy transportation and better reaction.

The property of the polycarbonate diol related to the first aspect of the present invention is as mentioned above a liquid-like to wax-like white turbidity solid substance around a room temperature, and its properties vary according to a temperature. In terms of viscosity, for example, the lower limit of the viscosity of the polycarbonate diol related to the first aspect of the present invention at 40° C. is preferably 0.1 Pa·s, more preferably 1 Pa·s, and further preferably 5 Pa·s, while the upper limit is preferably 108 Pa·s, more preferably 107 Pa·s, and further preferably 106 Pa·s.

{APHA Value}

The color of the polycarbonate diol related to the first aspect of the present invention is preferred to be in a range which does not affect a polyurethane color, while its coloration degree is not specifically limited by Hazen color number (based on JIS K0071-1) (APHA), but is preferably 100 or less, more preferably 50 or less, and further preferably 30 or less.

{Impurity Content}

[Phenols]

The amount of phenols contained in the polycarbonate diol related to the first aspect of the present invention is not specifically limited, but the amount is preferably any smaller, preferably 0.1 weight % or less (hereinafter, "weight %" may be referred as "mass %"), is more preferably 0.01 weight % or less, and further preferably 0.001 weight % or less. Because phenol is monofunctionalized compound, it can be a polymerization inhibitor during polyurethanization as well as an irritating material.

[Diester Carbonate]

In the polycarbonate diol product related to the first aspect of the present invention, a diester carbonate sometimes remain after being used as a raw material during producing, and the remained amount of the diester carbonate in the polycarbonate diol product related to the first aspect of the present invention is not limited, but any smaller amount is preferred, while the upper limit is usually 5 weight %, preferably 3 weight %, and more preferably 1 weight %. Too many diester carbonate content in the polycarbonate diol may obstruct reaction during polyurethanization. On the other hand, the lower limit is not specifically limited, but is 0.1 weight %, preferably 0.01 weight %, and more preferably 0 weight %.

[Diol]

In the polycarbonate diol related to the first aspect of the present invention, a raw material diol may remain after being used for producing. The remained amount of raw material diol in the polycarbonate diol related to the first aspect of the present invention is not limited, but any smaller amount is preferred, while it is usually 10 weight % or less, preferably 5 weight % or less, more preferably 3 weight % or less, or more preferably 1 weight % or less, preferably 0.1 weight % or less, and more preferably 0.05 weight % or less. When at least one of diols selected from isosorbide, isomannide, or isoidide (hereinafter, to be abbreviated as "isosorbides") is used, any smaller amount of the isosorbides remaining in the polycarbonate diol is preferred, while it is usually 10 weight % or less, preferably 5 weight % or less, more preferably 3 weight % or less, further preferably 1 weight % or less, specially preferably 0.1 weight % or less, and most preferably 0.01 weight % or less. When too much amount of the raw material diol remains in the polycarbonate diol, not enough molecular length of the soft segment part is obtained after polyurethanizatoin.

The diol which was a raw material of polyurethane diol can be identified by NMR measurement of a polycarbonate diol product, NMR measurement and/or GC and LC measurement of unreacted diols contained in the product, and if an unreacted product remains, the diester carbonate can be identified by NMR measurements and/or GC and LC measurements. In addition, impurities such as an alcohol component to be made a byproduct during the diester carbonate reaction are identified by NMR measurements and/or GC and LC measurement of products, which can estimate the structure of the raw material diester carbonate.

[Transesterification Catalyst]

In producing the polycarbonate diol related to the first aspect of the present invention, as described later, a transesterification catalyst may be used as required in order to promote polymerization. In such a case, the catalyst may remain in the obtained polycarbonate diol, but if too much catalyst remains, controlling the reaction is difficult during polyurethanization reaction, and the polyurethanization reaction is accelerated more than expected to cause gelation, which may not result in an uniform polyurethane, so no catalyst remaining is preferred.

The upper limit of remained catalyst amount in the polycarbonate diol is not specifically limited, but for obtaining a homogeneous polyurethane from this polycarbonate diol, the upper limit is usually 100 weight ppm in terms of catalyst metal, preferably 50 weight ppm, more preferably 30 weight ppm, and especially preferably 10 weight ppm. A type of remaining metal includes a catalytic activity component-metal having an esterification reaction ability as mentioned below.

In addition, the lower limit of the catalyst amount remaining in the polycarbonate diol is not specifically limited, but the lower limit is usually 0.01 weight ppm in terms of catalyst metal, preferably 0.1 weight ppm, more preferably 1 weight ppm, and especially preferably 5 weight ppm. Removing a catalyst used for producing a polycarbonate diol is usually difficult after producing, and controlling the amount of remaining catalyst to be lower than the lower limit value of the amount as described later is difficult.

The amount of the aforementioned catalyst in the polycarbonate diol can be adjusted by the catalyst amount to be used for producing, or catalyst isolation by filtering the product, etc. or catalyst extraction using a solvent such as water.

[Cyclic Carbonate]

A polycarbonate diol product may contain a cyclic carbonate which was subgenerated during producing. For example, when a 1,3-propanediol is applied as a raw material diol, 1,3-dioxane-2-on or a cyclic carbonate consisting of two or more molecules of this, etc. may be generated as a cyclic compound and contained in the polycarbonate diol. These compounds are impurities which may cause a side reaction during polyurethanization reaction, so removing them during producing is preferred.

Content of these cyclic carbonates of impurities contained in the polycarbonate diol related to the first aspect of the present invention is not limited, but is usually 3 weight % or less, preferably 1 weight % or less, and more preferably 0.5 weight % or less.

{Urethanization Reaction Speed}

The reaction speed of urethanization reaction of the polycarbonate diol related to the first aspect of the present invention can be evaluated as a load value [V] of motor obtained through following steps. The load value [V] of motor is obtained by steps of, making the aforementioned polycarbonate diol to be an N,N-dimethylformamide solution, adding 0.98 times of a diphenylmethane diisocyanate relative to mol equivalent amount of the polycarbonate diol, using the motor as a power source, and agitating it for a specified amount of time by 100 rpm. The lower limit of the motor load in 30 minutes after a diphenylmethane diisocyanate is added is usually 0.10 V, preferably 0.13 V, more preferably 0.20 V, while the upper limit is usually 2.00 V, preferably 1.95 V, and more preferably 1.90 V. The lower limit of the motor load in 60 minutes after a diphenylmethane diisocyanate is added is usually 0.10 V, preferably 0.13 V, more preferably 0.20 V, while the upper limit is usually 2.00 V, preferably 1.95 V, and more preferably 1.90 V. If it lowers the above lower limit, polymerization may not proceed, while it exceeds the above upper limit, its molecular weight may be too high or gelation occurs.

Similarly, the lower limit of time (min.) when the motor load value reaches 0.7 V is usually 8 min., preferably 10 min, and more preferably 15 min., while the upper limit is usually 240 min., preferably 200 min., and more preferably 120 min. Similarly, the lower limit of time (min.) when the motor load value reaches 1.0 V is usually 2 min., preferably 5 min, and more preferably 10 min., while the upper limit is usually 120 min., preferably 90 min., and more preferably 60 min. If it lowers the above lower limit, its molecular weight may be too high or gelation occurs, while it exceeds the above upper limit, polymerization may not proceed.

The motor load value [V] can be measured by extracting the motor value when an N,N-dimethylformamide solution of the polycarbonate diol is agitated at 100 rpm from the motor load value after it is agitated for a certain amount of time by 100 rpm after a diphenylmethane diisocyanate is added. A motor of which rotation range is between 10 to 600 rpm, maximum torque at 600 rpm redline is around 0.49 N-m, its motor load value can be outputted between around 0 and 5 V is used, a 500 mL-separable flask is used as a reactor, four wings combining two anchor types are used as agitation wings, and then measurement is done under the condition of nitrogen circulation or encapsulation.

{Process of Production}

The polycarbonate diol related to the first aspect of the present invention can be produced by transesterification of a raw material diol represented by isosorbide giving the aforementioned structure (A), dials such as a raw material diol giving the aforementioned structure (B) used as required and the aforementioned diester carbonate, by using an esterification catalyst as required. For example, it can be obtained by reacting (i) at least one of diols selected from isosorbide, isomannide and isoidide, (ii) diol having 1-15 carbons which may contain hetero atom, and (iii) diester carbonate by use of a transesterification catalyst.

The following describes its producing method.

[Transesterification Catalyst]

Any metal which is generally known to have an esterification reaction ability may be used without limitation as a metal which can be used as a transesterification catalyst.

Examples of catalyst metals include a metal of Group 1 on the periodic table such as lithium, natrium, potassium, rubidium, and cesium; a metal of Group 2 on the periodic table such as magnesium, calcium, strontium, and barium; a metal of Group 4 on the periodic table such as titanium, zirconium; a metal of Group 5 on the periodic table such as hafnium; a metal of Group 9 on the periodic table such as cobalt; a metal of Group 12 on the periodic table such as zinc; a metal of Group 13 on the periodic table such as aluminum; a metal of Group 14 on the periodic table such as germanium, tin, lead; and a metal of Group 15 on the periodic table such as antimony, bismuth; and lanthanide metals such as lantern, cerium, europium, and ytterbium. Among them, in terms of esterification reaction acceleration, a metal of Group 1 on the periodic table, a metal of Group 2 on the periodic table, a metal of Group 4 on the periodic table, a metal of Group 5 on the periodic table, a metal of Group 9 on the periodic table, a metal of Group 12 on the periodic table, a metal of Group 13 on the periodic table, and a metal of Group 14 on the periodic table are preferred, while a metal of Group 1 on the periodic table and a metal of Group 2 on the periodic table are more preferred, while a metal of Group 2 on the periodic table is further preferred.

Among metals of Group 1 on the periodic table, lithium, potassium, and sodium are preferred, lithium and sodium are more preferred and sodium is further preferred. Among metals of Group 2 on the periodic table, magnesium, calcium, and barium are preferred, calcium and magnesium are more preferred, and magnesium is further preferred. These metals may be used as a simple metal, or as a metal compound such as hydroxide or salt thereof. Salt examples when used as salt includes halide salt such as chloride, bromide, and iodide; carboxylate such as acetate, formate, and benzoate; sulfonate such as methanesulfonic acid, toluenesulfonic acid, and trifluoromethanesulfonic acid; phosphorus-containing salt such as phosphate, hydrogenphosphate, and dihydrogenphosphate; and acetylacetonate salt; etc. A catalyst metal can be used as alkoxide such as methoxide and ethoxide.

Among them, preferably acetate, nitrate, sulfate, carbonate, phosphate, hydroxide, halide, and alkoxide are used of metals of Group 1 on the periodic table, metals of Group 2 on the periodic table, metal of Group 4 on the periodic table, metals of Group 5 on the periodic table, metals of Group 9 on the periodic table, metals of Group 12 on the periodic table, metal of Group 13 on the periodic table, and metals of Group 14 on the periodic table, while more preferably acetate, carbonate and hydroxide of metals of Group 1 on the periodic table, or metals of Group 2 on the periodic table, while further preferably an acetate of metals of Group 2 on the periodic table.

These metals and metal compounds may be used by one type alone, or by two or more types together.

Specific examples of compounds using a Group 1 metal on the periodic table of an a transesterification catalyst includes sodium hydroxide, potassium hydroxide, cesium hydroxide, lithium hydroxide, sodium hydrogen carbonate, sodium carbonate, potassium carbonate, cesium carbonate, lithium carbonate, sodium acetate, potassium acetate, cesium acetate, lithium acetate, sodium stearate, potassium stearate, cesium stearate, lithium stearate, sodium boron hydride, sodium phenylborate, sodium benzoate, potassium benzoate, cesium benzoate, lithium benzoate, dibasic sodium phosphate, dibasic potassium phosphate, dibasic lithium phosphate, disodium phenyl phosphate; bisphenol A including disodium salt, dipotassium salt, dicesium salt, dilithium salt; phenol sodium salt, potassium salt, cesium salt, and lithium salt, etc.

Compound examples using a Group 2 metal on the periodic table includes magnesium hydroxide, calcium hydroxide, strontium hydroxide, barium hydroxide, magnesium hydrogen carbonate, calcium hydrogen carbonate, strontium hydrogen carbonate, barium hydrogen carbonate, magnesium carbonate, calcium carbonate, strontium carbonate, barium carbonate, magnesium acetate, calcium acetate, strontium acetate, barium acetate, magnesium stearate, calcium stearate, calcium benzoate, and magnesium phenylphosphate.

Compound examples using a Group 4 metal on the periodic table, a Group 12 metal on the periodic table and a Group 14 metal on the periodic table includes titaniumalkoxide such as tetraethyltitanate, tetraisopropyltitanate, and tetra-n-butyltitanate; titanium halide such as titanium tetrachloride; zinc salt such as zinc acetate, zinc benzoate, and zinc 2-ethylhexanoate; tin compound such as tin chloride (II), tin chloride(IV), tin acetate(II), tin acetate(IV), dibutyltin dilaurate, dibutyltin oxide, and dibutyltin dimethoxide; zirconium compound such as zirconium acetylacetonato, zirconium oxyacetate, and zirconium tetrabutoxide; and lead compound such as lead acetate(II), lead acetate(IV), and lead chloride(IV).

[Use Proportion of Raw Materials]

For producing the polycarbonate diol related to the first aspect of the present invention, the use amount of diester carbonate is not specifically limited, but usually by the mol ratio to a total 1 mol of diols the lower limit is preferably 0.50, more preferably 0.70, further preferably 0.80, more and more preferably 0.90, especially preferably 0.95, and the most preferably 0.98, while the upper limit is usually 1.20, preferably 1.15, and more preferably 1.10. If the amount of diester carbonate exceeds the aforementioned upper limit, terminal group of the polycarbonate diol to be obtained tends not to be a hydroxyl group and the ratio of groups other than hydroxyl group may be increased, or the molecular weight does not reach the predefined range and the polycarbonate diol related to the first aspect of the present invention cannot be produced, and if the amount of diester carbonate is lower than the aforementioned lower limit, polymerization may not be processed to a predefined molecular weight.

In producing the polycarbonate diol related to the first aspect of the present invention, the ratio of the amount of the raw material diol giving Structure (A) and the amount of the raw material diol giving Structure (B) (hereinafter, it may be referred as "Raw material (A)/Raw material (B) ratio) is usually, by mol ratio, Raw material diol giving Structure (A)/Raw material giving Structure (B)=100/0 to 1/99. Introducing Structure (B) into a molecular chain disarranges the polycarbonate diol regularity, lowers the melting point and viscosity, and therefore improves handling property. Effects of the present invention such as the aforementioned rigidity and hydrophilic properties, etc. are mainly introduced by the Structure (A) part, so if the ratio of Structure (A) part is too small in the polycarbonate diol related to the first aspect of the present invention, its effects may not be obtained enough. Raw material (A)/raw material (B) ratio is preferably 100/0 to 10/90, more preferably 80/20 to 20/80, and further preferably 70/30 to 30/70.

When a transesterification catalyst is used for producing the polycarbonate diol related to the first aspect of the present invention, an amount to be used is preferably the amount which does not affect a performance if it remains in the obtained polycarbonate diol, while the weight ratio in terms of metal to the weight of a raw material diol as its upper limit is preferably 500 ppm, more preferably 100 ppm, and further preferably 50 ppm. On the other hand, the lower limit must be an amount which can exhibit enough polymerization activity, and preferably 0.01 ppm, more preferably 0.1 ppm, and further preferably 1 ppm.

[Reaction Conditions, etc.]

How to prepare a reaction raw material is not specifically limited, and can be arbitrarily selected from various kinds of approaches; an approach of preparing all amounts of a diol, a carbonate ester, and a catalyst altogether for reaction, an approach of firstly preparing the carbonate ester if the carbonate ester is a solid, heating for melting, and then adding the diol and the catalyst, an approach of firstly preparing the diol for melting conversely, and then adding the carbonate ester and the catalyst, and an approach of reacting a part of the diol and a carbonate ester or a chlorocarbonic ester to synthesize a carbonate diester derivative of the diol, and then reacting it with remaining diol. In the polycarbonate diol related to the first aspect of the present invention, to make the ratio of molecular chain terminal which is either an alkyloxy group or an aryloxy group to be 5% or less, an approach of adding a part of the diol to be used at the end of its reaction is also possible. In that case, the upper limit of the diol amount to be added at the end is usually 20% of the diol amount to be prepared, preferably 15%, and more preferably 10%, while the lower limit is 0.1%, preferably 0.5%, and more preferably 1.0%.

Reaction temperature during esterification reaction may be arbitrarily adopted as long as practicable reaction speed can be obtained at the temperature. The temperature is not specifically limited, but is usually 70° C. or higher, preferably 100° C. or higher, and more preferably 130° C. or higher. The temperature is usually 250° C. or lower, preferably 230° C. or lower, more preferably 200° C. or lower, further preferably lower than 180° C., especially preferably 170° C. or lower, and the most preferably 165° C. or lower. When the temperature exceeds the aforementioned upper limit, the obtained polycarbonate diol may be colored, an ether structure is generated, the aforementioned terminal (A) ratio (I) may become too large, therefore, in producing the polyurethane with the raw material of polycarbonate diol, a quality problem such as insufficient occurrence of a desired physical properties may be caused.

The reaction can be conducted under a normal pressure, but the esterification reaction is an equilibrated reaction, and distilling away a low boiling fraction to be generated to outside of a system can bias the reaction to a generation system. Consequently, it is preferred to adopt a reduced pressure condition for the latter half of the reaction to process the reaction while distilling the low boiling fraction away. Or, in the middle of the reaction, reducing the pressure gradually to distill away the low boiling fraction to be generated and processing the reaction is also possible.

Especially at the final period of the reaction, increasing the degree of reduced pressure to process the reaction can distill away a byproduct such as a monoalcohol, phenol, and further a cyclic carbonate, etc., which is preferred.

The reaction pressure at the end of this reaction is not specifically limited, but the upper limit is usually 10 kPa, preferably 5 kPa, and more preferably 1 kPa. In order to effectively distill away these low boiling fractions, an inert gas such as nitrogen, argon, and helium, etc. can be sent to its reaction system little by little to process the reaction.

When carbonate ester and/or diol having low-boiling point is used for esterification reaction, an approach, in which the reaction is to be conducted near the boiling point of the carbonate ester and/or the diol at its early reaction period, while the temperature is gradually increased as the reaction progresses for further reaction progress, is also adoptable. This case is preferable because distilling of unreacted carbonate ester can be blocked at the early reaction period. In order to prevent a raw material from being distilled at early reaction period, a reflux pipe can be attached to a reactor vessel to process the reaction while refluxing the carbonate ester and the diol. In this case, it is preferred that the prepared raw materials are not lost and its reagent amount ratio can be accurately adjusted.

Polymerization reaction is to be conducted while measuring the molecular weight of polycarbonate diol to be generated, and stops when the polycarbonate diol reaches the target molecular weight. The reaction time necessary for polymerization varies substantially, depending on a diol to be used, a carbonate ester, whether a catalyst is used or not, and its type, so it cannot be generalized, but the reaction time necessary for reaching the desired molecular weight is usually 50 hours or less, preferably 20 hours or less, and further preferably 10 hours or less.

As mentioned earlier, when a catalyst is used for polymerization reaction, the catalyst usually remains in the obtained polycarbonate diol, and when a metal catalyst remains, the reaction may not be controlled during polyurethanization reaction. In order to control this remaining catalyst influence, a phosphorous compound, for example, having the nearly-equal mols as the used transesterification catalyst may be added. Heating after the addition, as described below, can efficiently inactivate a transesterification catalyst.

A phosphorous compound to be used for inactivation of the transesterification catalyst includes, inorganic phosphoric acid such as phosphoric acid and phosphorous acid and organic phosphoric acid ester such as dibutyl phosphate, tributyl phosphate, trioctyl phosphate, triphenyl phosphate, and triphenyl phosphite, for example.

These may be used by one type alone, or by two or more types together.

The amount of the aforementioned phosphorous compound is not specifically limited, but as described above, the nearly-equivalent mols as the used transesterification catalyst is required, specifically, relative to 1 mols of the used transesterification catalyst, the upper limit is preferably 5 mols, and more preferably 2 mols, while the lower limit is preferably 0.8 mols and more preferably 1.0 mols. When any smaller amount of phosphorous compound is used, the inactivation of the transesterification catalyst is not enough in the aforementioned reaction product, and when the obtained polycarbonate diol is used as a raw material in producing a polyurethane, for example, reactivity of the polycarbonate diol to the isocyanate group may not be reduced enough. When a phosphorous compound exceeding this range is used, the obtained polycarbonate diol may be colored.

The inactivation of transesterification catalyst can be conducted by adding a phosphorous compound at room temperature, but heating process further improves the result. The temperature for this heating process is not specifically limited, but the upper limit is preferably 150° C., more preferably 120° C., and further preferably 100° C., while the lower limit is preferably 50° C., more preferably 60° C., and further preferably 70° C. If the temperature is lower than the lower limit, it takes long time to inactivate the transesterification catalyst inefficiently, and the degree of inactivation may not be enough. On the other hand, at the temperature over 150° C., the obtained polycarbonate diol may be colored.

The reaction time with a phosphorous compound is not specifically limited, but is usually 1 to 5 hours.

[Purification]

After the reaction, purification can be conducted in order to remove an impurity of which terminal structure is an alkyloxy group, an impurity which is an aryloxy group, phenols, a raw material diol, a carbonate ester, a cyclic carbonate byproduct having low-boiling point, and an added catalyst, etc. For those purification, a distilling approach can be adopted to remove a low boiling compound. As a specific distilling approach, like vacuum distillation, hydrodistillation, and thin-film evaporation, its embodiment is not limited, but an arbitrary approach can be adopted. In order to remove water-soluble impurities, water, alkaline water, acid water, and chelating agent dissolved solution, etc. may be used for cleaning. In that case, a compound to be dissolved into water can be arbitrarily selected.

[Polyurethane]

The polycarbonate related to the first aspect of the present invention is obtained by using the polycarbonate diol related to the first aspect of the above present invention.

An approach for producing the polyurethane related to the first aspect of the present invention by using the polycarbonate diol related to the first aspect of the present invention usually adopts a known polyurethanization reaction condition for producing the polyurethane.

For example, reacting the polycarbonate diol related to the first aspect of the present invention with polyisocyanate and a chain extender in the range of a room temperature to 200° C. to produce the polyurethane related to the first aspect of the present invention. Also, firstly reacting the polycarbonate diol related to the first aspect of the present invention with an excess of polyisocyanate to produce a prepolymer having terminal isocyanate, and increase the polymerization degree by using the chain extender to produce the polyurethane.

{Reactive Reagent, etc.}

[Polyisocyanate]

A polyisocyanate used for producing the polyurethane by using the polycarbonate diol related to the first aspect of the present invention includes various kinds of known polyisocyanate compounds such as fatty series, alicyclic series, and aromatic series.

For example, fatty series diisocyanate such as tetramethylene diisocyanate, hexamethylene diisocyanate, 2,2,4-trimethyl hexamethylene diisocyanate, 2,4,4-trimethyl hexamethylene diisocyanate, lysinediisocyanate and dimerdiisocyanate which is obtained by converting carboxyl group of dimer acid into isocyanate group; alicyclic diisocyanate such as 1,4-cyclohexanediisocyanate, isophorone diisocyanate, 1-methyl-2,4-cyclohexanediisocyanate, 1-methyl-2,6-cyclohexanediisocyanate, 4,4'-dicyclohexyl-methanediisocyanate and 1,3-bis(isocyanatemethyl)cyclohexane; and aromatic diisocyanate such as a xylylene diisocyanate, 4,4'-diphenyldiisocyanate, 2,4-tolylenediisocyanate, 2,6-tolylenediisocyanate, m-phenylenediisocyanate, p-phenylenediisocyanate, 4,4'-diphenylmethane diisocyanate, 4,4'-diphenyldimethylmethanediisocyanate, 4,4'-dibenzyl diisocyanate, dialkyl diphenylmethane diisocyanate, tetraalkyl diphenylmethane diisocyanate, 1,5-naphthylene diisocyanate, 3,3'-dimethyl-4,4'-biphenylene diisocyanate, polymethylene polyphenyliso-cyanate, phenylenediisocyanate and m-tetramethylxylylene diisocyanate. These may be used by one type alone, or by two or more types together.

Among them, the most preferable organic diisocyanate is the 4,4'-diphenylmethane diisocyanate, the hexamethylene diisocyanate and the isophorone diisocyanate because the physical properties balance of the polyurethane to be obtained is preferable and these compounds can be easily and inexpensively obtained with high volume in terms of industrial view point.

[Chain Extender]

The chain extender to be used for producing the polyurethane related to the first aspect of the present invention is a low-molecular weight compound having at least two active hydrogens which react with isocyanate group, and usually is exemplified by polyol and polyamine.

Specific examples of these include straight chain diols such as ethylene glycol, diethylene glycol, 1,3-propylene glycol, 1,4-butanediol, 1,5-pentanediol, 1,6-hexanediol, 2,4-heptanediol, 1,8-octanediol, 1,4-dimethylol hexane, 1,9-nonanediol, and 1,12-dodecanediol, dimerdiol; diols having branched chains such as 2-methyl-1,3-propanediol, 2,2-dimethyl-1,3-propanediol, 2,2-diethyl-1,3-propanediol, 2-methyl-2-propyl-1,3-propanediol, 2-ethyl-1,3-hexanediol, 2,2,4-trimethyl-1,3-pentanediol, 2-methyl-1,8-octanediol, and 2-butyl-2-ethyl-1,3-propanediol; diols having a ring group such as 1,4-cyclohexanediol, 1,4-cyclohexanedimethanol, and 1,4-dihydroxyethylcyclohexane; diols having aromatic group such as xylylene glycol, 1,4-dihydroxyethyl benzene, and 4,4'-methylenebis(hydroxyethyl benzene; polyols such as glycerin, trimethylolpropane, and pentaerythritol; hydroxy amine such as N-methylethanolamine, and N-ethylethanolamine; polyamine such as ethylene diamine, 1,3-propane diamine, hexamethylenediamine, triethylenetetramine, diethylene triamine, isophoronediamine, 4,4'-diaminodicyclohexylmetane, 2-hydroxyethylpropylene diamine, di-2-hydroxyethylethylene diamine, di-2-hydroxyethylpropylene diamine, 2-hydroxypropylethylene diamine, di-2-hydroxypropylethylene diamine, 4,4'-diphenylmethanediamine, methylenebis(o-chloroaniline), xylylenediamine, diphenyldiamine, tolylenediamine, hydrazine, piperazine, and N,N'-diaminopiperazine; and water.

These chain extenders may be used by one type alone, or by two or more types together.

The most preferable chain extender among them includes 1,4-butanediol, 1,5-pentanediol, 1,6-hexanediol, 1,8-octanediol, 1,9-nonanediol, 1,4-cyclohexanedimethanol, 1,4-dihydroxyethylcyclohexane, ethylene diamine, and 1,3-propane diamine, because the physical properties balance of the polyurethane to be obtained is preferable and these compouds can be easily and inexpensively obtained with high volume in terms of industrial view point.

[Chain Terminator]

In producing the polyurethane related to the first aspect of the present invention, in order to control the obtained polyurethane molecular weight, a chain terminator having one active hydrogen group may be used as required.

Examples of these chain terminators include aliphatic mono-ols having hydroxyl group such as ethanol, propanol, butanol, and hexanol, and aliphatic mono-amines having amino group such as diethylamine, dibutylamine, n-butylamine, monoethanolamine, and diethanolamine.

These may be used by one type alone, or by two or more types together.

[Catalyst]

In a polyurethane forming reaction for producing the polyurethane related to the first aspect of the present invention, an amine series catalyst such as triethylamine, N-ethylmorpholine, triethylene diamine, or tin compound such as tin series catalyst such as trimethyltin laurate or dibutyltin dilaurate, further a known urethane polymerization catalyst that is typified by organic metallic salt such as titanium series compound. The urethane polymerization catalyst may be used by one type alone, or by two or more types together.

[Other Polyol]

In producing the polyurethane related to the first aspect of the present invention, in addition to the polycarbonate diol related to the first aspect of the present invention, other known polyol may be used together, as required. Examples of those available known polyols include, polyoxyalkylene glycols such as polyethylene glycol, polypropylene glycol, and polyoxytetramethylene glycol (PTMG); alkylene oxide adduct of polyalchol such as ethylene oxide adduct and propylene oxide adduct of bisphenol A and glycerin; polyesterpolyol, polycaprolactonepolyol, and polycarbonatepolyol.

Examples of polyesterpolyol include a diacid such as adipic acid, phthalic acid, isophthalic acid, maleic acid, succinic acid, and fumaric acid, glycol series such as ethylene glycol, diethylene glycol, 1,3-propylene glycol, 1,4-butanediol, 1,5-pentanediol, 1,6-hexanediol, and trimethylolpropane.

Available polycarbonate polyol examples include a homopolycarbonate diol and a copolymerized polycarbonate diol which are produced from 1,4-butanediol, 1,5-pentanediol, 1,6-hexanediol, cyclohexanedimethanol, and 2-methylpropanediol.

When other polyols are used, in order to obtain enough effects of using the polycarbonate diol related to the first aspect of the present invention, the proportion of the polycarbonate diol related to the first aspect of the present invention among all polyols is not specifically limited, but is usually 30 weight % or more, especially 50 weight % or more is preferred.

[Solvent]

A solvent may be used for a polyurethane forming reaction for producing the polyurethane related to the first aspect of the present invention.

Preferable solvents include amide series solvent such as dimethylformamide, diethylformamide, dimethylacetamide, and N-methylpyrolidone; sulfoxide series solvent such as dimethyl sulfoxide; ether series solvent such as tetrahydrofuran, and dioxane; ketone series solvent such as methylisobutylketone, methylethylketone, and cyclohexanone; ester series solvent such as methyl acetate, ethyl acetate, and butyl acetate; and aromatic hydrocarbons solvent such as toluene and xylene. These solvents may be used by one type alone, or by a combined solvent of two types or more.

Preferable organic solvents among them are methylethylketone, ethyl acetate, toluene, dimethylformamide, dimethylacetamide, N-methylpyrolidone and dimethyl sulfoxide.

By using a polyurethane resin composition containing the polycarbonate diol related to the first aspect of the present invention, polydiisocyanate, and the aforementioned chain extender, a polyurethane resin of an aqueous dispersion can be produced.

{Process of Production}

As an approach for producing the polyurethane related to the first aspect of the present invention by using the above mentioned reaction reagent, all general producing methods used for experimentally or industrially can be adopted.

Examples of them include a method for mixing and reacting a polyol including the polycarbonate diol related to the first aspect of the present invention, a polyisocyanate, and a chain extender altogether (hereinafter, to be referred as "one-step method") and a method for firstly reacting a polyol including the polycarbonate diol related to the first aspect of the present invention and a polyisocyanate to arrange a prepolymer having isocyanate group at both terminals thereof, and then reacting the prepolymer with a chain extender (hereinafter, to be referred as "two-step method").

The two-step method goes through a process that prepares intermediates having isocyanate at both of terminals that are corresponding to a polyurethane soft segment, and the process is conducted in advance by reaction of a polyol containing the polycarbonate diol related to the first aspect of the present invention with an organic polyisocyanate of one equivalent or more. Reacting a prepolymer with a chain extender after an arrangement is done may enhance the molecular weight arrangement of the soft segment part, which is useful to ensure a phase separation of a soft segment from a hard segment.

[One-Step Method]

One-step method is also called one-shot method, which is a method for preparing a polyol containing the polycarbonate diol related to the first aspect of the present invention, a polyisocyanate, and a chain extender altogether for reaction.

The amount of polyisocyanate at the one-step method is not specifically limited, but when the total of the number of hydroxyl groups of polyol containing the polycarbonate diol related to the first aspect of the present invention, the number of hydroxyl groups and amino groups of chain extender are regarded as 1 equivalent weight, and the lower limit is usually 0.7 equivalent weight, preferably 0.8 equivalent weight, more preferably 0.9 equivalent weight, and especially preferably 0.95 equivalent weight, while the upper limit is usually 3.0 equivalent weight, preferably 2.0 equivalent weight, more preferably 1.5 equivalent weight, and further preferably 1.1 equivalent weight.

When the polyisocyanate amount is too large, unreacted isocyanate groups may cause side reaction, and desired physical properties may not be obtained, while when it is too small, the molecular weight of the polyurethane does not become large enough and the desired performance may not develop.

The amount of the chain extender is not specifically limited, but when the number of isocyanates of a polyisocyanate is subtracted from the number hydroxyl groups of polyol containing the polycarbonate diol related to the first aspect of the present invention and the subtracted-number is regarded as 1 equivalent weight, the lower limit is usually 0.7 equivalent weight, preferably 0.8 equivalent weight, more preferably 0.9 equivalent weight, and especially preferably 0.95 equivalent weight, while the upper limit is 3.0 equivalent weight, preferably 2.0 equivalent weight, more preferably 1.5 equivalent weight, especially preferably 1.1 equivalent weight. When the chain extender amount is too large, the obtained polyurethane is least soluble to a solvent and processing tends to be difficult, while when it is too small, the obtained polyurethane becomes too soft to exhibit enough strength, hardness, and an elastic recovery performance and/or an elastic retention capacity cannot be obtained, and the high-temperature property may be deteriorated.

[Two-Step Method]

The two-step method is also called a prepolymer method, comprising; reacting a polyisocyanate and a polyol containing the polycarbonate diol related to the first aspect of the present invention in advance by the polyisocyanate/polyol reaction equivalent weight ratio 1.0 to 10.00 to produce a prepolymer having isocyanate group at terminals thereof, and then adding a chain extender having an active hydrogen such as a polyalcohol and an amine compound to produce a polyurethane.

The two-step method can be adopted without a solvent or with a solvent together.

The polyurethane can be produced by the two-step method by either approach of the following (1) to (3);

(1) Without using a solvent, a polyisocyanate is directly reacted with a polyol containing a polycarbonate diol to produce a prepolymer and used for the following chain extension reaction as is.

(2) A prepolymer is produced by the (1) approach, solved into a solvent, and then used for the following chain extension reaction.

(3) A solvent is adopted from the first time to react polyisocyanate and polyol containing a polycarbonate diol, and then chain extension reaction is conducted in the solvent.

In the case of approach (1), it is important to obtain the polyurethane so that it can coexist with a solvent for activating the chain extender by an approach of solving the chain extender into a solvent, or introducing a prepolymer and the chain extender into the solvent together, etc.

The amount of a polyisocyanate at the two-step method is not specifically limited, but when the number of hydroxyl groups of a polyol containing the polycarbonate diol is regarded as 1 equivalent weight, the lower limit of the number of isocyanates is usually 1.0, and preferably 1.05, while the upper limit is usually 10.0, preferably 5.0, and more preferably 3.0.

When the amount of this isocyanate is too large, the excessive isocyanate groups may cause a side reaction to cause unpreferable influence on the polyurethane physical properties, while when it is too small the molecular weight of the obtained polyurethane may not increase enough and may cause a problem in strength and/or thermal stability.

The amount of the chain extender is not specifically limited, but relative to the equivalent amount of the isocyanate group contained in the prepolymer, the lower limit is usually 0.1, preferably 0.5, and more preferably 0.8, while the upper limit is usually 5.0, preferably 3.0, and more preferably 2.0.

During the above chain extension reaction, one functionality organic amine and alcohol can coexist in order to adjust the molecular weight.

During the chain extension reaction, each component is reacted within the range of 0 to 250° C., but this temperature varies, depending on the amount of a solvent, reactive properties of raw materials to be used, and/or reaction equipment, etc., and is not specifically limited. When the temperature is too low, the reaction speed is too slow and/or productivity may be deteriorated due to low solubility of raw materials and polymer substances, while when the temperature is too high, a side effect may occur or the obtained polyurethane may be decomposed. The chain extension reaction may be conducted under reduced pressure while degassing.

A catalyst or a stabilizer, etc. may be added for the chain extension reaction, as required.

Examples of catalysts include one or two types of triethylamine, tributylamine, dibutyltin dilaurate, stannous octoate, acetic acid, phosphoric acid, sulfuric acid, hydrochloric acid, and sulfonic acid, while examples of stabilizers include one or two types of 2,6-dibutyl-4-methylphenol, distearyl thiodipropionate, di-beta-naphthyl-phenylenediamine, and tri (dinonylphenyl)phosphite. However, when a chain extender with high reactivity such as short-chain fatty series amine is used, the reaction is preferred to be conducted without adding a catalyst.

[Water-Based Polyurethane Emulsion]

A water-based polyurethane emulsion can be produced by using the polycarbonate diol related to the first aspect of the present invention.

In this case, in producing a prepolymer by reacting a polyol containing a polycarbonate diol and a polyisocyanate, the prepolymer is obtained by mixing a compound having at least one hydrophilic functional group and at least two isocyanate reactive groups, and a polyurethane emulsion is obtained by reacting the obtained-prepolymer with a chain extender.

Here, a hydrophilic functional group of a compound having at least one hydrophilic functional group and at least two isocyanate reactive groups includes carboxylic acid group and sulfonic acid group, for example, which is neutralizable with alkaline group. Also, isocyanate reactive group means a group of forming urethane bond and urea bond by generally reacting with isocyanate such as hydroxyl group, primary amino group, and secondary amino group, etc., which are permitted to co-exist within the same molecule.

Examples of compound having at least one hydrophilic functional group and at least two isocyanate reactive groups specifically include 2,2'-dimethylol propionic acid, 2,2-methylolbutyric acid, and 2,2'-dimethylolvaleric acid. Further, diaminocarboxylic acid, for example lysine, cystine, and 3,5-diaminocarboxylic acid are exemplified. These may be used by one type alone, or by two or more types together. When these are actually used, they can be neutralized by alkaline compound such as amine including trimethyl amine, triethylamine, tri-n-propylamine, tributylamine, and triethanolamine, as well as sodium hydroxide, calcium hydroxide, and ammonia.

In producing the water-based polyurethane emulsion, as for the amount of a compound having at least one hydrophilic functional group and at least two isocyanate reactive groups, in order to raise dispersion performance against water, the lower limit is, relative to the weight of a polyol containing the polycarbonate diol related to the first aspect of the present invention, usually 1 weight %, preferably 5 weight %, and more preferably 10 weight %. On the other hand, if an excess amount is added, the characteristics of the polycarbonate diol related to the first aspect of the present invention may not be sustained, so the upper limit is usually 50 weight %, preferably 40 weight %, and more preferably 30 weight %.

For synthesizing or saving the water-based polyurethane emulsion, an anionic surfactant represented by higher fatty acid, resin acid, acidic fatty alcohol, sulfate ester, higher alkyl sulfonate, alkyl aryl sulfonate, sulfonated ricinus, sulfosuccinate ester, etc., cationic surfactant such as primary amine salt, secondary amine salt, tertiary amine salt, quaternary amine salt, and pyridinium salt or non-ionic surfactant, etc. represented by a known reaction product of ethylene oxide and long-chain fatty alcohol or phenols may be used together to maintain its emulsion stability.

When the polyurethane emulsion is made by reacting a prepolymer with a chain extender, the prepolymer may be neutralized as required and dispersed into water.

These created water-based polyurethane emulsion can be used for various kinds of application. In particular, a chemical raw material with a smaller environmental load is sought these days, a substitute for a conventional product is possible in order not to use an organic solvent.

Specific suited applications for the water-based polyurethane emulsion includes a coating agent, a water-based paint, an adhesive agent, a synthetic leather, and an artificial leather, for example. In particular, the water-based polyurethane emulsion produced by using the polycarbonate diol related to the first aspect of the present invention has structure (A) in the polycarbonate diol, therefore it is more suitable as a coating agent. etc. than the water-based polyurethane emulsion using the conventional polycarbonate diol because of its high hardness, high abrasion resistance, and long-term maintenance of the surface properties.

Also by using the polycarbonate diol related to the first aspect of the present invention, it is possible to react it with polyisocyanate, and then react with an acrylic acid ester or a methacrylate ester having a hydroxy group, to induce to urethane acrylate, or urethane methacrylate. The urethane acrylate and urethane methacrylate are widely used as a coating agent, its application is not specifically limited, and the polycarbonate diol related to the first aspect of the present invention can be used as a raw material. Furthermore, it can be used by converting a polymerized functional group from (meth)acrylate to glycidyl group, allyl group, or propargyl group.

{Additives}

To the polyurethane related to the first aspect of the present invention which was produced by using the polycarbonate diol related to the first aspect of the present invention, an addition agent such as a thermal stabilizer, a light stabilizer, a coloring agent, a bulking agent, a stabilizer, an ultraviolet absorber, an oxidation inhibitor, an anti-adhesive agent, a flame retardant, an age inhibitor, and an inorganic filler can be added and mixed as far as characteristics of the polyurethane related to the first aspect of the present invention is not damaged.

Compounds available as a thermal stabilizer include phosphorous compound such as phosphoric acid, phosphorous acid's fatty series, aromatic series or an alkyl group substituted aromatic series ester or hypophosphorous acid derivative, phenylphosphonic acid, phenylphosphine acid, diphenylphosphonic acid, polyphosphonate, dialkyl pentaerythritol diphosphite, dialkyl bisphenol-A-diphosphite; phenol-based derivative, in particular, hindered phenol compound; sulfur-containing compound such as thio-ether-based, dithioic acid salt-based, mercaptobenzimidazole-based, thiocarbanilide-based, thiodipropionic acid ester-based; tin-based compound such as tin maleate, and dibutyltin monoxide.

Specific examples of a hindered phenol compound include Irganox 1010 (product name: made by Ciba-Geigy K.K), Irganox 1520 (product name: made by Ciba-Geigy K.K), etc.

Examples of a phosphorous compound include PEP-36, PEP-24 G, HP-10 (all of these are product names; made by ADEKA Corporation), Irgafos 168 (product name: made by Ciba-Geigy K.K), etc. Specific examples of sulfur-containing compounds include a thioether compound such as a dilauryl thiodipropionate (DLTP), or a distearyl thiodipropionate (DSTP).

Examples of available light stabilizers include a benzotriazole-based, and a benzophenone-based compound, etc., and specifically "TINUVIN 622 LD", "TINUVIN 765" (both are made by Ciba Specialty Corp), "SANOL LS-2626", "SANOL LS-765) (both are made by Sankyosha Co., Ltd.), etc.

Examples of an ultraviolet absorber include "TINUVIN 328", "TINUVIN234" (both are made by Ciba Specialty Corp), etc.

Examples of a coloring agent include a dye such as a direct dye, an acid dye, a basic dye, and a metal complex dyestuff; an inorganic pigment such as carbon black, titanium oxide, zinc oxide, iron oxide and mica; and an organic pigment such as coupling azo-based, condensed azo-based, anthraquinone-based, thioindigo-based, dioxazon-based, and phthalocyanine-based, etc.

Examples of an inorganic filler include a short glass fiber, a carbon fiber, an alumina, a talc, a graphite, a melamine, and a white clay.

Examples of a flame retardant include an organic compound containing a phosphorus and a halogen, an organic compound containing bromine or chlorine, and an additive and reactive flame retardant such as ammonium polyphosphate, aluminum hydroxide, and antimony oxide.

These addition agents may be used by itself alone, or two or more types can be arbitrarily combined by an arbitrary ratio.

The lower limit of the additive amount of these addition agents is, to the polyurethane, preferably 0.01 weight %, more preferably 0.05 weight %, and further preferably 0.1 weight %, while the upper limit is preferably 10 weight %, more preferably 5 weight %, and further preferably 1 weight %. When the additive amount of the addition agent is too small, the addition effect cannot be enough, while when it is too large, precipitation or turbidity may occur in the polyurethane.

{Polyurethane Film/Polyurethane Plate}

In producing a film by using the polyurethane related to the first aspect of the present invention, the lower limit of the film thickness is usually 10 μm, preferably 20 μm, and more preferably 30 μm, while the upper limit is usually 1,000 μm, preferably 500 μm, and more preferably 100 μm.

When the film is too thick, enough moisture permeability may not be obtained, while it is too thin, its handling may become difficult because a pin hole is easily generated and/or the film may be blocked.

The polyurethane film related to the first aspect of the present invention is preferred to be used as a medical material such as a medical self-adhesive film, a sanitary material, a packing material, a decoration film, and any other moisture permeability material, etc. The polyurethane film related to the first aspect of the present invention may be the film which was formed on a base such as a cloth or a nonwoven fabric. In this case, the thickness of the polyurethane film itself may be further thinner than 10 μm.

A polyurethane plate can be produced by using the polyurethane related to the first aspect of the present invention. In that case, the upper limit of that plate thickness is not specifically limited, but the lower limit is usually 0.5 mm, preferably 1 mm and more preferably 3 mm.

[Molecular Weight]

The molecular weight of the polyurethane related to the first aspect of the present invention is adjusted according to the applications and does not require specific limitations; however, it is preferred to be 50,000-500,000, especially 100,000-300,000, of number average molecular weight (Mn) from standard polystyrene calculation measured by the GPC. If the molecular weight is smaller than aforementioned lower limit, enough strength and hardness may not be obtained, and if it is larger than aforementioned upper limit, deterioration of the handling properties such as processabilities tends to occur.

[Tensile Elongation at Break]

The tensile elongation at break of the polyurethane related to the first aspect of the present invention, using a strip sample of 10 mm in width, 100 mm in length, and approximately 50 to 100 μm in thickness, with 50 mm distance between chucks and tensile speed of 500 mm/min, measured at the temperature of 23° C., relative humidity 55%, has the lower limit that is typically 50%, preferably 100%, more preferably 150%, and the upper limit that is typically 400%, preferably 350%, more preferably 300%. If the tensile elongation at break is smaller than aforementioned lower limit, deterioration of the handling properties such as processabilities tends to occur, and if it is larger than aforementioned upper limit, enough strength and hardness may not be obtained.

[100% Modulus]

The 100% modulus of the polyurethane related to the first aspect of the present invention, using a sample strip of 10 mm in width, 100 mm in length, and approximately 50 to 100 μm in thickness, with 50 mm distance between chucks and tensile speed of 500 mm/min, measured at the temperature of 23° C., relative humidity 55%, has the lower limit that is typically 10 MPa or more, preferably 15 MPa or more, more preferably 20 MPa or more, and the upper limit that is typically 200 MPa or less, preferably 150 MPa or less, more preferably 100 MPa or less. If the 100% modulus is smaller than aforementioned lower limit, enough strength and hardness may not be obtained, and if it is larger than aforementioned upper limit, deterioration of the handling properties such as processabilities tends to occur.

[Creep Property]

The creep property $(((L-50)/50)\times 100(\%))$ of the polyurethane related to the first aspect of the present invention, using a sample prepared by creating a polyurethane film with 100 μm in thickness, cut it into a 10 mm-wide strip with marked reference line at every 50 mm, and measured the length of reference line (L mm) when 1 MPa of load onto the length direction has been applied for 16 hours and is removed, with constant temperature and humidity of 23° C./relative humidity 55% RH, does not have specific lower limit, although the lower is better, and is typically 5%, preferably 2%, more preferably 1%, and the upper limit is typically 20%, preferably 10%. If the creep property is smaller than aforementioned lower limit, the viscosity of polyurethane becomes high and the load of process may be increased, and if it is larger than aforementioned upper limit, enough strength and hardness may not be obtained.

[Hardness]

The polyurethane related to the first aspect of the present invention has characteristics that can obtain higher degree of hardness as it has a structure of higher rigidity (A). Specifically, for example, when a film sample with approximately 50-100 μm in thickness is fixed on the tester (II-type, Gakushin-Type), then perform the friction test for 500 reciprocations at 4.9 N load according to the JIS L 0849, the upper limit of the weight reduction ratio represented in ({(Sample weight before test−Sample weight after test)/ (Sample weight before test)}×100) is typically 2%, preferably 1.5%, more preferably 1.0%. Whereas, the upper limit of this weight reduction ratio is usually 0.1%, preferably 0.05%, more preferably 0.01%.

In addition, if it is represented in pencil hardness, that is measured according to the JIS K-5600-5-4 as a guideline, this film form sample typically has the hardness of 6B or more, preferably 4B or more, more preferably 3B or more.

[Applications]

The polyurethane related to the first aspect of the present invention can develop various characteristics and is available in broad applications such as the foam, elastomer, paint, fiber, adhesive, floor material, sealant, medical material, artificial leather, water-type polyurethane paint, etc.

Especially, when the high rigidity polyurethane related to the first aspect of the present invention is used in the applications such as artificial leather, synthetic leather, water-type polyurethane, adhesive, medical material, floor material, coatings, etc, because of its high ability in the friction resistance and blocking resistance abilities, it is not physically easily scratched, and it contribute the good surface characteristics that do not be deteriorated due to the friction.

The polyurethane related to the first aspect of the present invention can be used in the cast molding polyurethane elastomer. Specific applications include the rolls such as rolling mill roll, paper manufacture roll, office equipment, pre-tensioning roll, etc, the solid casters/tires of fork lift, motor vehicle new tram, trolley, lorry, etc, and the industrial product such as conveyor belt idler, guide roll, pulley, steel pipe lining, rubber screen for ore, gears, connecting rings, liner, impeller of pumps, cyclone cone, and cyclone liner, etc. In addition, a polyurethane related to the first aspect of the present invention can also be used in the belt of OA devices, paper feed roll, cleaning blade for copies, snow plow, toothed belt, surf roller, etc.

The polyurethane related to the first aspect of the present invention also is applied in the thermoplastic elastomer. For example, it can be used as the tubes and hoses used in the air pressure device for food and medical fields, painting equipment, analytical instrument, physical and chemical devices, quantitative pump, water treatment device, Industrial Robot, etc., the spiral tube, and the fire-fighting hoses. In addition, it is used in the various mechanism of transmission, spinning machine, packaging device, printing device, etc. as the belts such as round belt, V-belt, and flat belt. In addition, it also can be used in the heal top or sole of shoe, parts for devices such as coupling, packing, pole-joint, bush, gear, roll, etc, sports goods, leisure goods and belt for watches. Moreover, it also contains the automobile parts such as the oil stopper, gear box, spacer, chassis parts, interiors, tire-chain replacement product, etc. In addition, it can be used for the films such as the keyboard film and the automotive film, curl code, cable sheath, bellow, carrier belt, flexible container, binder, artificial leather, dipping product, adhesion, etc.

The polyurethane related to the first aspect of the present invention can be applied in the application of solvent-based two-component paint, and can be applied to the polyurethane related to the first aspect of the present invention can also be applied in the application as the woodworking products, including the musical instruments, family altar, furniture, decorated plywood board, sport gear, etc. And also be available in the automobile repairs as the tar-epoxy urethane.

The polyurethane related to the first aspect of the present invention can be used as a component such as the moisture-curing-type one-component paint, blocked isocyanate type solvent paint, alkyd resin paint, urethane modified synthetic resin paint, UV cure paint, water-based urethane paint, etc., and for example, it can be applied to the paint for the plastic bumper, strippable paint, coating agent for electromagnetic tape, floor tile, floor material, paper, overprint varnish for wooden printing films, varnish for woods, coil coating for high processing, optical fiber protection coating, solder resist, top coating for metal print, base coating for evaporation coating, white coating for canned food and so on.

The polyurethane related to the first aspect of the present invention can also be applied as adhesive in the use of food packaging, shoes, footwear, magnetic tape binder, decorative paper, wood, structural member, etc., and also be used as the component of the low temperature adhesive and hot-melt.

In the form of using the polyurethane related to the first aspect of the present invention as the adhesive, there are not specific limitations, therefore it is possible to use obtained polyurethane as the solvent adhesive by resolving into the solvent or as the hot-melt adhesive without using the solvent.

For the case that uses the solvent, there are no limitations regarding the solvents unless it is suitable for the characteristics of the urethane obtained, and both the water-based and organic-based solvent can be used. Especially, due to the reduction of the environmental loads, there are increasing demands for the water-based adhesives that are water-based polyurethane emulation is solved or dispersed into the water-based solvent, and the polyurethane related to the first aspect of the present invention is preferably suited used in that objective. Moreover, the adhesives that is produced from the polyurethane related to the first aspect of the present invention is able to mix the additives and auxiliaries used in the normal adhesives according to need without restriction. The examples of additives include pigment, anti-blocking agent, dispersion stabilizer, viscosity regulator, labeling agent, antigelling agent, light stabilizer, anti-oxidizing agent, ultraviolet absorber, heat resistance improver, inorganic or organic bulking agent, plasticizer, lubricant, antistatic agent, reinforcing material, catalyst, and a known method such as agitating and dispersion and so on as a method for adding these additives can be adopted.

The adhesives related to the first aspect of the present invention that is obtained by abovementioned method can effectively bond the metal materials such as iron, copper, aluminum, ferrite and coated plate, etc., and resin materials such as acrylate resin, polyester resin, ABS resin, polyamide resin, polycarbonate resin, vinyl chloride resin and the inorganic materials such as glass and ceramics, etc.

The polyurethane related to the first aspect of the present invention can be used, as binder, in the magnetic recording medium, inks, cast metals, burned brick, graft material, micro capsule, granulated fertilizer, granulated agrichemical, polymer cement mortar, resin mortar, rubber chip binder, recycle foam, glass fiber sizing, etc.

The polyurethane related to the first aspect of the present invention can be used, as a component of fiber-processing agent, in the process for giving shrink resistant, wrinkle-free, and water repellent, etc to the fiber.

When the polyurethane related to the first aspect of the present invention is used as the elastic fiber, the method of fibrillization of elastic fiber can be performed without particular limitations if fiber can be formed. For example, it is possible to employ the melt spinning method that is to pelletization once, then let them melt, then directly spin through the spinneret. If the elastic fiber is obtained from the polyurethane related to the first aspect of the present invention by the melt spinning, spinning temperature is preferably 250° C. or less, more preferably between 200° C. or more and 235° C. or less.

The polyurethane elastic fiber related to the first aspect of the present invention can be used as the bare yarn without modification or can be coated with the other fibers and be used as the coated yarn. Other fibers include the previously known fibers such as polyamide fiber, wool, cotton, polyester-fiber, etc., and especially, the polyester-fiber is preferably used in the present invention. In addition, the elastic fiber related to the first aspect of the present invention can contain the disperse dye of dyeing type.

The polyurethane related to the first aspect of the present invention can be used as the sealant caulking for concrete wall, inducing joint, frame and sash materials, wall type PC joint, ALC joint, boards joint, composite glass sealant, thermal-protection sash sealant, automobile sealant, etc.

The polyurethane related to the first aspect of the present invention can be used as the medical materials, including the blood compatible material such as tube, catheter, artificial heart, artificial blood vessel, artificial valve etc, as well as the disposable materials such as catheter, tube, bag, surgical gloves, artificial kidney potting material, etc.

The polyurethane related to the first aspect of the present invention, by terminal modifications, can be used as the raw materials for the UV curable paint, electron beam curable paint, photosensitive resin composition for flexographic printing plate, light curing type covering material composition for optical fiber, etc.

[Active-Energy Radiation Curable Polymer Composition]

An active-energy radiation curable polymer composition can be produced by using the polycarbonate diol related to the first aspect of the present invention.

The active-energy radiation curable polymer composition related to the first aspect of the present invention contains an urethane(meth)acrylate oligomer which is obtained from a raw material containing the polycarbonate diol related to the first aspect of the present invention, a polyisocyanate, and a hydroxyalkyl(meth)acrylate. Where, an optimum aspect as polyisocyanate, hydroxyalkyl(meth)acrylate, and the obtained-urethane (meth)acrylate oligomer is the same aspect as the active-energy radiation curable polymer composition related to the second aspect of the present invention to be discussed later.

[Active Energy Ray-Curable Polymer Composition]

Another aspect of the present invention is an active-energy radiation curable polymer composition. The active-energy radiation curable polymer composition related to the second aspect of the present invention contains an urethane (meth)acrylate oligomer. The urethane(meth)acrylate oligomer which is used by the second aspect of the present invention is a compound having one or more radical polymerizable (meth)acryloyl groups and at least two urethane bonds. The urethane (meth)acrylate oligomer is more excellent than other well-known active-energy radiation curable oligomer such as an epoxy(meth)acrylate-based oligomer, an acryl(meth)acrylate-based oligomer, etc. in that a cured material irradiated by the active energy ray has a well-balanced tensile strength and excellent tensile elongation, and its surface hardening is excellent as a composition, and scarcely leaving tackiness.

The urethane(meth)acrylate oligomer in the second aspect of the present invention is obtained from a raw material containing polyisocyanate, polycarbonate diol and hydroxyalkyl(meth)acrylate. The urethane(meth)acrylate oligomer can be either one type or two or more types.

The following describes each component of raw materials of the urethane(meth)acrylate oligomer.

(1) Polyisocyanate

A polyisocyanate constituting an urethane(meth)acrylate oligomer in the second aspect of the present invention is a compound having one or both of the substituent groups containing two or more isocyanate groups and isocyanate groups in one molecule (also referred as "isocyanate groups"). One type or two types or more polyisocyanate(s) is allowed. In one type of polyisocyanates, isocyanate groups may be either the same or different.

The substituent group containing isocyanate group includes alkyl group, alkenyl group, or alkoxyl group having 1 to 5 carbons, containing one or more isocyanate group(s), for example. The carbon number for the aforementioned alkyl group, etc. as a substituent group containing isocyanate group is preferred to be 1 to 3.

The number average molecular weight of the polyisocyanate is, in terms of balances between strength and elasticity as a cured material obtained by curing the active-energy radiation curable polymer composition, preferably 100 or more, more preferably 150 or more, while preferably 1,000 or less, and more preferably 500 or less.

The number average molecular weight of the polyisocyanate can be obtained by a calculated value from a chemical formula in case of a polyisocyanate comprising a single monomer, while a calculated value from NCO % in case of a polyisocyanate comprising two types or more monomers.

The aforementioned polyisocyanate includes an aliphatic polyisocyanate, a polyisocyanate having an alicyclic structure, and an aromatic polyisocyanate, for example.

The aliphatic polyisocyanate is a compound having an aliphatic structure and two or more isocyanate groups bonded thereto. The aliphatic polyisocyanate is preferred because it increases weather resistance and gives flexibility to the cured material obtained by curing the active-energy radiation curable polymer composition. The aliphatic structure in an aliphatic polyisocyanate is not specifically limited, but a straight- or branched-chain alkylene group having 1 to 6 carbons is preferred. Such an aliphatic polyisocyanate includes an aliphatic iisocyanate such as tetramethylene diisocyanate, hexamethylene diisocyanate, trimethyl hexamethylene diisocyanate, and dimer acid diisocyanate, and aliphatic triisocyanate such as tris(isocyanatehexyl) isocyanurate, for example.

The polyisocyanate is preferred to include a polyisocyanate having an alicyclic structure in terms of mechanical strength and it increases weather resistance and contamination resistance of a cured material obtained by curing the active-energy radiation curable polymer composition related to the second aspect of the present invention.

The polyisocyanate having an alicyclic structure is a compound having an aliphatic structure and two or more isocyanate groups bonded thereto. The alicyclic structure in a polyisocyanate having an alicyclic structure is not specifically limited, but a cycloalkylene group having 3 to 6 carbons is preferred. A polyisocyanate having an alicyclic structure includes diisocyanate having an alicyclic structure such as bis(isocyanatemethyl)cyclohexane, cyclohexanediisocyanate, bis(isocyanatecyclohexyl)metane, and isophorone diisocyanate, and triisocyanate having an alicyclic structure such as tris(isocyanateisophorone) isocyanurate.

A polyisocyanate having an alicyclic structure is preferred in terms of higher weather resistance of a cured material obtained by curing an active-energy radiation curable polymer composition, while a polyisocyanate having such an alicyclic structure includes bis(isocyanatemethyl)cyclohexane, cyclohexanediisocyanate, bis(isocyanatecyclohexyl)metane, and isophorone diisocyanate.

The aromatic polyisocyanate is a compound having an aromatic structure and two or more isocyanate groups bonded thereto. The aromatic structure in an aromatic polyisocyanate is not specifically limited, but divalent aromatic group having 6 to 13 carbons is preferred. Such an aromatic polyisocyanate includes aromatic series diisocyanate such as tolylenediisocyanate, xylylene diisocyanate, diphenylmethane diisocyanate, m-phenylenediisocyanate, and naphthalenediisocyanate, for example.

The aromatic polyisocyanate is preferred in terms of higher mechanical strength of the aforementioned cured material, for example, while such aromatic polyisocyanate includes tolylenediisocyanate and diphenylmethane diisocyanate.

(2) polycarbonate Diol

The polycarbonate diol constituting the urethane(meth)acrylate oligomer in the second aspect of the present invention is the same polycarbonate diol as the first aspect. However, when the polycarbonate diol related to the first aspect is applied as polycarbonate diol constituting the urethane(meth)acrylate oligomer related to the second aspect, the preferred range of the polycarbonate diol may be different from the preferred range of the polycarbonate diol alone related to the first aspect, while their differences are mainly discussed below.

The polycarbonate diol constituting the urethane(meth)acrylate oligomer in the second aspect of the present invention is a compound of which number average molecular weight is 500 or more and 5,000 or less, and includes 10 mass % or more of repeating unit represented by the following formula (A). The aforementioned polycarbonate diol has at least two hydroxyl groups in that molecular chain, or preferably each on both terminals of the molecular chain. The polycarbonate diol may be one type or two or more types.

[Chemical formula 4]

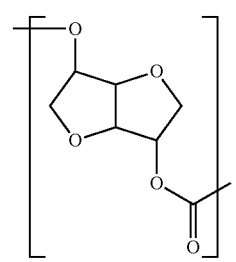

(A)

The structure other than the above Structure (A) is exemplified as a structure represented by the following formula (B) (hereinafter, a structure represented by the formula (B) may be referred to as "Structure (B)"), for example). The Structure (B) may be continuing in the aforementioned polycarbonate diol, may consist in regular intervals, or may be unevenly distributed.

[Chemical formula 5]

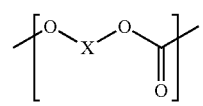

(B)

In formula (B), X represents a divalent group having 1 to 15 carbons which may contain hetero atom. This group may include a straight- or branched-chained chain group, ring group or any of these structures. A carbon number as an element constituting X is preferably 10 or less and more preferably 6 or less in terms of mechanical strength of the cured film to be obtained.

Specific examples of an X group include a group to be generated if a diol giving Structure (B) is used in producing the polycarbonate diol. The diol may be one type or two or more types. Such a diol includes a diol named at the first aspect.

X in formula (B) is preferred to be a divalent group having 6 carbons in terms of mechanical strength of a cured film to be obtained and industrial availability. Such an X includes an X derived from 1,6-hexanediol or 3-methyl-1,5-pentanediol as the aforementioned diol.

The amount of a structure other than the aforementioned structure (A) in the aforementioned polycarbonate diol may be in the range which can exhibit an effect by those other structures in addition to the effect of the present invention, so it can be decided arbitrarily according to those other structures.

The number average molecular weight of the aforementioned polycarbonate diol is 500 or more and 5,000 or less because the urethane(meth)acrylate oligomer has an appropriate viscosity and exhibits preferable workability, and in terms of mechanical strength and higher contamination resistance of the cured material obtained by curing the active-energy radiation curable polymer composition. The number average molecular weight of the aforementioned polycarbonate diol is preferably 3,000 or less, more preferably 2,000 or less and further preferably 1,500 or less. The number average molecular weight of the aforementioned polycarbonate diol is preferably 800 or more, and more preferably 1,000 or more in terms of the aforementioned points. When the number average molecular weight of the aforementioned polycarbonate diol is smaller, the aforementioned workability is enhanced, and mechanical strength and contamination resistance of the aforementioned cured material may be improved. When the number average molecular weight of the aforementioned polycarbonate diol is larger, a flexibility, which can follow transformation during 3D process of the aforementioned cured material, tends to be improved.

A hydroxyl value (OH value) of the aforementioned polycarbonate diol is preferred to be 20 mgKOH/g or more and 250 mgKOH/g or less in terms of mechanical strength and higher contamination resistance of a cured material obtained by curing the active-energy radiation curable polymer composition. The hydroxyl value (OH value) of the aforementioned polycarbonate diol is preferred to be 150 mgKOH/g or less in terms of the aforementioned points. The hydroxyl value of the aforementioned polycarbonate diol is preferably 35 mg/KOH/g or more, more preferably 55 mg/KOH/g or more and further preferably 75 mg/KOH/g or more in terms of the aforementioned points. When the hydroxyl value of the aforementioned polycarbonate diol is smaller, a flexibility, which can follow transformation during 3D process of the aforementioned cured material, tends to be improved. When the hydroxyl value of the aforementioned polycarbonate diol is larger, mechanical strength and contamination resistance of the aforementioned cured material tends to be improved. The hydroxyl value (OH value) of the aforementioned polycarbonate diol can be measured by the following method.

The average number of hydroxyl groups per molecule of the aforementioned polycarbonate diol is 2.2 or less in terms of gelation control in producing an urethane(meth)acrylate oligomer. The average number of hydroxyl groups per molecule of the aforementioned polycarbonate diol is preferred to be 2.1 or less in terms of the aforementioned points. When the average number of hydroxyl groups per molecule in the aforementioned polycarbonate diol exceeds the aforementioned upper limit, gelation occurs in producing urethane(meth)acrylate oligomer. Consequently, not only the urethane(meth)acrylate oligomer but also a reactor may be damaged and the obtained active-energy radiation curable polymer composition includes a gel and has higher viscosity and causes worse coating properties, which is not preferred. The average number of hydroxyl groups per molecule in the aforementioned polycarbonate diol is not limited, but is preferably 1.0 or more, more preferably 1.5 or more and further preferably 1.8 or more in order to maintain the molecular weight of the aforementioned urethane(meth) acrylate oligomer within a target range, and to make a well-balanced cured film obtained from an active-energy radiation curable polymer composition containing the aforementioned oligomer regarding a 3D processing characteristic and contamination resistance. When the average number of hydroxyl values per molecule in the aforementioned polycarbonate diol is lower than the aforementioned lower limit, the molecular weight tends not to be higher during a reaction with diisocyanate, while an urethane(meth)acrylate oligomer cannot have a target molecular weight, a well-balanced cured film cannot be obtained from the active-energy radiation curable polymer composition containing the aforementioned oligomer regarding a 3D processing characteristic and contamination resistance.

That is, the average number of hydroxyl groups per molecule in the aforementioned polycarbonate diol is preferably within 2.0±0.2, more preferably 2.0±0.1, and further preferably 2.0.

The average number of hydroxyl groups per molecule in the aforementioned polycarbonate diol can be calculated by the average number of molecular weight and a hydroxyl value which are obtained by the following method.

The aforementioned polycarbonate diol containing the aforementioned structure (A) can be produced by an esterification reaction of a diol component containing isosorbide, and its stereoisomers such as isomannide and isoidide and diester carbonate (3) Hydroxyalkyl(meth)acrylate The hydroxyalkyl(meth)acrylate constituting the urethane (meth)acrylate oligomer in the second aspect of the present invention is a compound having one or more hydroxyl group(s), one or more (meth)acryloyl group(s) and a hydrocarbon group having 1 to 30 carbons. The hydroxyalkyl (meth)acrylate may be one type or two or more types.

The aforementioned hydroxyalkyl(meth)acrylate may include 2-hydroxyethyl(meth)acrylate, 2-hydroxypropyl (meth)acrylate, 4-hydroxybutyl(meth)acrylate, 6-hydroxyhexyl(meth)acrylate, cyclohexanedimethanolmono(meth) acrylate, or a product of addition reaction of 2-hydroxyethyl (meth)acrylate with a caprolactone, a product of addition reaction of 4-hydroxybutyl(meth)acrylate with caprolactone, a product of addition reaction of glycidyl ether with (meth)acryl acid, mono(meth)acrylate form of glycol, pentaerythritoltri(meth)acrylate, and dipentaerythritolpenta(meth)acrylate.

Among the above, hydroxyalkyl(meth)acrylate having an alkylene group having 2-4 carbons between (meth)acryloyl group and hydroxyl group such as 2-hydroxyethyl(meth) acrylate, 2-hydroxypropyl(meth)acrylate, 4-hydroxybutyl (meth)acrylate is preferred in terms of mechanical strength of the obtained cured film.

The molecular weight of the aforementioned hydroxyalkyl(meth)acrylate is preferred to be 40 or more, and more preferred to be 80 or more, while in terms of mechanical strength of the obtained cured film, 800 or less is preferred and 400 or less is further preferred. If the aforementioned hydroxyalkyl(meth)acrylate is a product of the aforementioned addition reaction or a polymer, the aforementioned molecular weight means a number average molecular weight.

(4) Others

The urethane(meth)acrylate oligomer in the second aspect of the present invention may contain other components in its raw material as long as effects of the present invention can be obtained. Those other components include a high molecular weight polyol of which number average molecular weight is over 500 excluding the polycarbonate diol containing the aforementioned structure (A), and a low molecular weight polyol of which number average molecular weight is 500 or less, and a chain extender.

The aforementioned high molecular weight polyol is a compound of which number average molecular weight is over 500 and contains two or more hydroxyl groups (excluding the polycarbonate diol containing the aforementioned structure (A)). The aforementioned high molecular weight polyol may be one type or two or more types. Those high molecular weight polyols include polyether diol, polyesterdiol, polyether ester diol, and the polycarbonate diol other than the polycarbonate diol including the aforementioned structure (A), polyolefin polyol and silicone polyol.

The aforementioned polyether diol includes a compound which can be obtained by ring-opening polymerization of cyclic ether, such as polyethylene glycol, polypropylene glycol, and polytetramethylene glycol.

The aforementioned polyester diol includes a compound which can be obtained by polycondensation of dicarboxylic acid or its anhydride and low-molecular weight diol, such as polyethylene adipate, polypropylene adipate, polybutylene adipate, polyhexamethylene adipate, and polybutylene sebacate. The aforementioned ester diol includes a compound which can be obtained by polycondensation of lactone with low-molecular weight diol such as polycaprolactone and polymethyl valerolactone. The aforementioned dicarboxylic acid includes succinic acid, glutaric acid, adipic acid, pimelic acid, suberic acid, azelaic acid, sebacic acid, and phthalic acid, while anhydride of the dicarboxylic acid includes those anhydrides, for example, the aforementioned low-molecular weight diol includes ethylene glycol, diethylene glycol, triethylene glycol, propylene glycol, dipropylene glycol, 1,2-butanediol, 1,3-butanediol, 1,4-butanediol, polytetramethyleneglycol, 1,5-pentanediol, 1,6-hexanediol, 3-methyl-1,5-pentanediol, neopentyl glycol, 2-ethyl-1,3-hexane glycol, 2,2,4-trimethyl-1,3-pentanediol, 3,3-dimethylol heptane, 1,9-nonanediol, 2-methyl-1,8-octanediol, cyclohexanedimethanol, and bishydroxyethoxy benzene.

The aforementioned polyether ester diol includes a compound obtained by ring-opening polymerization of a cyclic ether with the aforementioned polyester diol, and a compound obtained by polycondensation of the aforementioned polyether diol and the aforementioned dicarboxylic acid such as poly(polytetramethylene ether) adipate.

The aforementioned other polycarbonate diol includes polybutylene carbonate, a polyhexamethylene carbonate, poly(3-methyl-1,5-pentylene)carbonate, etc. and those copolymers which are obtained by removing glycol or alcohol from the aforementioned low-molecular weight diol and alkylene carbonate or dialkyl carbonate.

The aforementioned polyolefin polyol is polyolefin having two or more hydroxyl groups. The aforementioned polyolefin polyol may be one type or two or more types. The aforementioned polyolefin polyol includes poly butadiene polyol, hydrogenated polybutadiene polyol, and polyisoprene polyol, for example.

The aforementioned silicone polyol is silicone having two or more hydroxyl groups. The aforementioned silicone polyol may be one type or two or more types. The aforementioned silicone polyol includes polydimethylsiloxane polyol.

Among them, the aforementioned high-molecular weight polyol is preferred to be the aforementioned other polycarbonate diol in terms of higher weather resistance and mechanical strength of the cured material obtained by curing the active-energy radiation curable polymer composition.

When the number average molecular weight of the other aforementioned polycarbonate diol is small, viscosity of the urethane(meth)acrylate oligomer is not significantly increased and its workability is favorable, while higher weather resistance and higher mechanical strength of the cured material obtained by curing the active-energy radiation curable polymer composition can be expected. Because of these points, the number average molecular weight of the aforementioned other polycarbonate diol is preferably 10,000 or less, more preferably 5,000 or less and further preferably 2,000 or less.

The aforementioned low molecular weight polyol is a compound of which number average molecular weight is 500 or less and contains two or more hydroxyl groups (excluding the polycarbonate diol containing the aforementioned structure (A)). The aforementioned low molecular weight polyol may be one type or two or more types. These low molecular weight polyols include aliphatic diol such as ethylene glycol, diethylene glycol, triethylene glycol, propylene glycol, dipropylene glycol, 1,2-propane diol, 1,3-propane diol, 2-methyl-1,3-propane diol, neopentyl glycol, 1,2-butane diol, 1,3-butane diol, 1,4-butane diol, 1,5-pentane diol, 2-methyl-1,5-pentanediol, 3-methyl-1,5-pentane diol, 2,2,4-trimethyl-1,5-pentane diol, 2,3,5-trimethyl-1,5-pentanediol, 1,6-hexanediol, 2-ethyl-1,6-hexanediol, 2,2,4-trimethyl-1,6-hexanediol, 3,3-dimethylol heptane, 1,8-octanediol, 2-methyl-1,8-octane diol, and 1,9-nonanediol; alicyclic diol such as cyclopropane diol, cyclopropane dimethanol, cyclopropane diethanol, cyclopropane dipropanol, cyclopropane dibutanol, cyclopentane diol, cyclopentane dimethanol, cyclopentane diethanol, cyclopentane dipropanol, cyclopentane dibutanol, cyclohexanediol, cyclohexane dimethanol, cyclohexane diethanol, cyclohexane dipropanol, cyclohexane dibutanol, cyclohexene diol, cyclohexene dimethanol, cyclohexene diethanol, cyclohexene dipropanol, cyclohexene dibutanol, cyclohexadiene diol, cyclohexadiene dimethanol, cyclohexadiene diethanol, cyclohexadiene dipropanol, cyclohexadiene dibutanol, hydrogenated bisphenol A, tricyclodecane diol, and adamantyl diol; aromatic series-based diol such as bishydroxyethoxy benzene, bishydroxyethyl terephthalate, and bisphenol-A; dialkanol amine such as N-methyldiethanolamine; pentaerythritol; sorbitol; mannitol; glycerin; and trimethylolpropane.

Among them, the aforementioned low-molecular weight polyol is preferred to be aliphatic dial or alicyclic dial in terms of the weather resistance of the cured film to be obtained. In particular, for applications where mechanical strength of the cured film is required, the aforementioned low-molecular weight polyol is especially preferred to be polyol having 1-4 carbons between hydroxyl groups such as ethylene glycol, propylene glycol, 1,2-propanediol, 1,3-propanediol, 2-methyl-1,3-propanediol, neopentyl glycol, 1,2-butanediol, 1,3-butanediol, and 1,4-butanediol; and alicyclic polyol where two hydroxyl groups symmetrically exist against alicyclic structure such as 1,4-cyclohexanedimethanol, and hydrogenated bisphenol-A.

The number average molecular weight of the aforementioned low-molecular weight polyol is, in terms of balances between elongation and elasticity as the cured material obtained by curing the active-energy radiation curable polymer composition, preferably 50 or more, while preferably 250 or less, and more preferably 150 or less.

The aforementioned chain extender is a compound having two or more active hydrogens which react with isocyanate group. The chain extender may be one type or two or more types. Such a chain extender includes a low-molecular weight diamine compound of which number average molecular weight is 500 or less for example, aromatic series diamine such as 2,4- or 2,6-tolylene diamine, xylylene diamine, and 4,4'-diphenylmethane diamine; aliphatic diamine such as ethylene diamine, 1,2-propylene diamine, 1,6-hexane diamine, 2,2-dimethyl-1,3-propane diamine, 2-methyl-1,5-pentane diamine, 2,2,4- or 2,4,4-trimethyl hexane diamine, 2-butyl-2-ethyl-1,5-pentane diamine, 1,8-octane diamine, 1,9-nonane diamine, and 1,10-decane diamine; and alicyclic diamine such as 1-amino-3-aminoethyl-3,5,5-trimethyl cyclohexane (IPDA), 4,4'-dicyclohexylmethane diamine (hydrogenated MDA), isopropylidenecyclohexyl-4,4'-diamine, 1,4-diaminocyclohexane, 1,3-bisaminomethylcyclohexane, and tricyclodecanediamine.

The molecular weight or the number average molecular weight of the aforementioned raw material compound such as the polycarbonate diol containing the aforementioned structure (A) can be calculated by the gel permeation chromatography (hereinafter, referred as "GPC"), while the molecular weight of a compound other than a polyol having the molecular weight distribution can be calculated by a chemical formula or the number average molecular weight can be obtained by GPC. The number average molecular weight of a polyol having the molecular weight distribution at GPC can also be calculated by OH value.

[Calculation of the Number Average Molecular Weight by GPC]

By using GPC ("HLC-8120 GPC" made by TOSOH Corporation), a tetrahydrofuran is used as a solvent, a polystyrene as a standard sample, and TSK gel superH1000+H2000+H3000 as a column to measure its number average molecular weight at solution sending speed at 0.5 cm$^3$/min. and the column oven temperature at 40° C.

[Calculation of the Number Average Molecular Weight of Polyisocyanate by NCO %]

1 g of polyisocyanate and 20 mL of 0.5 mol/litter dibutylamine toluene solution is stored in an Erlenmeyer flask, diluted by 100 mL of acetone to react at 25° C. for 30 min. Then, it is titrated by 0.5 mol/litter hydrochloric acid solution. The titration same as abovementioned is performed to obtain a blank value, unless the polyisocyanate was not injected into an Erlenmeyer flask. Then NCO % and the number average molecular weight are calculated by the following formula.

NCO %=$B1$−$A1$)×0.5×42.02)/(1×1000)×100

A1: The amount of hydrochloric acid solution required for titrating a solution containing polyisocyanate (mL)
B1: The amount of hydrochloric acid solution required for titrating a blank solution which does not contain polyisocyanate (mL)
The number average molecular weight of polyisocyanate= (42.02/NCO %)×the number of NCO groups contained in one molecule polyisocyanate

[Calculation by OH Value of the Number Average Molecular Weight of Polyol]

Two gram (2 g) of polyol and 0.5 mol/litter pyridine solution of phthalic anhydride are stored in an Erlenmeyer flask to react at 100° C. for 2 hours, then diluted by 150 mL of acetone. Then, it is titrated by 0.5 mol/litter aqueous sodium hydroxide. The titration same as abovementioned is performed to obtain a blank value, unless the polyol was not injected into an Erlenmeyer flask. Then OH value and the number average molecular weight are calculated by the following formula.

OH value={($B2$−$A2$)×0.5×56.11×1000}/(2×1000)

A2: The amount of aqueous sodium hydroxide required for titrating a solution containing a polyol (mL)
B2: The amount of aqueous sodium hydroxide required for titrating a blank solution which does not contain a polyol (mL)
The number average molecular weight of polyol={(56.11×1000)/OH value}×the number of functional groups In the aforementioned formula, "the number of functional groups" indicates the number of OH groups which are contained in one molecule polyol.

The amount of all isocyanate groups and the amount of all functional groups to react with the isocyanate group such as hydroxyl group and amino group in the urethane(meth)acrylate oligomer related to the second aspect of the present invention are usually equivalent mol theoretically and represented by mol %.

Therefore, the amount of the aforementioned polyisocyanate, polycarbonate diol, hydroxyalkyl(meth)acrylate, and other raw material compounds in the aforementioned urethane(meth)acrylate oligomer is the amount in which the amount of all isocyanate groups and the amount of all functional groups to react them in the urethane(meth)acrylate oligomer are the equivalent mol, or 50 to 200 mol % by the functional groups relative to the isocyanate groups.

In producing the urethane(meth)acrylate oligomer, the amount of hydroxyalkyl(meth)acrylate is usually 10 mol % or more, preferably 15 mol % or more, more preferably 25 mol % or more, or usually 70 mol % or less, and preferably 50 mol % or less relative to the total amount of compounds containing a functional group to react with isocyanate such as hydroxyalkyl(meth)acrylate, the aforementioned polycarbonate diol, the aforementioned high-molecular weight polyol, the aforementioned low-molecular weight polyol, and a chain extender. According to this proportion, the molecular weight of the obtained urethane(meth)acrylate oligomer can be controlled. With higher hydroxyalkyl(meth)acrylate proportion, the molecular weight of urethane(meth)acrylate oligomer tends to be small, while with lower proportion the molecular weight tends to be large.

Relative to the total amount of the aforementioned polycarbonate diol and the aforementioned high-molecular weight polyol, the amount of the aforementioned polycarbonate diol is preferably 25 mol % or more, more preferably 50 mol % or more and further preferably 70 mol % or more. When the amount of the aforementioned polycarbonate diol is larger than the aforementioned lower limit, hardness and contamination resistance of the cured material tends to be excellent, which is preferred.

In addition, relative to the total amount of the aforementioned polycarbonate diol, the aforementioned high-molecular weight polyol, and the aforementioned low-molecular weight polyol, the amount of the aforementioned polycarbonate diol is preferably 25 mol % or more, more preferably 50 mol % or more and further preferably 70 of % or more. When the amount of the aforementioned polycarbonate diol is larger than the aforementioned lower limit, elongation and weather resistance of the cured material tends to be improved, which is preferred.

If an urethane(meth)acrylate oligomer is a compound containing a chain extender, the amount of all polyols relative to the total amount of compounds of the aforementioned polycarbonate diol, the aforementioned high-molecular weight polyol, the aforementioned low-molecular weight polyol, and the chain extender is preferably 70 mol %- or more, more preferably 80 mol % or more, further preferably 90 mol % or more, and especially preferably 95 mol % or more. When the aforementioned amount of all polyols is larger than the lower limit, its solution stability tends to be improved, which is favorable.

In the active-energy radiation curable polymer composition related to the second aspect of the present invention, the calculated crosslinking points molecular weight of the composition is preferred to be 500 to 10,000.

In the present specification, the calculated crosslinking points molecular weight of a composition represents an average value of the molecular weight among an active energy ray reactive group forming a network structure among all compositions (hereinafter, may be referred as "crosslinking point"). This molecular weight between calculated network crosslinking point correlates with network planar dimension in forming a network structure, while with larger calculated crosslinking points molecular weight, its crosslinking density becomes small. In an active energy ray curing reaction, when a compound having only one active energy ray reactive group (hereinafter, may be referred as "monofunctional compound") is reacted, a linear polymer molecule is generated, while a compound having two or more active energy ray reactive group (hereinafter, may be referred as "multifunctional compound") is reacted, a network structure is formed.

Therefore, an active energy ray reactive group owned by a multifunctional compound is a crosslinking point, the calculated crosslinking points molecular weight is calculated mainly by a multifunctional compound having the crosslinking points. Then, a monofunctional compound is treated as exhibiting an effect for extending the molecular weight among crosslinking points obtained by the multifunctional compound to calculate the calculated crosslinking points molecular weight. In addition, the calculated crosslinking points molecular weight is calculated, assuming that all active energy ray reactive group has the same reactivity, and all active energy ray reactive groups react when the active energy ray is irradiated.

In a multifunctional compound of single system composition in which only one type of multifunctional compound reacts, two times of the average molecular weight per one active energy ray reactive group owned by a multifunctional compound is the calculated crosslinking points molecular weight. For example, a bifunctional compound of the molecular weight 1,000 is (1000/2)×2=1000, while a trifunctional compound of the molecular weight 300 is (300/3)×2=200.

In a multifunctional compound combined composition in which multiple types of multifunctional compounds react, average value of respective calculated crosslinking points molecular weight of the above single system against the number of all active energy ray reactive groups contained in the composition is to be the calculated crosslinking points molecular weight of the composition. For example, in a composition comprising a mixture of 4 mols of a bifunctional compound of the molecular weight 1,000 and 4 mols of a trifunctional compound of the molecular weight 300, the number of all active energy ray reactive groups in the composition is 2×4+3×4=20, and the calculated crosslinking points molecular weight is {(1000/2)×8+(300/3)×12}×2/20=520.

When a monofunctional compound is included in a composition, computationally assuming that reaction is made in a position of the center of the molecular chain formed by linking each equivalent mol to active energy ray reactive group of a multifunctional compound (that is a crosslinking point) and linking monofunctional compound to the crosslinking point, the extended length of the molecular chain by a monofunctional compound at one crosslinking point is half of the value obtained by dividing the total molecular weight of monofunctional compounds by the number of all active energy ray reactive groups in multifunctional compounds in the composition. Here, the molecular weight between calculated network cross-linking points is considered to be twice the average molecular weight per one crosslinking point, so the length extended by a monofunctional compound against the calculated crosslinking points molecular weight calculated for a multifunctional compound is the value obtained by dividing the total molecular weight of the monofunctional compounds by the number of all active energy ray reactive group of the multifunctional compound in the composition.

For example, in a composition comprising a mixture of 40 mols of a monofunctional compound of the molecular weight 100 and 4 mols of a bifunctional compound of the molecular weight 1,000, the number of active energy ray reactive groups of the multifunctional compound is 2×4=8, and the extended length by the monofunctional compound in the calculated crosslinking points molecular weight is 100× 40/8=500. That is, the calculated crosslinking points molecular weight of the composition is 1000+500=1500.

Because of these, in a mixture in which a monofunctional compound $M_A$ mol of the molecular weight $W_A$, $f_B$-functional compound $M_B$ mol of the molecular weight $W_B$, and $f_C$-functional compound $M_C$ mol of the molecular weight $W_C$, the calculated crosslinking points molecular weight of the composition can be represented by the following formula:

$$\frac{\left(\frac{W_A M_A}{f_B M_B + f_C M_C} + \frac{2W_B}{f_B}\right) \times f_B M_B + \left(\frac{W_A M_A}{f_B M_B + f_C M_C} + \frac{2W_C}{f_C}\right) \times f_C M_C}{f_B M_B + f_C M_C} = \quad \text{[Mathematical formula 3]}$$

$$\frac{W_A M_A + 2W_B M_B + 2W_C M_C}{f_B M_B + f_C M_C}$$

The calculated crosslinking points molecular weight of the active-energy radiation curable polymer composition related to the second aspect of the present invention is preferably 500 or more, more preferably 800 or more, and further preferably 1,000 or more, while preferably 10,000 or less, more preferably 8,000 or less, further preferably 6,000 or less, much further preferably 4,000 or less, and specially preferably 3,000 or less.

When the calculated crosslinking points molecular weight is 10,000 or less, contamination resistance of the cured film obtained by the composition is excellent, and tends to be well-balanced between 3D processing suitability and contamination resistance, which is favorable. When the calculated crosslinking points molecular weight is 500 or more, 3D processing suitability of the obtained cured film is excellent, and tends to be well-balanced between 3D processing suitability and contamination resistance, which is favorable. This is speculated because the 3D processing suitability and contamination resistance tend to depend on the distance between crosslinking points in the network structure, while with the longer distance, the structure is flexible and easy to be extended, which is good at 3D processing suitability, and with the shorter distance the network structure is rigid and good at contamination resistance.

The urethane(meth)acrylate oligomer related to the second aspect of the present invention can be produced by addition reacting the aforementioned polycarbonate diol containing Structure (A) and the aforementioned hydroxyalkyl(meth)acrylate to the aforementioned polyisocyanate. Here, when the aforementioned high-molecular weight polyol, the aforementioned low-molecular weight polyol, and the aforementioned chain extender, etc. are used together as its raw material, the urethane(meth)acrylate oligomer related to the second aspect of the present invention can be produced by addition reacting the other aforementioned raw material compounds to the aforementioned polyisocyanate. This addition reaction can be conducted by any known method. These methods include the following (1) to (3) approaches.

(1) A prepolymer method, in which isocyanate terminal urethane prepolymer is obtained by reacting components other than the aforementioned hydroxyalkyl(meth)acrylate under a excess isocyanate group condition, then the isocyanate terminal urethane prepolymer is reacted by the aforementioned hydroxyalkyl(meth)acrylate.

(2) One-shot method, in which all components are added together and reacted together.

(3) A method, in which the aforementioned polyisocyanate and the aforementioned hydroxyalkyl(meth)acrylate are reacted at first to synthesize a urethane(meth)acrylate a prepolymer having a (meth)acryloyl group and isocyanate group in a molecule together, and then the other raw material components are reacted with the obtained prepolymer.

Among them, the method (1) is preferred because the aforementioned urethane prepolymer is obtained by urethanizing the aforementioned polyisocyanate and the aforementioned polycarbonate diol, and the aforementioned urethane (meth)acrylate oligomer has a structure which is obtained by urethanizing a urethane prepolymer having isocyanate groups at terminals and the aforementioned hydroxyalkyl (meth)acrylate, so the molecular weight can be controlled and acryloyl groups can be introduced to both terminals.

In producing the urethane(meth)acrylate oligomer, a solvent may be used to adjust viscosity. One type or two or more types of solvents can be used and any known solvent can be used as far as effects of the present invention can be obtained. Preferable solvents include toluene, xylene, ethyl acetate, butyl acetate, cyclohexane, methylethylketone, and methylisobutylketone. Less than 300 parts by mass of the solvent can be usually used relative to 100 parts by mass of the active-energy radiation curable polymer composition.

In producing the urethane(meth)acrylate oligomer, the total amount of the aforementioned urethane(meth)acrylate oligomer and its raw material is preferred to be 20 mass % or more relative to the total amount, and more preferred to be 40 mass % or more. The upper limit of this total amount is 100 mass %. When the total amount of the urethane(meth) acrylate oligomer and its raw material is 20 mass % or more, its reaction speed gets higher and its producing efficiency tends to be improved, which is preferred.

In producing the urethane(meth)acrylate oligomer, the reaction temperature is usually 20° C. or more, preferably 40° C. or more, and more preferably 60° C. or more. When the reaction temperature is 20° C. or more, its reaction speed gets higher and its producing efficiency tends to be improved, which is preferred. Further it is usually 120° C. or less and preferably 100° C. or less. When the reaction temperature is 120° C. or less, a side reaction such as allophanate reaction can be suppressed, which is preferred. When a solvent is included in a reaction solution, a temperature below the boiling point of that solvent is preferred, and when (meth)acrylate is contained, 70° C. or less is preferred in terms of prevention of reaction of (meth) acryloyl group. The reaction time is usually about 5 to 20 hours.

A catalyst for addition reaction in producing an urethane (meth)acrylate oligomer can be selected from the range which an effect of the present invention can be obtained, and includes dibutyltin laurate, dibutyltin dioctoate, dioctyltin dilaurate, and dioctyltin dioctoate. The addition reaction catalyst may be one type or two or more types. The addition reaction catalyst is preferred to be the dioctyltin dilaurate among them in terms of environmental adaptability, catalyst activity and preservation stability.

In producing the urethane(meth)acrylate oligomer, if (meth)acryloyl group is included in its reactive solution, a polymerization inhibitor can be used together. Such a polymerization inhibitor can be selected from the range in which an effect of the present invention can be obtained, and includes phenols such as hydroquinone, hydroquinone monoethyl ether, and dibutylhydroxy toluene, amines such as phenothiazine, and diphenylamine, dibutyl dithiocarbamate, copper salt such as copper, manganese salt such as manganic acetate, nitro compound, and nitroso compound. The polymerization inhibitor may be one type or two or more types. Phenols is preferred among them as the polymerization inhibitor.

Preparation ratio of each raw material component is substantially equal to the urethane(meth)acrylate oligomer composition related to the second aspect of the above present invention. Preparation ratio of each raw material component is the same as the urethane(meth)acrylate oligomer composition related to the second aspect of the above present invention, for example.

The active-energy radiation curable polymer composition related to the second aspect of the present invention may contain other components other than the aforementioned urethane(meth)acrylate oligomer as long as an effect of the present invention can be obtained. Those other components include an active energy ray reactive monomer, an active energy ray curable oligomer, a polymerization initiator, a photosensitization agent, addition agent, and a solvent.

In the active-energy radiation curable polymer composition related to the second aspect of the present invention, the amount of the aforementioned urethane(meth)acrylate oligomer is preferably 40 mass % or more and more preferably 60 mass % or more, relative to the total amount of active energy ray reactive components containing the aforementioned urethane(meth)acrylate oligomer. The upper limit of this amount is 100 mass %. When the contained urethane (meth)acrylate oligomer amount is 40 mass % or more, an excellent hardness can be obtained, its mechanical strength as a cured material is not too high, and its 3D processing suitability tends to improve, which is preferable.

In the active-energy radiation curable polymer composition related to the second aspect of the present invention, the larger amount of the aforementioned urethane(meth)acrylate oligomer is preferred in terms of elongation and film making property, while the smaller amount is preferred in terms of lower viscosity. From these points of view, the amount of the aforementioned urethane(meth)acrylate oligomer is preferably 50 mass % or more, and more preferably 70 mass or more, relative to the total amount of all components containing other components in addition to the aforementioned active energy ray reactive components. The upper limit of the aforementioned urethane(meth)acrylate oligomer is 100 mass %, and the aforementioned amount is preferred to be lower than that amount.

In the active-energy radiation curable polymer composition related to the second aspect of the present invention, the total amount of the aforementioned active energy ray reactive components containing the aforementioned urethane (meth)acrylate oligomer is preferably 60 mass % or more, more preferably 80 mass % or more, further preferably 90 mass % or more, and much further preferably 95 mass % or more relative to the total amount of the composition in terms of excellent curing speed and surface curing as a composition and tackiness scarcely left. The upper limit of the aforementioned amount is 100 mass %.

As the aforementioned energy ray reactive monomer, any known active energy reactive monomer can also be used as long as an effect of the present invention can be obtained. Such an active energy reactive monomer can be used in order to adjust hydrophobic properties of the urethane(meth) acrylate oligomer and physical properties such as hardness and elongation of a cured material when the obtained composition is made to be the cured material. The active energy ray reactive monomer can be one type or two or more types.

These active energy ray reactive monomers include vinyl ethers, (meth)acrylamides, and (meth)acrylates for example, and specifically aromatic vinyl monomers such as styrene, α-methylstyrene, α-chrolostyrene, vinyl toluene, and divinyl benzene; vinyl ester monomers such as vinyl acetate, vinyl butyrate, N-vinyl formamide, N-vinyl acetamide, N-vinyl-2-pyrolidone, N-vinyl caprolactam, and adipic acid divinyl; vinyl ethers such as ethyl vinyl ether, phenyl vinyl ether; allyl compounds such as diallyl phthalate, trimethylolpropane diallyl ether, allyl glycidyl ether; (meth)acrylamides such as acrylamide, N,N-dimethyl acrylamide, N,N-dimethyl methacrylamide, N-methylolacrylamide, N-methoxymethylacrylamide, N-butoxymethylacrylamide, N-t-butylacrylamide, acryloylmorpholine, methylenebisacrylamide; monofunctional (meth)acrylate such as (meth) acrylic acid, methyl(meth)acrylate, ethyl(meth)acrylate, propyl(meth)acrylate, n-butyl-(meth)acrylate, i-butyl-(meth)acrylate, t-butyl-(meth)acrylate, hexyl(meth)acrylate, 2-ethylhexyl-(meth)acrylate, lauryl(meth)acrylate, stearyl (meth)acrylate, tetrahydrofurfuryl(meth)acrylate, morpholyl (meth)acrylate, 2-hydroxyethyl-(meth)acrylate, 2-hydroxypropyl-(meth)acrylate, 4-hydroxybutyl-(meth)acrylate, glycidyl(meth)acrylate, dimethylaminoethyl(meth)acrylate, diethylaminoethyl(meth)acrylate, benzyl(meth)acrylate, cyclohexyl(meth)acrylate, phenoxyethyl(meth)acrylate, tricyclodecane(meth)acrylate, dicyclopentenyl(meth)acrylate, dicyclopentenyloxyethyl(meth)acrylate, dicyclopentanyl (meth)acrylate, allyl(meth)acrylate, 2-ethoxyethyl(meth) acrylate, isobornyl(meth)acrylate, (meth)acrylate phenyl; and multifunctional (meth)acrylate such as ethylene glycol di(meth)acrylate, diethylene glycol di(meth)acrylate, triethylene glycol di(meth)acrylate, tetraethylene glycol di(meth) acrylate, polyethylene glycol di(meth)acrylate (n=5 to 14), propylene glycol di(meth)acrylate, dipropylene glycol di(meth)acrylate, tripropylene glycol di(meth)acrylate, tetrapropylene glycol di(meth)acrylate, polypropylene glycol di(meth)acrylate (n=5 to 14), 1,3-butylene glycol-di(meth) acrylate, 1,4-butanediol-di(meth)acrylate, polybutylene glycol di(meth)acrylate (n=3 to 16), poly(1-methyl butylene glycol) di(meth)acrylate (n=5 to 20), 1,6-hexanediol di(meth)acrylate, 1,9-nonanediol di(meth)acrylate, neopentyl glycol di(meth)acrylate, hydroxypivalic acid neopentyl glycol di(meth)acrylate ester, dicyclopentane diol di(meth)acrylate, tricyclodecane di(meth)acrylate, trimethylolpropane tri (meth)acrylate, pentaerythritol tri(meth)acrylate, pentaerythritol tetra(meth)acrylate, ditrimethylolpropane tetra (meth)acrylate, dipentaerythritol tetra(meth)acrylate, dipentaerythritol penta(meth)acrylate, dipentaerythritol hexa(meth)acrylate, trimethylolpropane trioxyethyl(meth)acrylate, trimethylolpropane trioxypropyl(meth)acrylate, trimethylolpropane polyoxyethyl(meth)acrylate, trimethylolpropane polyoxypropyl(meth)acrylate, tris(2-hydroxyethyl) isocyanurate tri(meth)acrylate, tris(2-hydroxyethyl) isocyanurate di(meth)acrylate, ethylene oxide adduct bisphenol A di(meth)acrylate, ethylene oxide adduct bisphenol F di(meth)acrylate, propylene oxide adduct bisphenol A di(meth)acrylate, propylene oxide adduct bisphenol F di(meth)acrylate, tricyclodecane dimethanol di(meth)acrylate, bisphenol A epoxy di(meth)acrylate, and bisphenol F epoxy di(meth)acrylate.

Among them, for an application in which coating properties are required in a composition related to the second aspect of the present invention, monofunctional (meth) acrylate having ring structure in its molecule is preferred such as (meth)acryloylmorpholine, tetrahydrofurfuryl(meth) acrylate, benzyl(meth)acrylate, cyclohexyl(meth)acrylate, trimethylcyclohexyl(meth)acrylate, phenoxyethyl(meth) acrylate, tricyclodecane(meth)acrylate, dicyclopentenyl (meth)acrylate, isobornyl(meth)acrylate, and mono(meth) acrylamide, while for an application in which mechanical strength is required for the obtained cured material, multifunctional (meth)acrylate such as 1,4-butanediol-di(meth) acrylate, 1,6-hexanediol di(meth)acrylate, 1,9-nonanediol di(meth)acrylate, neopentyl glycol di(meth)acrylate, tricyclodecane di(meth)acrylate, trimethylolpropane tri(meth) acrylate, pentaerythritol tri(meth)acrylate, pentaerythritol tetra(meth)acrylate, dipentaerythritol tetra(meth)acrylate, dipentaerythritol penta(meth)acrylate, and dipentaerythritol hexa(meth)acrylate are preferred.

In an active-energy radiation curable polymer composition related to the second aspect of the present invention, the amount of the aforementioned active energy ray reactive monomer is preferred to be 50 mass % or less, more preferably 30 mass % or less, further preferably 20 mass % or less, and specially further preferably 10 mass % or less relative to the total amount of the composition in terms of physical properties adjustment such as viscosity adjustment of the composition, hardness and elongation of the cured material.

The aforementioned active energy ray curable oligomer can be one type or two or more types. The aforementioned active energy ray curable oligomer includes epoxy(meth) acrylate oligomer and acrylic (meth)acrylate oligomer.

In an active-energy radiation curable polymer composition related to the second aspect of the present invention, the amount of the aforementioned active energy ray reactive oligomer is preferred to be 50 mass % or less, more preferably 30 mass % or less, further preferably 20 mass % or less, and specially further preferably 10 mass % or less relative to the total amount of the composition in terms of physical properties adjustment such as hardness and elongation of the cured material.

The aforementioned polymerization initiator is used mainly to improve the initiation efficiency of polymerization reaction which progresses by irradiation of an active energy ray such as ultraviolet ray and electron ray. As a polymerization initiator, an optical radical polymerization initiator which is a compound which produces a radical by the light, is common, and any known optical radical polymerization initiator is allowed as long as an effect of the present invention can be obtained. The optical radical polymerization initiator may be one type or two or more types. The optical radical polymerization initiator can be used with a photosensitization agent.

An optical radical polymerization initiator includes benzophenone, 2,4,6-trimethyl benzophenone, 4,4-bis(diethylamino)benzophenone, 4-phenyl benzophenone, methylorthobenzoyl benzoate, thioxanthone, diethylthioxanthone, isopropyl thioxanthone, chlorothioxanthone, 2-ethyl anthraquinone, t-butyl anthraquinone, diethoxy acetophenone, 2-hydroxy-2-methyl-1-phenylpropane-1-on, benzyl dimethylketal, 1-hydroxy cyclohexylphenyl ketone, benzoin methyl ether, benzoin ethyl ether, benzoin isopropyl ether, benzoin isobutyl ether, methylbenzoyl formate, 2-methyl-1-

{4-(methylthio)phenyl}-2-morpholinopropane-1-on, 2,6-dimethylbenzoyl diphenyl phosphine oxide, 2,4,6-trimethylbenzoyl diphenyl phosphine oxide, bis(2,6-dimethoxybenzoyl)-2,4,4-trimethylpentyl phosphine oxide, bis(2,4,6-trimethylbenzoyl)phenylphosphine oxide, and 2-hydroxy-1-{4-[4-(2-hydroxy-2-methyl-propionyl)-benzyl]-phenyl}-2-methyl-propane-1-on, for example.

Among them, benzophenone, 2-hydroxy-2-methyl-1-phenylpropane-1-on, 1-hydroxy cyclohexylphenyl ketone, 2,4,6-trimethylbenzoyl diphenyl phosphine oxide and 2-hydroxy-1-{4-[4-(2-hydroxy-2-methyl-propionyl)-benzyl]-phenyl}-2-methyl-propane-1-on are preferred and 1-hydroxy cyclohexylphenyl ketone, 2,4,6-trimethylbenzoyl diphenyl phosphine oxide and 2-hydroxy-1-{(4-[4-(2-hydroxy-2-methyl-propionyl)-benzyl]-phenyl}-2-methyl-propane-1-on are preferred because its curing speed is high and its crosslinking density can be elevated enough.

When the active-energy radiation curable polymer composition contains a radical polymerization group as well as cation polymerization group such as epoxy group, the above optical radical polymerization initiator and an optical cation polymerization initiator may be included as a polymerization initiator. Any known optical cation polymerization initiator can also be used as long as an effect of the present invention can be obtained.

In an active-energy radiation curable polymer composition related to the second aspect of the present invention, the amount of these optical polymerization initiators is preferably 10 parts by mass or less and more preferably 5 parts by mass or less, relative to the total amount of 100 parts by mass of the aforementioned active energy ray reactive components. When the amount of the optical polymerization initiator is 10 parts by mass or less, decrease in mechanical strength due to degradation products of the initiator can be suppressed, which is preferred.

The aforementioned photosensitization agent can be used for the same purpose as the polymerization initiator. One type or two or more types of photosensitization agents can be used and any known photosensitization agent can be used as far as effects of the present invention can be obtained. Such a photosensitization agent includes ethanol amine, diethanol amine, triethanol amine, N-methyl diethanol amine, 4-dimethyl aminobenzoic acid methyl, 4-dimethyl aminobenzoic acid ethyl, 4-dimethyl aminobenzoic acid amyl, and 4-dimethyl aminoacetophenone, for example.

In an active-energy radiation curable polymer composition related to the second aspect of the present invention, the amount of the aforementioned photosensitization agent is preferably 10 mass parts by mass or less and more preferably 5 parts by mass or less, relative to the total amount of 100 parts by mass of the aforementioned active energy ray reactive components. When the amount of the photosensitization agent is 10 parts by mass or less, decrease in mechanical strength due to lower crosslinking density can be suppressed, which is preferred.

For the aforementioned addition agent, various kinds of materials to be added to a composition used for the similar application can be used as an addition agent as far as effects of the present invention can be obtained. The addition agent may be one type or two or more types. Such an addition agent includes fillers such as glass fiber, glass beads, silica, alumina, calcium carbonate, isinglass, zinc oxide, titanium oxide, mica, talc, kaolin, metallic oxide, metallic fiber, iron, lead, and metallic powder; carbon materials such as carbon fiber, carbon black, black lead, carbon nanotube, and fullerenes such as C60 (fillers and carbon materials may be generically called "inorganic components"); modifying agents such as oxidation inhibitor, thermal stabilizer, ultraviolet absorber, HALS, fingerprint-resistant agent, surface hydrophilic agent, antistatic agent, slippage imparting agent, plasticizing agent, mold release agent, antifoaming agent, leveling agent, antisettling agent, surfactant, thixotropy imparting agent, lubricant, flame retardant, flame retardant aid agent, polymerization inhibitor, bulking agent, and silane coupling agent; coloring agents such as pigment, dye compound, and hue adjuster; monomer, and/or its oligomer, or curative agent, catalyst, and curing accelerators which are necessary for synthesizing an inorganic component.

In the active-energy radiation curable polymer composition related to the second aspect of the present invention, the amount of the aforementioned addition agent is preferably 10 parts by mass or less and more preferably 5 parts by mass or less, relative to the total amount of 100 parts by mass of the aforementioned active energy ray reactive components. When the amount of the addition agent is 10 parts by mass or less, decrease in mechanical strength due to lower crosslinking density can be suppressed, which is preferred.

The aforementioned solvent, for example, according to a coating method for forming a coating film of an active-energy radiation curable polymer composition related to the second aspect of the present invention, can be used in order to adjust viscosity of the active-energy radiation curable polymer composition related to the second aspect of the present invention. One type or two or more types of solvents can be used and any known solvent can be used as far as effects of the present invention can be obtained. Preferable solvents include toluene, xylene, ethyl acetate, butyl acetate, isopropanol, isobutanol, cyclohexane, methylethylketone, and methylisobutylketone. 400 parts by mass or less of the solvent can be usually used to 100 parts by mass of an active-energy radiation curable polymer composition.

A method for containing an optional ingredient such as the aforementioned addition agent to the active-energy radiation curable polymer composition related to the second aspect of the present invention is not specifically limited, but conventionally known mixing and dispersion method can be provided. In order to disperse the aforementioned optional ingredients surely, a dispersion process using a dispersion device is preferred. Specifically, for example, processing method using double-roll, triple roll, bead mill, ball mill, sand mill, pebble mill, trommel, sand grinder, segment barrier tryter, sun-and-planet stirring machine, high-speed impeller disperser, high-speed stone mill, high-speed impact mill, kneader, homogenizer, and ultrasonic disperser, etc. can be included.

The viscosity of the active-energy radiation curable polymer composition related to the second aspect of the present invention can be adjusted as required according to an application and usage aspect of the composition, while the viscosity of an E-type viscometer (rotor 1°34'×R24) at 25° C. is preferably 10 mPa·s or more, more preferably 100 mPa·s or more, while 100,000 mPa·s or less is preferable, and more preferably 50,000 mPa·s or less in terms of handling, coating, forming and 3D molding. The viscosity of the active-energy radiation curable polymer composition can be adjusted by, for example, the content of an urethane (meth)acrylate oligomer, a type of the aforementioned optional ingredient, and its blending ratio, etc.

As a coating method of the aforementioned active-energy radiation curable polymer composition, an known method such as bar coater method, application method, curtain flow coater method, roll coater method, spray method, gravure coater method, comma coater method, reverse roll coater method, lip coater method, die coater method, slot die coater method, air knife coater method, and dip coater method, etc. can be applied, while the bar coater method and the gravure coater method are preferred.

The active-energy radiation curable polymer composition related to the second aspect of the present invention can be a cured film by irradiating an active energy ray thereto.

An active energy ray to be used for curing the above composition includes infrared ray, visible ray, ultraviolet ray, X-ray, electron ray, α-ray, β-ray, and γ-ray, etc. Electron ray or ultraviolet ray is preferred in terms of an equipment cost and productivity, while as an light source, electron irradiation equipment, extra high pressure mercury lamp, high pressure mercury lamp, middle pressure mercury lamp, low pressure mercury lamp, metal halide lamp, Ar laser, He—Cd laser, solid-state laser, xenon lamp, high-frequency induction mercury lamp, or sun light, etc. is suited.

The irradiance level of the active energy ray can be arbitrarily selected according to the active-energy ray type, when it is cured by electron ray irradiation, the irradiance level is preferred to be 1 to 10 Mrad, for example. In case of ultraviolet ray irradiation, 50 to 1,000 mJ/cm$^2$ is preferred. An atmosphere during curing may be an air or an inert gas such as nitrogen or argon. Irradiation in an enclosed space between a film, glass and a metallic mold can also be applied.

The film thickness of the cured film related to the second aspect of the present invention can be arbitrarily decided according to a target application, but the lower limit is preferably 1 μm, more preferably 3 μm, and especially preferably 5 μm. Its upper limit is preferably 200 μm, more preferably 100 μm, especially preferably 50 μm, and the most preferably 20 μm. When the film thickness is larger than 1 μm, its design and functionality excellently appear after its 3D processing, while when it is smaller than 200 μm, an internal curing ability and 3D processing suitability is excellent, which is preferred.

Furthermore, a laminated body having a layer consisting of a cured film related to the second aspect of the present invention can be obtained on a base material. The laminated body related to the second aspect of the present invention is not specifically limited unless it has a layer consisting of a cured film related to the second aspect of the present invention, and a layer other than the base material and the cured film related to the second aspect of the present invention can be placed between the base material and the cured film related to the second aspect of the present invention, or can be placed outside. The aforementioned laminated body may have a base material and a plurality of cured film layers related to the second aspect of the present invention.

As a method for obtaining a laminated body related to the second aspect of the present invention, any known method such as method of laminating all layers when they are not cured and then curing them by an active energy ray, method of curing or partially-coating a lower layer by an active energy ray, applying an upper layer, and then curing them again by an active energy ray, and method of applying each layer onto a release film or a base film and then pasting those layers when they are not cured or partially cured, can be applied, while method of curing by an active energy ray when they are not cured is preferred, in terms of higher adhesiveness between layers. As a laminating method without being cured, an known method such as sequential application of applying a lower layer and then overlapping an upper layer, and a simultaneous multiple layer application of applying two or more layers at the same time from a multiple-slit, can be applied, but not limited.

The base material includes polyester such as polyethylene terephthalate and polybutylene terephthalate, polyolefin such as polypropylene, and various kinds of plastic materials such as nylon, polycarbonate, (meth)acrylate resin, etc., or various shapes of goods such as plate formed by metal.

The cured film related to the second aspect of the present invention can be a film excellent in contamination resistance and hardness against a general domestic contamination object such as ink and ethanol, etc., while the laminated body related to the second aspect of the present invention in which the cured film related to the second aspect of the present invention is used as a film for various kinds of base materials can be a one excellent in design and its surface protection.

The active-energy radiation curable polymer composition related to the second aspect of the present invention can give the cured film having flexibility which can be followed during 3D processing transformation, elongation at break, mechanical strength, contamination resistance and hardness together by considering the molecular weight between calculated network crosslinking points.

A value of the elongation at break of the cured film related to the second aspect of the present invention, in which the cured film related to the second aspect of the present invention is cut by 10 mm wide, a tensile testing was done by using a Tensilon tensile tester (made by Orientec, co. ltd, Tensilon UTM-III-100) under conditions of temperature of 140° C., tensile speed 50 mm/min., and the distance between chucks of 50 mm, is preferably 50% or more, more preferably 75% or more, further preferably 100% or more, and specially preferably 150% or more.

A value of the strength at break of a cured film related to the second aspect of the present invention, in which the cured film related to the second aspect of the present invention is cut by 10 mm wide, a tensile testing was done by using a Tensilon tensile tester (made by Orientec, co. ltd, Tensilon UTM-III-100) under conditions of temperature of 23° C., tensile speed 50 mm/min., and the distance between chucks of 50 mm, is preferably 40 MPa or more, more preferably 50 MPa or more, and further preferably 60 MPa or more.

A value of the elasticity of a cured film related to the second aspect of the present invention, in which the cured film related to the second aspect of the present invention is cut by 10 mm wide, a tensile testing was done by using a Tensilon tensile tester (made by Orientec, co. ltd, Tensilon UTM-III-100) under conditions of temperature of 23° C., tensile speed 50 mm/min., and the distance between chucks of 50 mm, is preferably 100 MPa or more, more preferably 200 MPa or more, further preferably 500 MPa or more, specially preferably 1,000 MPa or more, and specially preferably 2,000 MPa or more.

An value of the pencil hardness of the cured film related to the second aspect of the present invention, which was tested by an abrasion tester (made by Shinto Scientific Co., Ltd.: Haydon Dynamic strain amplifier 3K-34B) with a pencil of hardness 6B, 5B, 4B, 3B, 2B, B, HB, F, H, 2H (made by Mitsubishi Pencil, Co. Ltd.; Product number UNI, inspected by Japan Pant Inspection and Testing Association, for pencil scratch test) under conditions of 23° C./53% RH at 1 Kgf (9.8 N) load at scratching speed 25 mm/min. for pulling by 1 cm, is preferably HB or higher, more preferably F or higher, and further preferably H or higher.

Contamination resistance of the cured film related to the second aspect of the present invention is evaluated visually by dropping 0.03 g of 75 mass % ethanol precipitation, a red water-based ink (a cartridge ink made by Pilot Corporation/ red/IRF-12S-R) or a blue water-based ink (a cartridge ink made by Pilot Corporation/blue-black/IRF-12S-BB) (hereinafter, may be generally referred as "contaminated object") to contact the cured film, leave it at a room temperature (23° C.) for one hour for 75 mass % ethanol precipitation, while for 24 hours for a red or a blue water-based ink respectively, then wiping off the contaminated object by an absorbent cotton containing water. Where, the contaminated object amount after wiping it out is preferred to be an extremely small amount, and further preferred to be too little to be apparent visually.

The cured film related to the second aspect of the present invention and the laminated body related to the second aspect of the present invention can be used as an alternative film for paint, and can be effectively applied to a building material for interior and exterior decorating as well as various kinds of members such as automobile and home electronics.

As for the active-energy radiation curable polymer composition related to the second aspect of the present invention, when the cured film is obtained by curing it, contamination resistance against a general domestic contaminated object such as ink and ethanol, etc., and the cured film excellent in hardness can be obtained, and by using the cured film as a film for various kinds of base materials, the design and its surface protection can be obtained.

The active-energy radiation curable polymer composition related to the second aspect of the present invention can give a cured film having flexibility which can be followed during 3D processing transformation, elongation at break, mechanical strength, contamination resistance and hardness together by considering the calculated crosslinking points molecular weight. The active-energy radiation curable polymer composition related to the second aspect of the present invention is expected to be able to easily produce a thin film resin sheet by one layer application.

EXAMPLES

Hereinafter, the present invention is further described by using examples and comparative examples, but the present invention is not limited to these embodiments unless it exceeds the argument.

Hereinafter, evaluation methods for values of respective physical properties are as follows.
[Evaluation Method: Polycarbonate Diol]
[Number Average Molecular Weight]

The number average molecular weight (Mn) is calculated by solving a product into a $CDCl_3$ and measuring $^1$H-NMR (AVANCE 400 made by BRUKER) at 400 MHz to obtain its value of integral.
[Molecular Weight Distribution Mw/Mn]

The molecular weight distribution is calculated by obtaining Mn and Mw values on the conversion of polystyrene by measuring GPC under the following conditions.
Equipment: Tosoh 8020 made by Tosoh Corporation.
Column: PLgel 3 um MIXED-E (7.5 mmI.D.×30 cmL×2 columns)
Eluting solution: THF (tetrahydrofuran)
Current speed: 0.5 mL/min.
Column temperature: 40° C.
RI detector: RI (Equipment Tosoh 8020, built-in)
[Terminal Phenoxide Amount, Ether Bond Amount, Raw Material Diol Amount, and Phenol Amount]

They are calculated by solving a product into a $CDCl_3$ and measuring 400 MHz $^1$H-NMR (AVANCE 400 made by BRUKER) to obtain its integral value of signal of each component. The detection limit for this is 200 ppm as terminal phenoxide amount against the total weight of the entire samples, 500 ppm as ether group weight, and 100 ppm for phenol, 0.1 weight % for isosorbide, and 200 ppm for o-dichrolo benzene as a weight of a raw material diols or phenols. The terminal phenoxide proportion is calculated from the ratio of an integrated value of one proton for an terminal phenoxide and an integrated value of one proton for the entire terminal (total of three strutures of molecular chain terminal structure (A), molecular chain terminal structure (B) and terminal phenoxide), while the detection limit for the terminal phenoxide against the entire terminal is 0.05%.
[Remaining Diester Carbonate Amount]

The remaining amount of diester carbonate (diphenyl carbonate) was measured by GPC quantitative analysis under the following conditions:
(Analytical Conditions)
Column: Tskgel G2000 H XL 7.8 mm I.D×30 cm L 4 columns
Eluting solution: THF (tetrahydrofuran)
Current speed: 1.0 mL/min.
Column temperature: 40° C.
RI detector: RID-10A (Shimadzu Corporation)
[(A)/(B) Ratio, Terminal (A)/(B) Ratio, Terminal (A) Ratio (I)]

They are calculated by solving a product into $CDCl_3$ and measuring 400 MHz $^1$H-NMR (AVANCE400 made by BRUKER) to obtain its integral value. Its calculation method is described below.

Each ratio is obtained from the following chemical shift value of integral on the NMR chart. The chemical shift value may slightly differ according to its composition, in which case the value of integral needs to be arbitrarily obtained differently.

$\delta$5.22 to 4.98 ppm value of integral=a $\delta$4.79 to 4.61 ppm value of integral=b $\delta$4.61 to 4.47 ppm value of integral=c $\delta$3.68 to 3.51 ppm value of integral=d $\delta$2.73 to 2.66 ppm value of integral=e $\delta$1.52 to 1.30 ppm value of integral=f Structure (A) of a molecular chain terminal contains two types of isomers, which is classified as "(A) Terminal 1" and "(A) Terminal 2" respectively. A structure part derived from (A) in the polycarbonate diol other than the terminal is classified "(A) Intermediate" Similarly, (B) is classified as "(B) Terminal" and "(B) Intermediate". Considering the respective number of protons, each number is calculated by the following formula.

$(A)$ Terminal $1 = b - e$ $(A)$ Intermediate $= c - (A)$ Terminal 1

$(A)$ Terminal $2 = a - (A)$ Terminal $1 - (A)$ Intermediate$\times 2$ $(B)$ Terminal $= (d - e - (A)$ Terminal $1)/2$ $(B)$ Intermediate $= (f - (B)$ Terminal$\times 4)/4$ The number of each structure formula in a molecular chain described in formula (I) is represented as follows;
The number of molecular chain terminal structure (A)=(A) Terminal 1+(A) Terminal 2
The total number of molecular chain terminal structures (A) and (B)=(A) Terminal 1+(A) Terminal 2+(B) Terminal
The number of structures (A) in a molecular chain=(A) Terminal 1+(A) Terminal 2+(A) Intermediate
The total number of structures (A) and (B) in a molecular chain=(A) Terminal 1+(A) Terminal 2+(A) Intermediate+ (B) Terminal+(B) Intermediate
Terminal (A) ratio (I) can be obtained by applying the above values to formula (I).

[APHA value]
According to JIS K0071-1, it was compared and measured with a reference solution stored in a color comparison tube.

[Viscosity]
After a product was heated to 50° C., measurement was made by using E-type viscometer (DV-II+PRO made by BROOKFIELD, cone: CPE-52).

[Hydroxyl Value]
The value was measured and calculated by the following method. 14 g of phthalic anhydride was solved into 100 mL of pyridine to prepare a phthalate reagent. 1.50 to 1.60 g of the polycarbonate diol is solved into 5 mL of this phthalate reagent to react for one hour at 100° C. After this reaction solution is cooled at room temperature, it was diluted with 25 mL mixed solvent of THF/$H_2O$ (75/25). This solvent was titrated by using 1 N aqueous sodium hydroxide to obtain the amount of the aqueous sodium hydroxide which has been used until a flexion point is detected (main test). The same titration (blank test) was conducted for a solvent in which 5 mL of the phthalate reagent was diluted with a 25 mL mixed solvent of THF/$H_2O$ (75/25).

The hydroxyl value was obtained by the amount of the obtained aqueous sodium hydroxide by using the following formula. The number average molecular weight was calculated from this hydroxyl value.

$$\text{Hydroxyl value (mg-KOH/g)} = \{56.1 \times (B-A) \times f\}/S \quad \text{[Mathematical formula 4]}$$

A: Volume of the 1N aqueous sodium hydroxide required for titrimetric determination in main test (mL)
B: Volume of the 1N aqueous sodium hydroxide required for titrimetric determination in blank test (mL)
f: Titre of 1N aqueous sodium hydroxide
S: Sample (g)

[Average Number of Hydroxyl Groups Per Molecule]
The value was obtained by the following formula.

Average number of hydroxyl groups per molecule={(Number average molecular weight)×(Hydroxyl value)}/{1000×(KOH molecular weight)}

For the number average molecular weight, a measurement value of the aforementioned $^1$H-NMR was used, while a calculated value at the aforementioned titration was used for a hydroxyl value.

[Catalyst Amount]
About 0.1 g of a polycarbonate diol product was measured and solved into 4 mL of acetonitrile. Then 20 mL of pure water is added to precipitate the polycarbonate diol and remove the precipitated polycarbonate diol by filtration. Then the filtrated solvent is diluted to a predetermined concentration by pure water to analyze its metallic ion concentration by ion chromatography analysis. Here, the metallic ion concentration of the acetonitrile to be used as a solvent was measured as a blank value, while a value of the metallic ion concentration for the solvent is subtracted to obtain the metallic ion concentration for the polycarbonate diol product.

Measurement conditions are indicated in the following Table 1. Magnesium ion concentration was obtained by using results of analysis and the standard curves which was prepared in advance.

TABLE 1

| | Cation |
|---|---|
| Analyzer | Dionex Japan [DX-320] |
| | Chromatopac: Shimadzu Corporation [C-R7A] |
| Separation column | IonPac CS12A |
| Guard column | IonPac CG12A |
| Flow rate | 1.0 mL/min |
| Injection amount | 1.5 mL |
| Pressure | 960-990 psi |
| OVEN TEMP | 35° C. |
| Detection range of detecter | RANGE 200 μS |
| Suppressor | CSRS current value: 60 mA |
| Eluting solution | Methanesulfonic acid 20 mmol/L |
| Retention time | 10.9 min |

[Evaluation Method: Polyurethane]
[Molecular Weight]
GPC equipment made by Shimadze Corporation (Column TSKgel SuperHZM-N, lithium bromide-added dimethylacetamide for a solvent) is used to obtain the number average molecular weight in terms of standard polystyrene (Mn) as a molecular weight.

[Film Tension Property]
A tensile elongation at break and 100% modulus were measured with a strip polyurethane sample of 10 mm wide, 100 mm long, and about 100 μm thick by using a tensile tester (made by Orientec, co. ltd, Tensilon RTC-1210A) according to JIS K6301. It was executed under conditions of the distance between chucks of 50 mm, a tensile speed of 500 mm/min., a temperature of 23° C. and a relative humidity of 55%.

[Film Creep Property]
A polyurethane film with 100 μm thick is prepared, cut into a 10 mm-wide strip, marked reference line every 50 mm to obtain a sample. 1 MPa load was applied to this sample in a longitudinal direction under constant temperature and humidity conditions of temperature 23° C. and relative humidity 55% RH, and the load was removed after 16 hours later. The length of the reference line (Lmm) was measured to obtain its creep property ((L-50)/50)×100(%).

[Film Scratch Hardness (Pencil Method)]
A 100 μm-thick polyurethane was prepared and carefully attached and fixed onto a metallic mirror surface so as not to contain air bubble to measure its value according to JIS K-5600-5-4.

[Film Friction Resistant Test]
A 100 μm-thick polyurethane was prepared and fixed onto a tester (II-type, Gakushin-Type) to conduct up to 500 reciprocations of friction resistance test under 4.9N load according to JIS L0849.

[Urethanization Speed Test]
The reactivity of urethanization of obtained polycarbonate diol was observed as follows. PCD was dissolved in N,N-dimethylformamide (hereinafter "DMF") and added 0.98 times of diphenylmethane diisocyanate (hereinafter "MDI") at a predetermined temperature against a mol equivalent amount of the added polycarbonate diol, which was estimated from OH value of the polycarbonate diol.

Then, a load value (torque) which was a change of a churning motor load (unit: V) when the agitation of the solution was maintained at 100 rpm, was obtained. The read torque was a value in which the value before MDI addition was subtracted. For the motor, an agitator MAZERA Z-1210 made by TOKYO RIKAKIKAI CO. Ltd., was used. A 500 mL-separable flask was used as a polymerization reactor, and four wings combining two anchor types were used as agitation wings. Reactors, etc. to be used were well-washed and dried, and carefully placed so as not to contact air during a series of operations as much as possible under conditions of nitrogen circulation or encapsulation. A detection limit of the motor load value was 5 V. When the motor load value exceeded about 2 V, a polymerization solution viscosity was too high, while the polymerization solution did not return to its original state by gravity after agitation wing shearing and free spinning partially occurred, which did not result in correct motor load value measurement.

[Evaluation Method: Urethane(meth)acrylate Oligomer]

[Calculation Method of the Number Average Molecular Weight]

The urethane(meth)acrylate oligomer of examples and reference experiments contain three types of components of polyisocyanate, polycarbonate diol and hydroxyalkyl(meth) acrylate as its structural units. These structural units were formed with their component molecular weights maintained in the urethane(meth)acrylate oligomer, so in the examples and reference experiments, the average molecular weight of the urethane(meth)acrylate oligomer is calculated by total of products of those component mol ratios and molecular weights until the urethane(meth)acrylate oligomer is generated.

[Measurement of the Number Average Molecular Weight by GPC]

By using GPC ("HLC-8120 GPC" made by TOSOH Corporation), THF as a solvent, polystyrene as a standard sample, and TSKgel superH1000+H2000+H3000 as a column, the number average molecular weight of the urethane (meth)acrylate oligomer was measured at solution sending speed at 0.5 mL/min. and the column oven temperature of 40° C.

[Calculation of the Calculated Crosslinking Points Molecular Weight]

Since reactive group for a hydroxyalkyl(meth)acrylate in an urethane acrylate oligomer prepolymer is isocyanate group at both terminals of the prepolymer, and hydroxyalkyl (meth)acrylate bound to both terminals of the prepolymer by urethane bond is added by radical polymerization, so the crosslinking points of the urethane acrylate oligomer in the composition is (meth)acryloyl group located at both terminals of the urethane(meth)acrylate oligomer.

Therefore the active-energy radiation curable polymer composition is an aforementioned bifunctional (multifunctional) compound-single system composition in the following examples and reference experiments. Thus, the calculated crosslinking points molecular weight in those examples and reference experiments were obtained by the following formula.

(Number average molecular weight of the urethane (meth)acrylate oligomer/Number of cross-linking point in the urethane(meth)acrylate oligomer)×2     [Mathematical formula 5]

[Viscosity]

By using 1.2 g of an active-energy radiation curable polymer composition, a viscosity was measured by E-type viscometer ("TVE-20H" made by TOKYO KEIKI Inc.) with settings of rotation range 10 rpm, rotor 1°34'×R24, at 25° C.

[Mechanical Property of a Cured Film]

A cured film was cut by 10 mm wide, tensile testing was done by using a Tensilon tensile tester (made by Orientec, co. ltd, Tensilon UTM-III-100) under conditions of temperature of 23° C., relative humidity 53%, tensile speed 50 mm/min., and the distance between chucks of 50 mm to measure elongation at break, strength at break and tensile elasticity.

[Contamination Resistance of Cured Film]

0.03 g of a black oil-based ink, a red oil-based ink, a blue water-based ink (a cartridge ink made by Pilot Corporation/blue-black/IRF-12S-BB), a red water-based ink (a cartridge ink made by Pilot Corporation/red/IRF-12S-R), 10 mass % HCl aqueous solution, or 10 mass % NaOH aqueous solution (hereinafter, generally referred as "contaminated object") was dropped to contact a cured film, left it at a room temperature (23° C.) for 24 hours respectively, then wiped off the contaminated object by an absorbent cotton containing IPA for the black oil-based ink and the red oil-based ink, by an absorbent cotton containing water for the blue water-based ink, the red water-based ink, the 10 mass % HCl aqueous solution, or the 10 mass % NaOH aqueous solution to visually evaluate its contamination. Evaluation standard was as follows;

○: Contaminated object can be completely wiped out.

Δ: Small amount of contaminated object remains.

x: Substantial amount of contaminated object remains.

[Pencil Hardness of a Cured Film]

The hardness was tested by an abrasion tester (made by Shinto Scientific Co., Ltd.: Haydon Dynamic strain amplifier 3K-34B) with a pencil of hardness 6B, 5B, 4B, 3B, 2B, B, HB, F, H, 2H (made by Mitsubishi Pencil, Co. Ltd.; Product number UNI, inspected by Japan Pant Inspection and Testing Association, for pencil scratch test) under conditions of 23° C./53% RH. A 6B pencil of hardness was attached to the abrasion tester and pulled by 1 cm at 1 Kgf (9.8 N) load at scratching speed 25 mm/min. to visually check if any pulling evidence could be recognized or not. When any pulling evidence was not found, the pencil was replaced with one more level harder, and then repeated the similar operation to find out the hardest pencil hardness of which evidence was not found.

Experimental Example 1-1

1,6-hexanediol: 195.9 g, isosorbide: 242.3 g, diphenyl carbonate: 658.2 g, and magnesium acetate tetrahydrate: 4.3 mg were put into a 1 L glass separable flask, which was equipped with an agitator, a distillation trap, and a pressure adjusting device, and nitrogen gas replacement was conducted. The content was heated to 160° C. at its internal temperature for dissolution and for one-hour reaction. Then, the pressure was reduced down to 0.27 kPa gradually in two hours to distill and remove phenol and unreacted diol during the reaction. Then, nitrogen gas bubbling was conducted at 180° C. and 2.7 kPa for 45 minutes to distill and remove phenol and unreacted diol during the reaction. 400 g of o-dichlorobenzene was added and the pressure was maintained at 0.27 kPa and 130° C. for 2 hours for reaction, then bubbling with nitrogen gas was conducted for 2 hours at 2.7 kPa to remove the phenol and raise its polymerization degree of polycarbonate diol. The obtained polycarbonate diol product was 488.8 g.

The number average molecular weight (Mn) obtained from the hydroxyl value of the polycarbonate diol contained in this polycarbonate diol product was 1,940, the molecular weight distribution (Mw/Mn) was 1.96, (A)/(B) ratio (isosorbide/1,6-hexanediol) was 49/51, Terminal (A)/(B) ratio (terminal isosorbide/1,6-hexanediol ratio) was 73/27, and the terminal (A) ratio (I) calculated by the aforementioned (I) was 1.46.

The property of obtained polycarbonate diol product was a transparent solid at room temperature. The amount of raw diol isosorbide was 0.6 weight %, the phenol amount was 0.02 weight %, while the phenoxide terminal was 2% of entire terminals, and any polymer containing an ether bond other than isosorbide skeleton and o-dichrolobenzene was not detected. Remaining diphenyl carbonate was lower than the quantitation limit (lower than 0.01 weight %).

Experimental Example 2-1

1,6-hexanediol: 293.9 g, isosorbide: 121.2 g, diphenyl carbonate: 658.2 g, and magnesium acetate tetrahydrate: 4.3 mg into a 1 L glass separable flask, which was equipped with an agitator, a distillation trap, and a pressure adjusting device, and nitrogen gas replacement was conducted. The content was heated to 160° C. at its internal temperature for dissolution and for one-hour reaction. Then, the pressure was reduced down to 0.27 kPa gradually in two hours to distill and remove phenol and unreacted diol during the reaction. Then, nitrogen gas bubbling was conducted at 180° C. and 2.7 kPa for 15 minutes to distill and remove phenol and unreacted diol during the reaction. 400 g of o-dichrolobenzene was added and the pressure was maintained at 0.27 kPa and 130° C. for 5 hours for reaction, then bubbling with nitrogen gas was conducted for 13 hours at 2.7 kPa to remove the phenol and raise its polymerization degree of polycarbonate diol. The obtained polycarbonate diol product was 454.2 g.

The number average molecular weight (Mn) obtained from the hydroxyl value of the polycarbonate diol contained in this polycarbonate diol product was 2,100, the molecular weight distribution (Mw/Mn) was 1.96, (A)/(B) ratio was 24/76, Terminal (A)/(B) ratio was 62/38, and Terminal (A) ratio (I) was 2.58.

The property of obtained polycarbonate diol product was viscous liquid at a room temperature and fluidity was recognized. Viscosity (50° C.) was 24 Pa·s. The amount of raw diol isosorbide was 0.5 weight %, and a polymer which became a phenoxide terminal, a polymer containing an ether bond other than isosorbide skeleton, phenol and o-dichrolobenzene was not detected. Remaining diphenyl carbonate was lower than the quantitation limit (lower than 0.01 weight %).

Experimental Example 3-1

1,6-hexanediol: 218.5 g, isosorbide: 264.4 g, a diphenyl carbonate: 620.0 g, and magnesium acetate tetrahydrate: 4.7 mg were put into a 1 L glass separable flask, which was equipped with an agitator, a distillation trap, and a pressure adjusting device, and nitrogen gas replacement was conducted. The content was heated to 160° C. at its internal temperature for dissolution and for one-hour reaction. Then, the pressure was reduced down to 0.27 kPa gradually in two hours to distill and remove phenol and unreacted diol during the reaction. Then bubbling with nitrogen gas was conducted for 1.5 hours at 160° C. and 0.27 kPa to remove the phenol and unreacted diol. Then bubbling was conducted for 4 hours at 110° C. with the pressure kept at 0.27 kPa to remove the phenol. The obtained polycarbonate diol product was 520.5 g.

The number average molecular weight (Mn) obtained from the hydroxyl value of the polycarbonate diol contained in this polycarbonate diol product was 880, (A)/(B) ratio (isosorbide/1,6-hexanediol) was 49/51, Terminal (A)/(B) ratio (terminal isosorbide/1,6-hexanediol ratio) was 60/40, and the terminal (A) ratio (I) calculated by the aforementioned (I) was 1.22.

The property of obtained polycarbonate diol product was a transparent solid at room temperature. The amount of raw diol isosorbide was 2.0 weight %, phenol amount was 0.06 weight %, and a polymer which became a phenoxide terminal and a polymer containing an ether bond other than isosorbide skeleton were not detected. Remaining diphenyl carbonate was lower than the quantitation limit (lower than 0.01 weight %).

Experimental Example 4-1

1,6-hexanediol: 202.4 g, isosorbide: 750.9 g, diphenyl carbonate: 1046.8 g, and an aqueous solution of magnesium acetate tetrahydrate: 8.7 mL (concentration: 8.4 g/L, magnesium acetate tetrahydrate: 73 mg) were put into 5 L glass separable flask, which was equipped with an agitator, a distillation trap, and a pressure adjusting device, and nitrogen gas replacement was conducted. The content was firstly heated to 130° C. at its internal temperature for dissolution. When it was heated and dissolved, the pressure was reduced down to 5.33 kPa in 5 min. to react it for 240 min. at 5.33 kPa by distilling and removing the phenol. Then the pressure was reduced down to 0.40 kPa in 120 min., and then the temperature was raised to 160° C. in 80 min. to react it while distilling and removing the phenol and unreacted diol. Finally, the phenol and unreacted diol was distilled and removed at 0.40 kPa for 40 min. at 160° C. The obtained polycarbonate diol product was 989.2 g.

A thin-film distilling was conducted for the obtained polycarbonate diol product at flow rate of 20 g/min. (temperature: 180 to 200° C., Pressure: 0.027 kPa).

The number average molecular weight (Mn) obtained from the hydroxyl value of the polycarbonate diol contained in this polycarbonate diol product after this thin-film distilling was 900, (A)/(B) ratio (isosorbide/1,6-hexanediol) was 76/24, Terminal (A)/(B) ratio (terminal isosorbide/1,6-hexanediol ratio) was 91/9, and the terminal (A) ratio (I) calculated by the aforementioned (I) was 1.20.

The property of obtained polycarbonate diol product after this thin-film distilling was a light-yellow solid at room temperature. The amount of raw diol isosorbide was 2.5 weight %, and the phenol, a polymer which became a phenoxide terminal and a polymer containing an ether bond other than isosorbide skeleton were not detected. Remaining diphenyl carbonate was lower than the quantitation limit (lower than 0.01 weight %).

Experimental Example 1-2

78.3 g of the polycarbonate diol which was produced at Experimental example 1-1 was preheated to a melting point (ex. 120° C.) or more and added to a 1 L separable flask, the flask was placed in an oil bath set at 55° C. to heat and dimethylformamide (DMF) was added to dissolve it. An agitation started at about 100 rpm, 1,4-butanediol: 3.6 g was added, and tin stearate: 0.014 g was dropped. Then diphenylmethane diisocyanate (MDI): 19.8 g was dropped at a speed in which the liquid temperature does not exceed 70° C. MDI was dropped little by little up to 2.6 g until the weight-average molecular weight exceeds 150,000 measured by GPC to obtain a polyurethane solution of which solid concentration was 30 weight %. This polyurethane solution was applied onto a polyethylene film at uniform film thickness by a doctor blade and dried by a drier to obtain a polyurethane film.

When physical properties of this film were measured, its tensile elongation at break was 215% and 100% modulus was 53 MPa. The creep property of this film was 2%, a scratch hardness (Pencil method) was 2B to B, a friction resistant test returns no special surface difference after 500 reciprocations, and the weight reduction ratio was 1%.

Experimental Example 2-2

In stead of the polycarbonate diol made at Experimental example 1-1, the polycarbonate diol which was made at Experimental example 2-1 was used and others are the same as Experimental example 1-2 for reaction to obtain a polyurethane of which solid concentration was 30 weight %. This polyurethane solution was applied onto a polyethylene film at uniform film thickness by a doctor blade and dried by a drier to obtain a polyurethane film.

When physical properties of this film were measured, its tensile elongation at break was 324% and 100% modulus was 13 MPa. The creep property of this film was 15%, a scratch hardness (Pencil method) was 6B, scratch on its surface was recognized. A friction resistant test returns no special surface difference after 500 reciprocations, and the weight reduction ratio was 0.3%.

Reference Experimental Example 1-2

In stead of the polycarbonate diol made at Experimental example 1-1, a polycarbonate diol (Duranol T6002, the number average molecular weight: 1,986, made by Asahi Kasei Chemicals Corporation): 523 g was used and others are the same as Experimental example 1-2 for reaction to obtain a polyurethane of which solid concentration was 30 weight %. This polyurethane solution was applied onto a polyethylene film at uniform film thickness by a doctor blade and dried by a drier to obtain a polyurethane film.

When these film physical properties were measured, its tensile elongation at break was 580% and 100% modulus was 2.6 MPa. The creep property of this film was 6%, a scratch hardness (Pencil method) was 6B, and a substantial scratch on its surface was recognized. At a friction resistance test, substantial damage was recognized on its surface after 100 reciprocations, and the test had to be stopped.

[Consideration of Polyurethane Film]

Table 2 indicates physical properties of the polycarbonate diol product obtained at the aforementioned Experimental examples 1-1 and 2-1, and physical properties of the polyurethane film obtained by using those polycarbonate diol products at the aforementioned Experimental examples 1-2 and 2-2.

TABLE 2

| | | Example 1 | Example 2 | Comparative example 1 |
|---|---|---|---|---|
| Experimental example No./Reference experimental example No. | | Experimental example 1-1 | Experimental example 2-1 | — |
| Raw material diol [mol %] | 16 HD | 50 | 75 | — |
| | ISB | 50 | 25 | — |
| Physical property of polycarbonate diol | Molecular weight (OH value) | 1940 | 2100 | — |
| | Aspect | Transparent solid | Viscous liquid | — |
| Experimental example No./Reference experimental example No. | | Experimental example 1-2 | Experimental example 2-2 | Reference experimental example 1-2 |
| Physical property of Polyurethane film | Tensile fracture elongation [%] | 215 | 324 | 580 |
| | 100% modulus [MPa] | 53 | 13 | 2.6 |
| | Creep property [%] | 2 | 15 | 6 |
| | Pencil hardness | 2B-B | 6 B | 6 B |

As is clear from Examples 1 and 2, the polyurethane film created by the polycarbonate diol obtained by using isosorbide and 1,6-hexanediol as a raw material diol indicates a high 100% modulus and a high friction resistance is indicated at a friction resistance test that the surface is nearly unchanged after 500 reciprocations. In particular, Example 1 with high ISB ratio indicates a high pencil hardness of 2B to B.

On the other hand, as is clear from Comparative example 1, the polyurethane film produced by the polycarbonate diol obtained by using 1,6-hexanediol only as a raw material diol indicates lower strength and hardness than the polycarbonate diol produced by isosorbide and at a friction resistance test, substantial damage was recognized on its surface after 100 reciprocations, and the test had to be stopped.

Experimental Example 1-3

To a four-outlet flask equipped with an agitator, a reflux condenser, a drip funnel, and a thermometer, 119 g of isophorone diisocyanate as a polyisocyanate, and 519 g of the polycarbonate diol of Experimental example 1-1 as an polycarbonate diol and 273 g of methylethylketone were added and reaction was conducted by heating to 80° C. in an oil bath for 9 hours. After the reaction, it was cooled down to 60° C.; then 0.21 g of dioctyltin dilaurate, 0.35 g of methylhydroquinone, and 27 g of methylethylketone were added; and 62 g of hydroxyethyl acrylate as a hydroxyalkyl (meth)acrylate was dropped to start reaction. Reaction was executed for 10 hours while heating at 70° C. in an oil bath to check the reaction progress with the decrease of peak derived from isocyanate (NCO) group by Infrared absorption spectrum (may be abbreviated as IR), while its reaction's ending point was confirmed at its disappearance to obtain urethane(meth)acrylate oligomer 1. The urethane (meth)acrylate oligomer 1 solution obtained by this was an active-energy radiation curable polymer composition 1.

The obtained active-energy radiation curable polymer composition 1 had a calculated crosslinking points molecular weight of 2,620. The urethane(meth)acrylate oligomer 1 obtained by GPC had the number average molecular weight of 2,570. Moreover, the amount of the urethane(meth) acrylate oligomer 1 in the active-energy radiation curable polymer composition 1 was 70 mass %, and the viscosity of the active-energy radiation curable polymer composition 1 was 2,260 mPa·s.

Next, the obtained active-energy radiation curable polymer composition 1 was coated onto a polyethylene terephthalate film by an applicator to form a coated film, dried it for one minute at 60° C., an electron irradiation apparatus (CB175, EYE GRAPHICS CO., LTD.) was used to irradiate an electron beam onto the dried coated film under the condition of accelerating voltage of 165 kV and exposure dose of 5 Mrad to form a cured film 1. Then, the cured film 1 is delaminated from the polyethylene terephthalate film to obtain the cured film 1 with the film thickness of 50 μm. Mechanical properties, contamination resistance, abrasion resistance and pencil hardness were evaluated about the obtained cured film 1. Their results are shown in Table 3.

Experimental Example 2-3

Although isophorone diisocyanate was changed from 119 g to 112 g, the 519 g of polycarbonate diol of Experimental example 1-1 is changed to the 530 g of polycarbonate diol of Experimental example 2-1, methylethylketone was changed from 273 g to 275 g, methylethylketone was changed from 27 g to 25 g, hydroxyethyl acrylate was from 62 g to 59 g, other conditions were the same as Experimental example 1-3 to obtain an urethane(meth)acrylate oligomer 2 as well as an active-energy radiation curable polymer composition 2, which was an urethane(meth)acrylate oligomer 2 solution.

The obtained active-energy radiation curable polymer composition 2 had a molecular weight between calculated network cross-linking points of 2,780. The urethane(meth) acrylate oligomer 2 obtained by the GPC had the number average molecular weight of 2,870. The amount of the urethane(meth)acrylate oligomer 2 in the active-energy radiation curable polymer composition 2 was 70 mass %, and the viscosity of the active-energy radiation curable polymer composition 2 was 2,720 mPa·s.

Then, except for using the active-energy radiation curable polymer composition 2 obtained in the above, its conditions were the same as Experimental example 1-3 to obtain a cured film 2. Mechanical properties, contamination resistance, abrasion resistance and pencil hardness were evaluated about the obtained cured film 2. Their results are shown in Table 3.

Experimental Example 3-3

Isophorone diisocyanate was changed from 119 g to 200 g, 519 g of the polycarbonate diol at Experimental example 1-1 was changed to 396 g of the polycarbonate diol at Experimental example 3-1, a methylethylketone was from 273 g to 255 g, a methylethylketone was increased from 27 g to 45 g, a hydroxyethyl acrylate was from 62 g to 104 g, but other conditions were the same as Experimental example 1-3 to obtain an urethane(meth)acrylate oligomer 3 as well as an active-energy radiation curable polymer composition 3 which was an urethane(meth)acrylate oligomer 3 solution.

The obtained active-energy radiation curable polymer composition 3 had a molecular weight between calculated network cross-linking points of 1,550. Moreover, the urethane(meth)acrylate oligomer 3 obtained by GPC had the number average molecular weight of 1,690. The amount of the urethane(meth)acrylate oligomer 3 in the active-energy radiation curable polymer composition 3 was 70 mass %, and the viscosity of the active-energy radiation curable polymer composition 3 was 1,190 mPa·s.

Then, except for using the active-energy radiation curable polymer composition 3 obtained in the above, its conditions were the same as Experimental example 1-3 to obtain a cured film 3. Mechanical properties, contamination resistance, abrasion resistance and pencil hardness were evaluated about the obtained cured film 3. Their results are shown in Table 3.

Experimental Example 4-3

Isophorone diisocyanate was changed from 119 g to 197 g, 519 g of the polycarbonate diol at Experimental example 1-1 was changed to 400 g of the polycarbonate diol at Experimental example 4-1, methylethylketone was from 273 g to 256 g, methylethylketone was from 27 g to 44 g, hydroxyethyl acrylate was from 62 g to 103 g, but other conditions were the same as Experimental example 1-3 to obtain an urethane(meth)acrylate oligomer 4 as well as an active-energy radiation curable polymer composition 4 which was an urethane(meth)acrylate oligomer 4 solution.

The obtained active-energy radiation curable polymer composition 4 had a molecular weight between calculated network cross-linking points of 1,570. The urethane(meth) acrylate oligomer 4 obtained by the GPC had the number average molecular weight of 1,670. The amount of the urethane(meth)acrylate oligomer 4 in the active-energy radiation curable polymer composition 4 was 70 mass %, and the viscosity of the active-energy radiation curable polymer composition 4 was 9,540 mPa·s.

Then, except for using the active-energy radiation curable polymer composition 4 obtained in the above, its conditions were the same as Experimental example 1-3 to obtain a cured film 4. Mechanical properties, contamination resistance, abrasion resistance and pencil hardness were evaluated about the obtained cured film 4. Their results are shown in Table 3.

Reference Experimental Example 2-3

Isophorone diisocyanate was changed from 119 g to 116 g, 519 g of the polycarbonate diol at Experimental example 1-1 was changed to 523 g of the polycarbonate diol (Duranol T 5652, number average molecular weight: 2,000, made by Asahi Kasei Chemicals Corporation), methylethylketone to be added before the pre-polymer generation reaction was from 273 g to 274 g, methylethylketone to be added after the pre-polymer generation reaction was from 27 g to 26 g, hydroxyethyl acrylate was from 62 g to 61 g, but other conditions were the same as Experimental example 1-3 to obtain an urethane(meth)acrylate oligomer C1 as well as an active-energy radiation curable polymer composition C1 which was an urethane(meth)acrylate oligomer C1 solution.

The obtained active-energy radiation curable polymer composition C1 had a molecular weight between calculated network cross-linking points of 2,680. The urethane(meth) acrylate oligomer C1 obtained by GPC had the number average molecular weight of 2,870. The amount of the urethane(meth)acrylate oligomer C1 in the active-energy radiation curable polymer composition C1 was 70 mass %, and the viscosity of the active-energy radiation curable polymer composition 1 was 1,390 mPa·s.

Then, except for using the active-energy radiation curable polymer composition C1 obtained in the above, its conditions were the same as Experimental example 1-3 to obtain a cured film C1. Mechanical properties, contamination resistance, abrasion resistance and pencil hardness were evaluated about the obtained cured film C1. Their results are shown in Table 3.

Reference Experimental Example 3-3

Isophorone diisocyanate was changed from 119 g to 117 g, 519 g of the polycarbonate diol at Experimental example 1-1 was changed to 523 g of the polycarbonate diol (Kuraray polyol C-2050, number average molecular weight: 1,990, made by KURARAY CO., LTD.), methylethylketone to be added before the prepolymer generation reaction was from 273 g to 274 g, methylethylketone to be added after the prepolymer generation reaction is from 27 g to 26 g, hydroxyethyl acrylate was from 62 g to 61 g, but other conditions were the same as Experimental example 1-3 to obtain an urethane(meth)acrylate oligomer C2 as well as an active-energy radiation curable polymer composition C2 which was an urethane(meth)acrylate oligomer C2 solution.

The obtained active-energy radiation curable polymer composition C2 had a molecular weight between calculated network cross-linking points of 2,670. The urethane(meth) acrylate oligomer C2 obtained by GPC had the number average molecular weight of 2,600. The amount of the urethane(meth)acrylate oligomer C2 in the active-energy radiation curable polymer composition C2 was 70 mass %, and the viscosity of the active-energy radiation curable polymer composition C2 was 890 mPa·s.

Then, except for using the active-energy radiation curable polymer composition C2 obtained in the above, its conditions were the same as Experimental example 1-3 to obtain a cured film C2. Mechanical properties, contamination resistance, abrasion resistance and pencil hardness were evaluated about the obtained cured film C2. Their results are shown in Table 3.

Reference Experimental Example 4-3

Isophorone diisocyanate was changed from 119 g to 115 g, 519 g of the polycarbonate diol at Experimental example 1-1 was changed to 525 g of the polycarbonate diol (Nipporan 980N, number average molecular weight: 2,030, made by NIPPON POLYURETHANE INDUSTRY CO., LTD.), methylethylketone to be added before the prepolymer generation reaction was from 273 g to 274 g, methylethylketone to be added after the prepolymer generation reaction was from 27 g to 26 g, hydroxyethyl acrylate was from 62 g to 60 g, but other conditions were the same as Experimental example 1-3 to obtain an urethane(meth)acrylate oligomer C3 as well as an active-energy radiation curable polymer composition C3 which was an urethane(meth)acrylate oligomer C3 solution.

The obtained active-energy radiation curable polymer composition C3 had a molecular weight between calculated network cross-linking points of 2,710. The urethane(meth) acrylate oligomer C3 obtained by GPC had the number average molecular weight of 2,820. The amount of the urethane(meth)acrylate oligomer C3 in the active-energy radiation curable polymer composition C3 was 70 mass %, and the viscosity of the active-energy radiation curable polymer composition C3 was 1560 mPa·s Then, except for using the active-energy radiation curable polymer composition C3 obtained in the above, its conditions were the same as Experimental example 1-3 to obtain a cured film C3. Mechanical properties, contamination resistance, abrasion resistance and pencil hardness were evaluated about the obtained cured film C3. Their results are shown in Table 3.

Reference Experimental Example 5-3

Isophorone diisocyanate was changed from 119 g to 195 g, 519 g of the polycarbonate diol at Experimental example 1-1 was changed to 404 g of the polycarbonate diol (ETERNACOL UM-90 (1/1), number average molecular weight: 920, made by Ube Industries, Ltd.), methylethylketone to be added before the prepolymer generation reaction was from 273 g to 256 g, methylethylketone to be added after the prepolymer generation reaction was from 27 g to 44 g, hydroxyethyl acrylate was from 62 g to 102 g, but other conditions were the same as Experimental example 1-3 to obtain an urethane(meth)acrylate oligomer C4 as well as an active-energy radiation curable polymer composition C4 which was an urethane(meth)acrylate oligomer C4 solution.

The obtained active-energy radiation curable polymer composition had a molecular weight between calculated network cross-linking points of 1,600. The urethane(meth) acrylate oligomer C4 obtained by GPC had the number average molecular weight of 1,840. The amount of the urethane(meth)acrylate oligomer C4 in the active-energy radiation curable polymer composition C4 was 70 mass %, and the viscosity of the active-energy radiation curable polymer composition C4 was 750 mPa·s Then, except for using the active-energy radiation curable polymer composition C4 obtained in the above, its conditions were the same as Experimental example 1-3 to obtain a cured film C4. Mechanical properties, contamination resistance, abrasion resistance and pencil hardness were evaluated about the obtained cured film C4. Their results are shown in Table 3.

TABLE 3

| | | | Experimental example 1-3 | Experimental example 2-3 | Experimental example 3-3 | Experimental example 4-3 | Reference experimental example 2-3 | Reference experimental example 3-3 | Reference experimental example 4-3 | Reference experimental example 5-3 |
|---|---|---|---|---|---|---|---|---|---|---|
| Urethane acrylate oligomer [Weight ratio] | a-1 | Isophorone diisocyanate (number average molecular weight 222) | 119 | 112 | 200 | 197 | 116 | 117 | 115 | 195 |
| | a-2 | Experimental example 1-1 (polycarbonate polyol) calculated with the number average molecular weight 1940/OH number 57.82 | 519 | | | | | | | |
| | | Experimental example 2-1 (polycarbonate polyol) calculated with the number average molecular weight 2100/OH number 53.5 | | 530 | | | | | | |
| | | Experimental example 3-1 (polycarbonate polyol) calculated with the number average molecular weight 880/OH number 127 | | | 396 | | | | | |
| | | Experimental example 4-1 (polycarbonate polyol) calculated with the number average molecular weight 900/OH number 125 | | | | 400 | | | | |
| | a-3 | Hydroxyethyl acrylate (number average molecular weight 116) | 62 | 59 | 104 | 103 | 61 | 61 | 60 | 102 |
| | a-4 | T5652 (polycarbonate polyol) calculated with the number average molecular weight 2000/OH number 56.1 (analyzed value provided by the manufacturer) | | | | | 523 | | | |
| | | C-2050 (polycarbonate polyol) calculated with the number average molecular weight 1990/OH number 56.5 (analyzed value provided by the manufacturer) | | | | | | 523 | | |
| | | 980N (polycarbonate diol) calculated with the number average molecular weight 2030/OH number 55.4 (analyzed value provided by the manufacturer) | | | | | | | 525 | |
| | | UM-90(1/1) (polycarbonate diol) calculated with the number average molecular weight 920/OH number 122.7 (analyzed value provided by the manufacturer) | | | | | | | | 404 |
| Urethane acrylate oligomer [Mol ratio] | a-1 | Isophorone diisocyanate (number average molecular weight 222) | 2 | 2 | 2 | 2 | 2 | 2 | 2 | 2 |
| | a-2 | Experimental example 1-1 (polycarbonate polyol) calculated with the number average molecular weight 1940/OH number 57.82 | 1 | | | | | | | |
| | | Experimental example 2-1 (polycarbonate polyol) (calculated with the number average molecular weight 2100/OH number 53.5 | | 1 | | | | | | |
| | | Experimental example 3-1 (polycarbonate polyol) calculated with the number average molecular weight 880/OH number 127 | | | 1 | | | | | |
| | | Experimental example 4-1 (polycarbonate polyol) calculated with the number average molecular weight 900/OH number 125 | | | | 1 | | | | |

TABLE 3-continued

| | | | Experimental example 1-3 | Experimental example 2-3 | Experimental example 3-3 | Experimental example 4-3 | Reference experimental example 2-3 | Reference experimental example 3-3 | Reference experimental example 4-3 | Reference experimental example 5-3 |
|---|---|---|---|---|---|---|---|---|---|---|
| | a-3 | Hydroxyethyl acrylate (number average molecular weight 116) | 2 | 2 | 2 | 2 | 2 | 2 | 2 | 2 |
| | a-4 | T5652 (polycarbonate polyol) (calculated with the number average molecular weight 2000/ OH number 56.1 (analyzed value provided by the manufacturer) | | | | | 1 | | | |
| | | C-2050 (polycarbonate polyol) (calculated with the number average molecular weight 1990/ OH number 56.5 (analyzed value provided by the manufacturer) | | | | | | 1 | | |
| | | 980N (polycarbonate diol) (calculated with the number average molecular weight 2030/ OH number 55.4 (analyzed value provided by the manufacturer) | | | | | | | 1 | |
| | | UM-90(1/1) (polycarbonate diol) (calculated with the number average molecular weight 920/ OH number 122.7 (analyzed value provided by the manufacturer) | | | | | | | | 1 |
| Urethane acrylate oligomer | The calculated-number average molecular weight | | 2620 | 2780 | 1550 | 1570 | 2680 | 2670 | 2710 | 1600 |
| | The number average molecular weight measured by GPC | | 2570 | 2870 | 1690 | 1670 | 2870 | 2600 | 2820 | 1840 |
| Active energy ray-curable polymer composition | Content of urethane(meth)acrylate oligomer [mass %] | | 70 | 70 | 70 | 70 | 70 | 70 | 70 | 70 |
| | Viscosity [mPa·s/25 degrees C.] | | 2260 | 2720 | 1190 | 9540 | 1390 | 890 | 1560 | 750 |
| | Calculated molecular weight between crosslinking points | | 2620 | 2780 | 1550 | 1570 | 2680 | 2670 | 2710 | 1600 |
| Cured film | Mechanical properties | Tensile fracture elongation [%] | 110 | 150 | 5 | 5 | 110 | 90 | 120 | 60 |
| | | Tensile fracture strength [MPa] | 60 | 60 | 50 | 60 | 10 | 10 | 20 | 30 |
| | | Tensile elasticity [MPa] | 2020 | 140 | 2010 | 2110 | 10 | 12 | 10 | 100 |
| | Contamination resistance | Black oil-based ink (r. t x left as it is for 24 Hrs, then wiped off with IPA) | x | x | ○ | ○ | x | x | x | Δ |
| | | Red oil-based ink (r. t x left as it is for 24 Hrs, then wiped off with IPA) | x | Δ | ○ | ○ | x | x | x | Δ |
| | | Blue water-based ink (r. tx left with cover for 24 Hrs, then wiped off with a damp cloth) | Δ | x | ○ | ○ | x | x | x | Δ |
| | | Red water-based ink (r. tx left with cover for 24 Hrs, then wiped off with a damp cloth) | ○ | x | ○ | ○ | x | x | x | Δ |
| | | 10 wt % HCl aqueous solution (r. tx left with cover for 24 Hrs, then wiped off with a damp cloth) | ○ | ○ | ○ | ○ | ○ | ○ | ○ | ○ |
| | | 10 wt % NaOH aqueous solution (r. tx left with cover for 24 Hrs, then wiped off with a damp cloth) | ○ | ○ | ○ | ○ | ○ | ○ | ○ | ○ |
| | Pencil hardness | | HB | 3B | H | H | 5B | 3B | 6 B | F |

Constitutional unit mass ratio of a polyol in a polycarbonate polyol, OH value of a polyol in a polycarbonate polyol, and the number average molecular weight of a polyol in a polycarbonate polyol are indicated in Table 4. The number average molecular weights of T5652, C-2050, 980N and UM-90 (1/1) are values in their brochures.

resistance against a water-based ink, and higher pencil hardness relative to these Reference experiments.

Polycarbonate polyol in Example 4 and Comparative example 4 all have almost the same number average molecular weight, calculated molecular weight between cross-linking points, and OH values, and 75 mass % of constitu-

TABLE 4

| | | Experimental example 1-3 | Experimental example 2-3 | Experimental example 3-3 | Experimental example 4-3 | Reference experimental example 2-3 | Reference experimental example 3-3 | Reference experimental example 4-3 | Reference experimental example 5-3 |
|---|---|---|---|---|---|---|---|---|---|
| Polycarbonate polyol Constitutional unit: Raw material glycol [Weight ratio] | Isosorbide | 50 | 25 | 50 | 75 | 0 | 0 | 0 | 0 |
| | Cyclohexanedimethanol | 0 | 0 | 0 | 0 | 0 | 0 | 0 | 50 |
| | 1,5-Pentanediol | 0 | 0 | 0 | 0 | 50 | 0 | 0 | 0 |
| | 3-Methylpentanediol | 0 | 0 | 0 | 0 | 0 | 50 | 0 | 0 |
| | 1,6-Hexanediol | 50 | 75 | 50 | 25 | 50 | 50 | 100 | 50 |
| OH value [mgKOH/g] | | 57.52 | 53.5 | 127.7 | 125 | 56.1 | 56.5 | 55.4 | 122.7 |
| Number average molecular weight | | 1940 | 2100 | 880 | 900 | 2000 | 1990 | 2030 | 920 |
| The average number of hydroxyl groups per one molecule | | 2.0 | 2.0 | 2.0 | 2.0 | 2.0 | 2.0 | 2.0 | 2.0 |

[Consideration of a Cured Film]

Table 5 indicates physical properties of the polycarbonate diol products obtained at the aforementioned Experimental examples 1-1, 2-1, 3-1, and 4-1 and physical properties of the polyurethane films obtained by using those polycarbonate diol products at the aforementioned Experimental examples 1-2, 2-2, 3-2 and 4-2.

tional units are 1,6-hexanediol in Example 4 and remaining 25 mass % are isosorbide, but in Comparative example 4, all constitutional units are 1,6-hexanediol. The cured film in Example 4 has better tensile elongation at break than the cured film in Comparative example 4, better tensile strength

TABLE 5

| | | Example 3 | Example 4 | Example 5 | Example 6 | Comparative example 2 | Comparative example 3 | Comparative example 4 | Comparative example 5 |
|---|---|---|---|---|---|---|---|---|---|
| Experimental example No./Reference experimental example No. | | Experimental example 1-1 | Experimental example 2-1 | Experimental example 3-1 | Experimental example 4-1 | — | — | — | — |
| Raw material diol [mol %] | 16 HD | 50 | 75 | 50 | 25 | — | — | — | — |
| | ISB | 50 | 25 | 50 | 75 | — | — | — | — |
| Physical property of polycarbonate diol | Molecular weight (OH value) | 1940 | 2100 | 880 | 900 | — | — | — | — |
| | Average number of hydroxyl groups per one molecule | 2.0 | 2.0 | 2.0 | 2.0 | — | — | — | — |
| | Aspect | Transparent solid | Viscous liquid | Transparent solid | Light-yellow solid | — | — | — | — |
| | White foreign body | None | None | None | None | — | — | — | — |
| Experimental example No./Reference experimental example No. | | Experimental example 1-1 | Experimental example 2-3 | Experimental example 3-3 | Experimental example 4-3 | Reference experimental example 2-3 | Reference experimental example 3-3 | Reference experimental example 4-3 | Reference experimental example 5-3 |
| Cured film properties | Tensile fracture elongation [%] | 110 | 150 | 5 | 5 | 110 | 90 | 120 | 60 |
| | Tensile fracture strength [MPa] | 60 | 60 | 50 | 60 | 10 | 10 | 20 | 30 |
| | Tensile elasticity [MPa] | 2020 | 140 | 2010 | 2110 | 10 | 12 | 10 | 100 |
| | Pencil hardness | HB | 3B | H | H | 5B | 3B | 6 B | F |

Polycarbonate polyol in Example 3, Comparative example 2, and Comparative example 3 all have almost the same number average molecular weight, calculated molecular weight between cross-linking points, and OH values, and 50 mass % of constitutional units are 1,6-hexanediol, while remaining 50 mass % of the constitutional unit in Example 3 are isosorbide, but 1,5-pentanediol and 3-methylpentanediol in Comparative example 2 and 3. The cured film in Example 3 has an almost same tensile elongation at break as cured films in Reference experiments example 2-3 and 3-3, better tensile strength at break, more higher contamination at break, higher contamination resistance against a red oil-based ink, and higher pencil hardness relative to the comparative example.

Polycarbonate polyol in Example 5 and Comparative example 5 all have almost the same number average molecular weight, calculated molecular weight between cross-linking points, and OH values, and 50 mass % of constitutional units are 1,6-hexanediol, while in Example 5 the remaining 50 mass % are isosorbide, but in Comparative example 5, is cyclohexane dimethanol. The cured film in Example 5 has lower tensile elongation at break however it has higher tensile strength at break compared to the cured film in Comparative example 5, and it has higher contamination resistance against a water-based and oil-based ink, and higher pencil hardness relative to the comparative example.

Polycarbonate polyol in Examples 6 and 5 all have almost the same number average molecular weight, calculated molecular weight between cross-linking points, and OH values, while a proportion of isosorbide in a constitutional unit consisting of 1,6-hexanediol and isosorbide is 75 mass % in Example 6, but 50 mass % in Example 5. The cured film in Example 6 has almost the same tensile strength at break and contamination resistance, and pencil hardness compared to the cured film in Example 5.

In this regard, when a cured film, which was obtained from an active-energy radiation curable polymer composition containing an urethane(meth)acrylate oligomer is used, in which the oligomer was given tenderization trend by including a high-molecular weight polyol having over 500 number average molecular weights excluding the aforementioned polycarbonate diol thereto, and/or increasing calculated molecular weight between cross-linking points thereof etc., the cured film containing polycarbonate diol of Experimental example 4-1 is estimated to be better balanced between 3D processing characteristic and contamination resistance compared to the cured film containing the polycarbonate diol at Experimental example 3-1.

From the aforementioned examples and comparative examples, it is clear that the composition containing polycarbonate polyol containing isosorbide in its constitutional unit and having cross-linking points at both terminals can form a better cured film by irradiating an active energy ray excellent in mechanical strength and contamination resistance than a similar composition containing other polycarbonate polyol.

Experimental Example 5-1

1,6-hexanediol (16 BD): 404.3 g, isosorbide (ISB): 500.1 g, diphenyl carbonate: 1095.6 g, and an aqueous solution of magnesium acetate tetrahydrate: 0.87 mL (concentration: 8.4 g/L, magnesium acetate tetrahydrate: 7.3 mg) were put into a 5 L glass separable flask, which was equipped with an agitator, a distillation trap, and a pressure adjusting device, and nitrogen gas replacement was conducted. The content was firstly heated to 130° C. at its internal temperature for dissolution. When it was heated and dissolved, the pressure was reduced down to 4.67 kPa in 5 min. to react it at 130° C. for 20 min. at 4.67 kPa. Then the pressure was reduced down to 0.40 kPa in 260 min., and then the temperature was raised to 160° C. in 80 min. to react it while distilling and removing the phenol and unreacted diol. The obtained polycarbonate diol product was 805.0 g. The contained magnesium amount was 1.06 weight ppm.

A thin-film distilling was conducted for the obtained polycarbonate diol product at flow rate of 20 g/min. (temperature: 180 to 200° C., Pressure: 0.027 kPa).

The number average molecular weight (Mn) obtained after this thin-film distilling from NMR analysis of the polycarbonate diol contained in this polycarbonate diol product was 1,465, (A)/(B) ratio (isosorbide/1,6-hexanediol) was 61/39, Terminal (A)/(B) ratio (terminal isosorbide/1,6-hexanediol ratio) was 68/32, and the terminal (A) ratio (I) calculated by the aforementioned (I) was 1.11.

The property of obtained polycarbonate diol product was a transparent solid at a room temperature and the contained magnesium amount was 1.14 weight ppm. APHA value was 60, and the amount of raw diol isosorbide was 0.14 weight %, phenol amount was 0.23 weight %, and the phenoxide terminal was 9% of entire terminals. Any polymer containing an ether bond other than isosorbide skeleton was not detected. Remaining diphenyl carbonate was lower than the quantitation limit (lower than 0.01 weight %).

Experimental Example 6-1

1,6-hexanediol: 404.3 g, isosorbide: 500.1 g; diphenyl carbonate: 1095.6 g; and an aqueous solution of magnesium acetate tetrahydrate: 4.4 mL (concentration: 8.4 g/L, magnesium acetate tetrahydrate: 37 mg) were put into a 5 L glass separable flask, which was equipped with an agitator, a distillation trap, and a pressure adjusting device, and nitrogen gas replacement was conducted. The content was firstly heated to 130° C. at its internal temperature for dissolution. When it was heated and dissolved, the pressure was reduced down to 5.33 kPa in 5 min. to react it at 130° C. for 180 min. at 5.33 kPa by distilling and removing the phenol. Then the pressure was reduced down to 0.40 kPa in 100 min., and then the temperature was raised to 160° C. in 100 min. to react while distilling and removing the phenol and unreacted diol. The obtained polycarbonate diol product was 967.8 g. The contained magnesium amount was 4.29 weight ppm.

The number average molecular weight (Mn) obtained from NMR analysis of the polycarbonate diol contained in this polycarbonate diol product was 928, (A)/(B) ratio (isosorbide/1,6-hexanediol) was 51/49, Terminal (A)/(B) ratio (terminal isosorbide/1,6-hexanediol ratio) was 71/29, and the terminal (A) ratio (I) calculated by the aforementioned (I) was 1.39.

The property of obtained polycarbonate diol product was a transparent solid at room temperature. APHA value was 60, and the amount of raw diol isosorbide was 3.60 weight %, phenol amount was 1.06 weight %, and a polymer which became a phenoxide terminal and a polymer containing an ether bond other than isosorbide skeleton were not detected. Remaining diphenyl carbonate was lower than the quantitation limit (lower than 0.01 weight %).

Experimental Example 7-1

1,6-hexanediol: 404.3, isosorbide: 500.1 g; diphenyl carbonate: 1095.6 g; and an aqueous solution of magnesium acetate tetrahydrate: 8.7 mL (concentration: 8.4 g/L, magnesium acetate tetrahydrate: 73 mg) were put into a 5 L glass separable flask, which was equipped with an agitator, a distillation trap, and a pressure adjusting device, and nitrogen gas replacement was conducted. The content was firstly heated to 130° C. at its internal temperature for dissolution. When it was heated and dissolved, the pressure was reduced down to 5.33 kPa in 5 min. to react it at 130° C. for 180 min. at 5.33 kPa by distilling and removing the phenol. Then the pressure was reduced down to 0.40 kPa in 120 min., and then the temperature was raised to 160° C. in 70 min. to react it while distilling and removing the phenol and unreacted diol. The obtained polycarbonate diol product was 970.0 g. The contained magnesium amount was 9.35 weight ppm.

Moreover, a thin-film distilling was conducted for the obtained polycarbonate diol product at flow rate of 20 g/min. (temperature: 180 to 200° C., pressure: 0.027 kPa).

The number average molecular weight (Mn) obtained after this thin-film distilling from NMR analysis of the polycarbonate diol contained in this polycarbonate diol product was 980, (A)/(B) ratio (isosorbide/1,6-hexanediol) was 50/50, Terminal (A)/(B) ratio (terminal isosorbide/1,6- hexanediol ratio) was 70/30, and the terminal (A) ratio (I) calculated by the aforementioned (I) was 1.40.

The property of obtained polycarbonate diol product was a transparent solid at a room temperature and the contained magnesium amount was 9.97 weight ppm. APHA value was 60, and the amount of raw diol isosorbide was 0.60 weight %, phenol amount was 0.04 weight %, and a polymer which became a phenoxide terminal and a polymer containing an ether bond other than isosorbide skeleton were not detected. Remaining diphenyl carbonate was lower than the quantitation limit (lower than 0.01 weight %).

Experimental Example 8-1

1,6-hexanediol: 404.3 g, isosorbide: 500.1 g, diphenyl carbonate: 1095.6 g, and an aqueous solution of magnesium acetate tetrahydrate: 17.5 mL (concentration: 8.4 g/L, magnesium acetate tetrahydrate: 147 mg) were put into a 5 L glass separable flask, which was equipped with an agitator, a distillation trap, and a pressure adjusting device, and nitrogen gas replacement was conducted. The content was firstly heated to 130° C. at its internal temperature for dissolution. When it was heated and dissolved, the pressure was reduced down to 5.33 kPa in 5 min. to react it at 130° C. for 150 min. at 5.33 kPa by distilling and removing the phenol. Then the pressure was reduced down to 0.40 kPa in 110 min., and then the temperature was raised to 160° C. in 60 min. to react it while distilling and removing the phenol and unreacted diol. The obtained polycarbonate diol product was 972.5 g. The contained magnesium amount was 17.5 weight ppm.

The number average molecular weight (Mn) obtained from NMR analysis of the polycarbonate diol contained in this polycarbonate diol product was 924, (A)/(B) ratio (isosorbide/1,6-hexanediol) was 50/50, Terminal (A)/(B) ratio (terminal isosorbide/1,6-hexanediol ratio) was 70/30, and the terminal (A) ratio (I) calculated by the aforementioned (I) was 1.40.

The property of obtained polycarbonate diol product was a transparent solid at room temperature. APHA value was 60, and the amount of raw diol isosorbide was 3.91 weight %, phenol amount was 1.17 weight %, and a polymer which became a phenoxide terminal and a polymer containing an ether bond other than isosorbide skeleton were not detected. Remaining diphenyl carbonate was lower than the quantitation limit (lower than 0.01 weight %).

Experimental Example 9-1

1,6-hexanediol: 404.3 g, isosorbide: 500.1 g, diphenyl carbonate: 1095.6 g, and an aqueous solution of magnesium acetate tetrahydrate: 8.7 mL (concentration: 50.4 g/L, magnesium acetate tetrahydrate: 440 mg) were put into a 5 L glass separable flask, which was equipped with an agitator, a distillation trap, and a pressure adjusting device, and nitrogen gas replacement was conducted. The content was firstly heated to 130° C. at its internal temperature for dissolution. When it was heated and dissolved, the pressure was reduced down to 6.67 kPa in 5 min. to react it at 130° C. for 150 min. at 6.67 kPa by distilling and removing the phenol. Then the pressure was reduced down to 0.40 kPa in 210 min., and then the temperature was raised to 160° C. in 100 min. to react it while distilling and removing the phenol and unreacted diol. The obtained polycarbonate diol product was 987.0 g. The contained magnesium amount was 65.9 weight ppm. The property of obtained polycarbonate diol product was a transparent solid at a room temperature and contained a white Mg salt agglomerate.

A thin-film distilling was conducted for the obtained polycarbonate diol product at flow rate of 20 g/min. (temperature: 180 to 200° C., Pressure: 0.027 kPa).

The number average molecular weight (Mn) obtained after this thin-film distilling from NMR analysis of the polycarbonate diol contained in this polycarbonate diol product was 1,067, (A)/(B) ratio (isosorbide/1,6-hexanediol) was 46/54, Terminal (A)/(B) ratio (terminal isosorbide/1,6-hexanediol ratio) was 85/15, and the terminal (A) ratio (I) calculated by the aforementioned (I) was 1.85.

The property of obtained polycarbonate diol product after this thin-film distilling was a transparent solid at a room temperature and the contained magnesium amount was 49.3 weight ppm. APHA value was 70, and the amount of raw diol isosorbide was 1.66 weight %, and phenol, a polymer which became a phenoxide terminal and a polymer containing an ether bond other than isosorbide skeleton were not detected. Remaining diphenyl carbonate was lower than the quantitation limit (lower than 0.01 weight %).

Experimental Example 10-1

1,6-hexanediol: 404.3 g, isosorbide: 500.1 g, diphenyl carbonate: 1095.6 g, and an aqueous solution of magnesium acetate tetrahydrate: 8.7 mL (concentration: 100.8 g/L, magnesium acetate tetrahydrate: 877 mg) were put into a 5 L glass separable flask, which was equipped with an agitator, a distillation trap, and a pressure adjusting device, and nitrogen gas replacement was conducted. The content was firstly heated to 130° C. at its internal temperature for dissolution. When it was heated and dissolved, the pressure was reduced down to 6.67 kPa in 5 min. to react it at 130° C. for 150 min. at 6.67 kPa by distilling and removing the phenol. Then the pressure was reduced down to 0.40 kPa in 180 min., and then the temperature was raised to 160° C. in 100 min. to distill and remove the phenol and unreacted diol. The obtained polycarbonate diol product was 986.9 g. The obtained magnesium content was 113 weight ppm. The property of obtained polycarbonate diol product was a transparent solid at a room temperature and contained a white Mg salt agglomerate.

A thin-film distilling was conducted for the obtained polycarbonate diol product at flow rate of 20 g/min. (temperature: 180 to 200° C., Pressure: 0.027 kPa).

The number average molecular weight (Mn) obtained after this thin-film distilling from NMR analysis of the polycarbonate diol contained in this polycarbonate diol product was 1,054, (A)/(B) ratio (isosorbide/1,6-hexanediol) was 46/54, Terminal (A)/(B) ratio (terminal isosorbide/1,6-hexanediol ratio) was 90/10, and the terminal (A) ratio (I) calculated by the aforementioned (I) was 1.96.

The property of polycarbonate diol after this thin-film distilling was a transparent solid at a room temperature and the contained magnesium amount was 104 weight ppm. APHA value was 60, and the amount of raw diol isosorbide was 1.47 weight %, and phenol, a polymer which became phenoxide terminal and a polymer containing an ether bond other than skeleton were not detected. Remaining diphenyl carbonate was lower than the quantitation limit (lower than 0.01 weight %).

Experimental Example 11-1

1,6-hexanediol: 404.3 g, isosorbide: 500.1 g, diphenyl carbonate: 1095.6 g, and aqueous calcium acetate solution:

7.2 mL (concentration: 8.4 g/L, calcium acetate: 61 mg) were put into a 5 L glass separable flask, which was equipped with an agitator, a distillation fluid trap, and a pressure adjusting device, and nitrogen gas replacement was conducted. The content was firstly heated to 130° C. at its internal temperature for dissolution. When it was heated and dissolved, the pressure was reduced down to 4.67 kPa in 5 min. to react it at 130° C. for 140 min. at 4.67 kPa by distilling and removing the phenol. Then the pressure was reduced down to 0.40 kPa in 80 min., and then the temperature was raised to 160° C. in 120 min. to distill and remove the phenol and unreacted diol. The obtained polycarbonate diol product was 926.4 g.

The number average molecular weight (Mn) obtained from NMR analysis of the polycarbonate diol contained in this polycarbonate diol product was 1,130, (A)/(B) ratio (isosorbide/1,6-hexanediol) was 50/50, Terminal (A)/(B) ratio (terminal isosorbide/1,6-hexanediol ratio) was 92/8, and the terminal (A) ratio (I) calculated by the aforementioned (I) was 1.84.

The property of obtained polycarbonate diol product was a transparent solid at room temperature. APHA value was 60, and the amount of raw diol isosorbide was 4.29 weight %, phenol amount was 0.23 weight %, and a polymer which became a phenoxide terminal and a polymer containing an ether bond other than isosorbide skeleton were not detected. Remaining diphenyl carbonate was lower than the quantitation limit (lower than 0.01 weight %).

Experimental Example 12-1

1,6-hexanediol: 404.3 g, isosorbide: 500.1 g, diphenyl carbonate: 1095.6 g, and aqueous barium acetate solution: 10.4 mL (concentration: 8.4 g/L, barium acetate: 87 mg) were put into a 5 L glass separable flask, which was equipped with an agitator, a distillation trap, and a pressure adjusting device, and nitrogen gas replacement was conducted. The content was firstly heated to 130° C. at its internal temperature for dissolution. When it was heated and dissolved, the pressure was reduced down to 5.33 kPa in 5 min. to react it at 130° C. for 180 min. at 5.33 kPa by distilling and removing the phenol. Then the pressure was reduced down to 0.40 kPa in 100 min., and then the temperature was raised to 160° C. in 80 min. to distill and remove the phenol and unreacted diol. The obtained polycarbonate diol product was 964.8 g.

The number average molecular weight (Mn) obtained from NMR analysis of the polycarbonate diol contained in this polycarbonate diol product was 1,028, (A)/(B) ratio (isosorbide/1,6-hexanediol) was 48/52, Terminal (A)/(B) ratio (terminal isosorbide/1,6-hexanediol ratio) was 92/8, and the terminal (A) ratio (I) calculated by the aforementioned (I) was 1.92.

The property of obtained polycarbonate diol product was a transparent solid at room temperature. APHA value was 60, and the amount of raw diol isosorbide was 5.68 weight %, phenol amount was 0.70 weight %, and a polymer which became a phenoxide terminal and a polymer containing an ether bond other than isosorbide skeleton were not detected. Remaining diphenyl carbonate was lower than the quantitation limit (lower than 0.01 weight %).

Experimental Example 13-1

1,6-hexanediol: 404.3 g, isosorbide: 500.1 g, diphenyl carbonate: 1095.6 g, and sodium acetate: 3.3 mL (concentration: 8.4 g/L, sodium acetate: 28 mg) were put into a 5 L glass separable flask, which was equipped with an agitator, a distillation trap, and a pressure adjusting device, and nitrogen gas replacement was conducted. The content was firstly heated to 130° C. at its internal temperature for dissolution. When it was heated and dissolved, the pressure was reduced down to 5.33 kPa in 5 min. to react it at 130° C. for 280 min. at 5.33 kPa by distilling and removing the phenol. Then the pressure was reduced down to 0.40 kPa in 240 min., and then the temperature was raised to 160° C. in 60 min. to distill and remove the phenol and unreacted diol at 0.40 kPa for 30 min. at 160° C. The obtained polycarbonate diol product was 957.0 g.

The number average molecular weight (Mn) obtained from NMR analysis of the polycarbonate diol contained in this polycarbonate diol product was 1,053, (A)/(B) ratio (isosorbide/1,6-hexanediol) was 49/51, Terminal (A)/(B) ratio (terminal isosorbide/1,6-hexanediol ratio) was 90/10, and the terminal (A) ratio (I) calculated by the aforementioned (I) was 1.84.

The property of obtained polycarbonate diol product was a transparent solid at room temperature. APHA value was 60, and the amount of raw diol isosorbide was 5.25 weight %, phenol amount was 0.43 weight %, and a polymer which became a phenoxide terminal and a polymer containing an ether bond other than isosorbide skeleton were not detected. Remaining diphenyl carbonate was lower than the quantitation limit (lower than 0.01 weight %).

Reference Experimental Example 6-1

1,6-hexanediol: 404.3 g, isosorbide: 500.1 g, diphenyl carbonate: 1095.6 g, and an aqueous solution of magnesium acetate tetrahydrate solution: 8.7 mL (concentration: 336.0 g/L, magnesium acetate tetrahydrate: 2,923 mg) were put into a 5 L glass separable flask, which was equipped with an agitator, a distillation trap, and a pressure adjusting device, and nitrogen gas replacement was conducted. The content was firstly heated to 130° C. at its internal temperature for dissolution. When it was heated and dissolved, the pressure was reduced down to 6.67 kPa in 5 min. to react it at 130° C. for 190 min. at 5.33 to 8.00 kPa by distilling and removing the phenol. Then the pressure was reduced down to 0.40 kPa in 100 min., and then the temperature was raised to 150° C. in 60 min. to distill and remove the phenol and unreacted diol. The obtained polycarbonate diol product was 990.0 g. The obtained magnesium content was 315 weight ppm. The property of obtained polycarbonate diol product was a transparent solid at a room temperature and contained a white Mg salt agglomerate.

A thin-film distilling was conducted for the obtained polycarbonate diol product at flow rate of 20 g/min. (temperature: 180 to 200° C., Pressure: 0.027 kPa).

The number average molecular weight (Mn) obtained after this thin-film distilling from NMR analysis of the polycarbonate diol contained in this polycarbonate diol product was 1,122, (A)/(B) ratio (isosorbide/1,6-hexanediol) was 45/55, Terminal (A)/(B) ratio (terminal isosorbide/1,6-hexanediol ratio) was 90/10, and the terminal (A) ratio (I) calculated by the aforementioned (I) was 2.00.

The property of obtained polycarbonate diol product after this thin-film distilling was a transparent solid at a room temperature and the contained magnesium amount was 350 weight ppm. APHA value was 70, and the amount of raw diol isosorbide was 2.97 weight %, and phenol, a polymer which became a phenoxide terminal and a polymer containing an ether bond other than isosorbide structure were not detected. Remaining diphenyl carbonate was lower than the quantitation limit (lower than 0.01 weight %).

Reference Experimental Example 7-1

1,6-hexanediol: 404.3 g, isosorbide: 500.1 g, diphenyl carbonate: 1095.6 g, and an aqueous solution of magnesium acetate tetrahydrate: 0.051 mL (concentration: 8.4 g/L, magnesium acetate tetrahydrate: 0.4 mg) into a 5 L glass separable flask, which was equipped with an agitator, a distillation trap, and a pressure adjusting device, for nitrogen gas replacement. The content was firstly heated to 130° C. at its internal temperature for dissolution. When it was heated and dissolved, the pressure is reduced down to 6.67 kPa in 5 min. to react it at 130° C. for 100 min. at 6.67 kPa. Then the pressure was reduced down to 2.67 kPa in 30 min. to react it at 2.67 kPa for 340 min. at 130° C. About 5 mL distillated objects were found and little phenol generation was recognized in the system, therefore the reaction was stopped. A mixture after the reaction showed the almost the same weight as the added raw material, so the contained Mg amount was considered to be 0.07 ppm (theoretical value).

Reference Experimental Example 8-1

1,6-hexanediol: 404.3 g, isosorbide: 500.1 g, diphenyl carbonate: 1095.6 g, and an aqueous solution of magnesium acetate tetrahydrate: 8.7 mL (concentration: 8.4 g/L, magnesium acetate tetrahydrate: 73 mg) were put into a 5 L glass separable flask, which was equipped with an agitator, a distillation trap, and a pressure adjusting device, and nitrogen gas displacement was conducted. The content is firstly heated to 130° C. at its internal temperature for dissolution. When it was heated and dissolved, the pressure was reduced down to 6.67 kPa in 5 min. to react it at 130° C. for 240 min. at 5.33 to 6.67 kPa by distilling and removing the phenol. Then the pressure was reduced down to 0.40 kPa in 140 min., and then the temperature was raised to 180° C. in 60 min. to distill and remove the phenol and unreacted diol at 0.40 kPa for 280 min. at 180° C. The property of the obtained polycarbonate diol product was a transparent solid at room temperature, and its yield was 906.4 g. The contained magnesium amount was 9.43 weight ppm.

A thin-film distilling was conducted for the obtained polycarbonate diol product at flow rate of 20 g/min. (temperature: 180 to 200° C., Pressure: 0.027 kPa).

The number average molecular weight (Mn) obtained after this thin-film distilling from NMR analysis of the polycarbonate diol contained in this polycarbonate diol product is 1,082, (A)/(B) ratio (isosorbide/1,6-hexanediol) was 47/53, Terminal (A)/(B) ratio (terminal isosorbide/1,6-hexanediol ratio) was 92/8, and the terminal (A) ratio (I) calculated by the aforementioned (I) was 1.96.

The property of the obtained polycarbonate diol product after this thin-film distilling was a transparent solid at a room temperature and the contained magnesium amount was 9.97 ppm. APHA value was 100, and the amount of raw diol isosorbide was 1.08 weight %, and phenol, a polymer which became or a phenoxide terminal and a polymer containing an ether bond other than isosorbide structure were not detected. Remaining diphenyl carbonate was lower than the quantitation limit (lower than 0.01 weight %).

Reference Experimental Example 9-1

1,6-hexanediol: 404.3 g, isosorbide: 500.1 g, diphenyl carbonate: 1095.6 g, and zinc acetate: 62.8 mg were put into a 5 L glass separable flask, which was equipped with an agitator, a distillation trap, and a pressure adjusting device, and nitrogen gas replacement was conducted. The content was firstly heated to 130° C. at its internal temperature for dissolution. When it was dissolved, the pressure was reduced down to 6.67 kPa in 5 min. to react it at 130° C. for 210 min. at 6.67 kPa by distilling and removing the phenol. Then the pressure was reduced down to 0.40 kPa in 390 min., and then the temperature was raised to 160° C. in 90 min. to react it while distilling and removing the phenol at 0.40 kPa for 50 min. at 160° C. The obtained polycarbonate diol product was 943.4 g.

The number average molecular weight (Mn) obtained from NMR analysis of the polycarbonate diol contained in this polycarbonate dial product is 1,021, (A)/(B) ratio (isosorbide/1,6-hexanediol) was 48/52, Terminal (A)/(B) ratio (terminal isosorbide/1,6-hexanediol ratio) was 85/15, and the terminal (A) ratio (I) calculated by the aforementioned (I) was 1.77.

The property of obtained polycarbonate diol product was a yellow solid with white turbidity at room temperature. APHA could not be measured due to white turbidity. The amount of raw diol isosorbide was 4.77 weight %, phenol amount was 0.41 weight %, and a polymer which became a phenoxide terminal and a polymer containing an ether bond other than isosorbide skeleton were not detected. Remaining diphenyl carbonate was lower than the quantitation limit (lower than 0.01 weight %).

Reference Experimental Example 10-1

1,6-hexanediol: 404.3 g, isosorbide: 500.1 g, diphenyl carbonate: 1095.6 g, and zinc acetate: 345 mg were put into a 5 L glass separable flask, which was equipped with an agitator, a distillation trap, and a pressure adjusting device, and nitrogen gas replacement was conducted. The content was firstly heated to 130° C. at its internal temperature for dissolution. When it was dissolved, the pressure was reduced down to 6.67 kPa in 5 min. to react it at 130-140° C. for 330 min. at 6.67 kPa by distilling and removing the phenol. Then the temperature was raised to 165° C. in 210 min. at the pressure of 4.67 to 8.67 kPa to distill and remove the phenol. Then the pressure was reduced down to 0.40 kPa in 30 min. and the temperature was raised to 190° C. in 120 min. to distill and remove the phenol. The obtained polycarbonate diol product was 922.2 g.

A thin-film distilling was conducted for the obtained polycarbonate diol product at flow rate of 20 g/min. (temperature: 180 to 200° C., Pressure: 0.027 kPa).

The number average molecular weight (Mn) obtained after this thin-film distilling from NMR analysis of the polycarbonate diol contained in this polycarbonate diol product was 1,088, (A)/(B) ratio (isosorbide/1,6-hexanediol) was 46/54, Terminal (A)/(B) ratio (terminal isosorbide/1,6-hexanediol ratio) was 93/7, and the terminal (A) ratio (I) calculated by the aforementioned (I) was 2.02.

The property of obtained polycarbonate diol product was a yellow solid with white turbidity at room temperature. APHA could not be measured due to white turbidity. The amount of raw diol isosorbide was 0.30 weight %, and phenol, a polymer which became phenoxide terminal and a polymer containing an ether bond other than isosorbide structure were not detected. Remaining diphenyl carbonate was lower than the quantitation limit (lower than 0.01 weight %).

Experimental Example 5-4

95.6 g of the polycarbonate diol after thin-film distilling which was obtained in the Experimental example 5-1 was preheated to a melting point or higher (ex. 150° C.) and added to a separable flask, the flask was placed in an oil bath set at 50° C. to heat and 134 g of DMF was added to dissolve it. During agitation at 100 rpm, 14.0 g of MDI was added. Then an agitation torque's voltage value change due to increase in viscosity was read and the aspect of the content was observed.

In this case, it took very long time for polymerization, and its torque was only 0.2 V even in one hour later. Even in four hours later, its viscosity was increased little by little, but the torque was about 0.7 V.

Experimental Example 7-4

85.0 g of the polycarbonate diol after thin-film distilling which was obtained in the Experimental example 7-1 was preheated to a melting point or higher (ex. 100° C.) and added to a separable flask, the flask was placed in an oil bath set at 50° C. to heat and 131 g of DMF was added to dissolve it. During agitation at 100 rpm, 21.9 g of MDI was added. Then an agitation torque's voltage value change due to increase in viscosity was read and the aspect of the content was observed.

In this case, it took about 42 min. to exceed the torque 1.0 V and the viscosity increase speed was easily-handled range. Then the viscosity slowly increased and the increase stopped at the torque of about 1.7 V.

Experimental Example 9-4

84.9 g of the polycarbonate diol after thin-film distilling which was obtained in the Experimental example 9-1 was preheated to a melting point or higher (ex. 100° C.) and added to a separable flask, the flask was placed in an oil bath set at 50° C. to heat and 131 g of DMF was added to dissolve it. During agitation at 100 rpm, 22.1 g of MDI was added. Then an agitation torque's voltage value change due to increase in viscosity was read and the aspect of the content was observed.

In this case, it took about 14 min. to exceed the torque 1.0 V and the viscosity increase speed was in an easily-handled range. Then the viscosity slowly increased and the increase stopped at the torque of about 1.8 V.

Experimental Example 10-4

85.0 g of the polycarbonate diol after thin-film distilling which was obtained in the Experimental example 10-1 was preheated to a melting point or higher (ex. 100° C.) and added to a separable flask, the flask was placed in an oil bath set at 50° C. to heat and 129 g of DMF was added to dissolve it. During agitation at 100 rpm, 20.9 g of MDI was added. Then an agitation torque's voltage value change due to increase in viscosity was read and the aspect of the content was observed.

In this case, a certain amount of gel was formed right after MDI being added, but as a whole this was an easy-handling polymerized solution. It took about 10 min. to exceed the torque 0.7 V and the viscosity increase speed was in an easily-handled range.

However, the gel forming resulted in a heterogeneous solution and low viscosity was partially recognized, so the torque did not exceed 1.0 V.

Reference Experimental Example 6-4

85.0 g of the polycarbonate diol after thin-film distilling which was obtained in the Reference Experimental example 6-1 was preheated to a melting point or higher (ex. 100° C.) and added to a separable flask, the flask was placed in an oil bath set at 50° C. to heat and 132 g of DMF was added to dissolve it. During agitation at 100 rpm, 22.8 g of MDI was added. (Actual experiment was conducted at 50% solute. No result change was expected, so the solvent amount had been changed from 108 g to 45%.)

In this case, a great amount of gel was formed right after MDI addition, and almost all amount was stuck to an agitation wing to be like a ball. Therefore, measuring the viscosity increase speed was impossible.

Reference Experimental Example 8-4

85.0 g of the polycarbonate diol after thin-film distilling which was obtained in the Reference Experimental example 8-1 was preheated to a melting point or higher (ex. 100° C.) and added to a separable flask, the flask was placed in an oil bath set at 50° C. to heat and 129 g of DMF was added to dissolve it. During agitation at 100 rpm, 20.6 g of MDI was added. Then an agitation torque's voltage value change due to increase in viscosity was read and the aspect of the content was observed.

In this case, it took about 16 min. to exceed the torque 1.0 V, then in about 19 min. later, the value reached 2.7 V, and then a surge was recognized and it became unmeasurable.

Reference Experimental Example 10-4

65.0 g of the polycarbonate diol after thin-film distilling which was obtained in the Reference Experimental example 10-1 was preheated to a melting point or higher (ex. 100° C.) and added to a separable flask, the flask was placed in an oil bath set at 50° C. to heat and 146 g of DMF was added to dissolve it. During agitation at 100 rpm, 13.7 g of MDI was added. Then an agitation torque's voltage value change due to viscosity increase was read and an aspect of the content was observed (this was a condition for 35% solute).

In this case, it took about 32 min. to exceed the torque 1.0 V, and the viscosity increase speed was in an easily-handled range. Then the viscosity slowly increased and the increase stopped at the torque of about 1.7 V.

[Consideration of Amount of Catalyst and Urethanization Reaction Speed]

Tables 6 and 7 show summaries of the amount of the raw material diol which was used in producing the polycarbonate diol, types of catalyst, amount of catalyst, yield and reaction time, the catalyst amount contained in a polycarbonate diol product, and whether a catalyst-derived metallic salt aggregate exists or not, and results of urethanization reaction speed tests with a polycarbonate diol product being used, about the aforementioned Experimental examples 5-1 to 13-1, the aforementioned Reference Experimental examples 6-1, 7-1, 9-1 and 10-1. In Tables 6 and 7, the amount of catalyst indicates a concentration in a weight against the used diol amount. In Table 6, "*" indicates a theoretical value. In Tables 6 and 7, a parenthetical numerical value about the amount of catalyst indicates a value before thin-film distillation is done.

TABLE 6

| | | Example 7 | Example 8 | Example 9 | Example 10 | Example 11 |
|---|---|---|---|---|---|---|
| Experimental example No./Reference experimental example No. | | Experimental example 5-1 | Experimental example 6-1 | Experimental example 7-1 | Experimental example 8-1 | Experimental example 9-1 |
| Row materials Diol [mol %] | 16 HD | 50 | 50 | 50 | 50 | 50 |
| | ISB | 50 | 50 | 50 | 50 | 50 |
| Catalyst | Type | $Mg(OAc)_2 \cdot 4H_2O$ | $Mg(OAc)_2 \cdot 4H_2O$ | $Mg(OAc)_2 \cdot 4H_2O$ | $Mg(OAc)_2 \cdot 4H_2O$ | $Mg(OAc)_2 \cdot 4H_2O$ |
| | Used amount [ppm] | 0.9 | 4.6 | 9.1 | 18.4 | 46 |
| Reactivity | Yield [%] | 77.6 | 93.3 | 93.5 | 93.9 | 95.1 |
| | Time [min] | 454 | 427 | 416 | 373 | 502 |
| Physical properties | Contained amont of catalyst [ppm] (Before thin-film distillation) | 1.14 (1.06) | — (4.29) | 9.97 (9.35) | — (17.5) | 49.3 (65.9) |
| | Existence of metallic salt aggregates | None | None | None | None | Exists |
| Experimental example No./Reference experimental example No. | | Experimental example 5-4 | — | Experimental example 7-4 | — | Experimental example 9-4 |
| Urethanization reaction rate | Time till 0.7 V [min] | Approx. 240 | — | 33 | — | 10 |
| | Time till 1.0 V [min] | — | — | 42 | — | 14 |
| | Load value at 30 min [V] | 0.12 | — | 0.57 | — | 1.60 |
| | Load value at 60 min [V] | 0.21 | — | 1.50 | — | 1.80 |
| | Final load value [V] | 0.70 | — | 1.70 | — | 1.80 |

| | | Example 12 | Example 13 | Example 14 | Example 15 |
|---|---|---|---|---|---|
| Experimental example No./Reference experimental example No. | | Experimental example 11-1 | Experimental example 12-1 | Experimental example 13-1 | Reference experimental example 7-1 |
| Row materials Diol [mol %] | 16 HD | 50 | 50 | 50 | 50 |
| | ISB | 50 | 50 | 50 | 50 |
| Catalyst | Type | $Ca(OAc)_2 \cdot H_2O$ | $Ba(OAc)_2 \cdot H_2O$ | NaOAc | $Mg(OAc)_2 \cdot 4H_2O$ |
| | Used amount [ppm] | 15.2 | 51.9 | 8.7 | 0.05 |
| Reactivity | Yield [%] | 89.3 | 93 | 92.3 | — |
| | Time [min] | 388 | 412 | 661 | — |
| Physical properties | Contained amont of catalyst [ppm] (Before thin-film distillation) | — | — | — | — (0.07)* |
| | Existence of metallic salt aggregates | None | None | None | — |
| Experimental example No./Reference experimental example No. | | — | — | — | — |
| Urethanization reaction rate | Time till 0.7 V [min] | — | — | — | — |
| | Time till 1.0 V [min] | — | — | — | — |
| | Load value at 30 min [V] | — | — | — | — |
| | Load value at 60 min [V] | — | — | — | — |
| | Final load value [V] | — | — | — | — |

TABLE 7

| | | Reference example 1 | Reference example 2 | Reference example 3 | Reference example 4 |
|---|---|---|---|---|---|
| Experimental example No./Reference experimental example No. | | Experimental example 10-1 | Reference experimental example 6-1 | Reference experimental example 9-1 | Reference experimental example 10-1 |
| Row materials Diol [mol %] | 16 HD | 50 | 50 | 50 | 50 |
| | ISB | 50 | 50 | 50 | 50 |
| Catalyst | Type | $Mg(OAc)_2 \cdot 4H_2O$ | $Mg(OAc)_2 \cdot 4H_2O$ | $Zn(OAc)_2$ | $Zn(OAc)_2$ |
| | Used amount [ppm] | 110 | 368 | 24.8 | 136 |
| Reactivity | Yield [%] | 95.1 | 95.4 | 90.9 | 88.9 |
| | Time [min] | 473 | 405 | 740 | 828 |
| Physical properties | Contained amount of catalyst [ppm] (Before thin-film distillation) | 104 (113) | 350 (315) | — | — |
| | Existance of metallic salt aggregates | Exists | Exists | — | — |

TABLE 7-continued

|  |  | Reference example 1 | Reference example 2 | Reference example 3 | Reference example 4 |
|---|---|---|---|---|---|
|  | Experimental example No./Reference experimental example No. | Experimental example 10-4 | Reference experimental example 6-4 | — | — |
| Urethanization reaction rate | Time till 0.7 V [min] | 7 | — | — | — |
|  | Time till 1.0 V [min] | — | — | — | — |
|  | Load value at 30 min [V] | 0.80 | — | — | — |
|  | Load value at 60 min [V] | 0.82 | — | — | — |
|  | Final load value [V] | <1.0 (partial gelatification) | (promptly, strong gelatification) | — | — |

As is clear from comparison of Examples 7 to 15 with Reference examples 3 and 4, relative to a case in which a compound using a metal of Group 9 on the periodic table as a transesterification catalyst, when a compound using a metal of Group 1 or 2 on the periodic table was used, the reaction speed of the transesterification catalyst could be accelerated to be able to obtain a polycarbonate diol product in a short time.

Furthermore, as is clear from comparison of Examples 7, 9 and 11 with Reference examples 1 and 2, by using a polycarbonate diol product which was obtained in such a short time and contained 100 ppm or less of catalyst, gelation could be suppressed and a homogenerous urethane could be obtained, while by using a polycarbonate diol product which contained 100 ppm or more catalyst for urethanization as shown in Reference examples 1 and 2, the urethanization reaction was further promoted than expected and gelation was accelerated, which did not result in a homogeneous polyurethane. In particular, in Reference example 2, a large amount of gel was formed right after MDI addition, and the test could not be continued, while in Reference example 1, it exceeded Load value 0.7 V in only 10 min., the viscosity increase stopped, but gel was formed right after MDI addition, and the urethane solution after the experiment was an inhomogeneous solution.

On the other hand, as is clear from comparison of Example 7 with Example 15, obtaining a polycarbonate diol product containing small amount of catalyst such as less than 0.1 ppm was difficult to obtain by a transesterification catalyst, because reactivity of diol and carbonate ester were not improved enough, and little reaction progress was recognized. However, for example, by purifying a polycarbonate diol containing 0.1 ppm or more of catalyst, controlling the amount to be less than 0.1 ppm is possible. By using such a polycarbonate diol for urethanization, it is possible to suppress gelation and obtain a homogeneous urethane.

[Consideration of Terminal A Rate (I) and Urethanization Reaction Speed]

Tables 8 shows summaries of the amount of the raw material diol which was used in producing the polycarbonate diol, types of catalyst, amount of catalyst, yield, the highest reaction temperature and reaction time, Terminal (A) ratio (I) in a polycarbonate diol product, and results of urethanization reaction speed tests with a polycarbonate diol product being used, about the aforementioned Experimental examples 5-1, 7-1, 9-1, the aforementioned Reference Experimental examples 8-1 and 10-1.

TABLE 8

|  |  | Example 16 | Example 17 | Reference example 5 | Reference example 6 |
|---|---|---|---|---|---|
|  | Experimental example No./Reference experimental example No. | Experimental example 7-1 | Experimental example 9-1 | Experimental example 5-1 | Reference experimental example 8-1 |
| Row materials Diol [mol %] | 16 HD | 50 | 50 | 50 | 50 |
|  | ISB | 50 | 50 | 50 | 50 |
| Catalyst | Type | $Mg(OAc)_2 \cdot 4H_2O$ | $Mg(OAc)_2 \cdot 4H_2O$ | $Mg(OAc)_2 \cdot 4H_2O$ | $Mg(OAc)_2 \cdot 4H_2O$ |
|  | Used amount [ppm] | 9.1 | 46 | 0.9 | 9.1 |
| Reactivity | Yield [%] | 93.5 | 95.1 | 77.6 | 87.4 |
|  | Highest temperature [° C.] | 160 | 160 | 160 | 180 |
|  | Time [min] | 416 | 502 | 454 | 770 |
| Physical properties | Formula (I) | 1.40 | 1.85 | 1.11 | 1.96 |
|  | Experimental example No./Reference experimental example No. | Experimental example 7-4 | Experimental example 9-4 | Experimental example 5-4 | Reference experimental example 8-4 |
| Urethanization reaction rate | Time till 0.7 V [min] | 33 | 10 | Approx. 240 | 14 |
|  | Time till 1.0 V [min] | 42 | 14 | — | 16 |
|  | Load value at 30 min [V] | 0.57 | 1.6 | 0.12 | — |
|  | Load value at 60 min [V] | 1.50 | 1.80 | 0.21 | — |
|  | Final load value [V] | 1.70 | 1.80 | 0.70 | — |

As it is clear from a comparison of Examples 16 and 17 with Reference example 5, when an polycarbonate diol product having Terminal (A) ratio (I) is 1.2 or more was used, it had an appropriate urethanization reaction speed and urethanization reaction could be processed enough to obtain a polyurethane with designed physical properties. On the other hand, it was found that when a polycarbonate diol product having 1.2 or less of Terminal (A) ratio (I) was used, urethanization reaction speed was too slow to process urethanization reaction, and a polyurethane with designed physical proparties such as hardness might not be obtained. Specifically, when a polycarbonate diol product having 1.2 or less of Terminal (A) ratio (I) of Reference example 5 was used, its urethanization reaction speed was slow and it took about 4 hours for its load value to exceed 0.7 V, and its final load value reached only 1.0 V or less. On the other hand, when a polycarbonate diol product having 1.2 or more of Terminal (A) ratio (I) of Examples 16 and 17 was used, it had an appropriate urethanization reaction speed, and urethanization reaction could be processed enough, while its load value exceeds 0.7 V within 60 min. and its final load value exceeded 1.0 V and then the viscosity increase stopped.

On the other hand, as is clear from a comparison of Example 16 and 17 with Reference example 6, when an polycarbonate diol product having Terminal (A) ratio (I) was 1.9 or less was used, it had an appropriate urethanization reaction speed and controlled urethanization reaction could be processed enough to obtain a polyurethane having designed physical properties. Also, it was found that when a polycarbonate diol product having more than 1.9 of Terminal (A) ratio (I) was used, urethanization reaction was processed too much due to its excessive velocity of the reaction, and therefore a polyurethane having designed physical properties such as hardness might not be obtained. Specifically, by comparing Example 16 with Reference example 6, even if they had the same amount of catalysts, but urethanization reaction speed largely differed due to the difference of Terminal (A) ratio (I), and it is obvious that the Terminal (A) ratio (I) largely affects its urethanization reaction speed. When a polycarbonate diol product having 1.9 or more of Terminal (A) ratio (I) of Reference example 6 was used, due to its excessive velocity of the urethanization reaction its viscosity increase did not stop after the load value reached 0.7 V in 14 min. and the viscosity increased too high to measure its final load value.

[Consideration of Maximum Reaction Temperature and Urethanization Reaction Speed]

Tables 9 shows summaries of the amount of the raw material diol which was used in producing the polycarbonate diol, and types and amount of catalyst, yield, the highest reaction temperature and reaction time, Terminal (A) ratio (I) of a polycarbonate diol product, and results of urethanization reaction speed tests with a polycarbonate diol product being used, about the aforementioned Experimental examples 7-1 and the aforementioned Reference Experimental example 8-1.

TABLE 9

| | | Example 18 | Reference example 7 |
|---|---|---|---|
| Experimental example No./Reference experimental example No. | | Experimental example 7-1 | Reference experimental example 8-1 |
| Raw materials Diol [mol %] | 16 HD | 50 | 50 |
| | ISB | 50 | 50 |
| Catalyst | Type | Mg(OAc)$_2$•4H$_2$O | Mg(OAc)$_2$•4H$_2$O |
| | Used amount [ppm] | 9.1 | 9.1 |
| Reactivity | Yield [%] | 93.5 | 87.4 |
| | Highest temperature [° C.] | 160 | 180 |
| | Time [min] | 416 | 770 |
| Physical properties | Formula (I) | 1.40 | 1.96 |
| Experimental example No./Reference experimental example No. | | Experimental example 7-4 | Reference experimental example 8-4 |
| Urethanization reaction rate | Time till 0.7 V [min] | 33 | 14 |
| | Time till 1.0 V [min] | 42 | 16 |
| | Load value at 30 min [V] | 0.57 | — |
| | Load value at 60 min [V] | 1.50 | — |
| | Final load value [V] | 1.70 | — |

As is clear from a comparison of Example 18 with Reference example 7, when a polycarbonate diol product, which was obtained at the highest reaction temperature was less than 180° C. during producing, an appropriate Terminal (A) ratio (I) and urethanization reaction speed were obtained to process urethanization reaction appropriately and a polyurethane having designed physical property physical properties was obtained. On the other hand, it was found that a polycarbonate diol product obtained with the highest reaction temperature of 180° C. or higher during producing had a higher Terminal (A) ratio (I), while an urethanization reaction was conducted by using that product, its urethanization reaction speed was too high, the urethanization reaction was processed too much, its viscosity was increased too much to measure its load value, and a polyurethane having a designed physical properties such as hardness might not be obtained.

INDUSTRIAL APPLICABILITY

A polycarbonate diol of the present invention has a rigid structure (A) in a molecular chain, therefore a polyurethane produced by using the polycarbonate diol has high hardness, excellent abrasion resistance, and long-term maintenance of the surface aspect, so applications to coating agent, water-based paint, adhesive agent, synthetic leather, and artificial leather, for example is preferred. In addition, Structure (A) has a higher hydrophilic property, therefore a polyurethane produced by using the polycarbonate diol of the present invention is industrially quite useful because it can be appropriately used in an application in which an affinity to water is required, for example, an application for producing water-based paint material with smaller environmental load.

According to the present invention, by a simple method of irradiating an active energy ray, a cured film more excellent in mechanical strength and contamination resistance can be easily produced, so in a field for protecting a base material's surface by a cured film, for example, both further improved productivity and higher performance of cured film can be expected in producing the cured film by the above simple method.

While the invention has been described in detail and with reference to specific embodiments thereof, it will be apparent to one skilled in the art that various changes and modifications can be made therein without departing from the spirit and scope thereof.

This is a continuation of International Application PCT/JP2011/059206, filed on Apr. 13, 2011, and designated the U.S., (and claims priority from Japanese Patent Application No. 2010-093155, which was filed on Apr. 14, 2010 and Japanese Patent Application No. 2010-191858, which was filed on Aug. 30, 2010) the entire contents of which are incorporated herein by reference.

What is claimed is:

1. A polycarbonate diol, obtained by reacting (i) at least one diol selected from isosorbide, isomannide, and isoidide, (ii) a diol having 1 to 15 carbons which may contain a hetero atom, and (iii) a diester carbonate, wherein:
the reaction of (i), (ii), and (iii) is carried out in the presence of a transesterification catalyst;
the transesterification catalyst is either a compound containing a metal of Group 1 of the periodic table or a compound containing a metal of Group 2 of the periodic table;
the polycarbonate diol contains the transesterification catalyst in an amount of 100 ppm or less, calculated as a weight ratio of catalyst metal in the polycarbonate diol;
the number average molecular weight of the polycarbonate diol is 250 to 5,000;
at least part of a molecular chain of the polycarbonate diol contains a repeating unit (A)

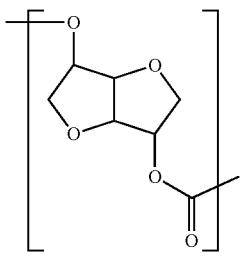

(A)

and a repeating unit (B)

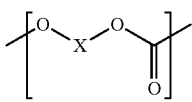

(B)

where X is a divalent group having 1 to 15 carbons which may contain a hetero atom; and the polycarbonate diol has a terminal (A) ratio (I) of 1.2 to 1.8, the terminal (A) ratio (I) being calculated by the following formula:

terminal (A) ratio (I)={(number of terminal units (A) in molecular chain)/(total number of terminal units (A) and terminal units (B) in molecular chain)}/{(number of units (A) in molecular chain)/(total number of units (A) and units (B) in molecular chain)}.

2. The polycarbonate diol according to claim 1, wherein the polycarbonate diol contains the transesterification catalyst in an amount of 0.1 to 100 ppm, calculated as a weight ratio of catalyst metal in the polycarbonate diol.

3. The polycarbonate diol according to claim 1, wherein the transesterification catalyst is a compound containing a metal of Group 2 of the periodic table.

4. The polycarbonate diol according to claim 1, wherein the highest temperature during the reaction of (i), (ii), and (iii) is less than 180° C.

5. The polycarbonate diol according to claim 1, wherein the number average molecular weight of the polycarbonate diol is 250 to 900.

6. A method for obtaining the polycarbonate diol of claim 1, comprising:
reacting (i) at least one diol selected from isosorbide, isomannide, and isoidide, (ii) a diol having 1 to 15 carbons which may contain a hetero atom, and (iii) a diester carbonate, in the presence of a transesterification catalyst, to obtain a polycarbonate diol:
wherein:
the transesterification catalyst is either a compound containing a metal of Group 1 of the periodic table or a compound containing a metal of Group 2 of the periodic table; and
the highest temperature during the reaction of (i), (ii), and (iii) is less than 180° C.

7. The method according to claim 6, wherein the transesterification catalyst is a compound containing a metal of Group 2 of the periodic table.

8. The polycarbonate diol according to claim 1, wherein the diester carbonate (iii) is diphenyl carbonate.

9. The polycarbonate diol according to claim 1, wherein the polycarbonate diol comprises unreacted diester carbonate in an amount of 1 weight % or less, based on the total weight of the polycarbonate diol.

10. The polycarbonate diol according to claim 1, wherein the diol (i) contains 20 ppm or less of formic acid.

11. The polycarbonate diol according to claim 1, wherein 5% or less of all molecular chain terminals of the polycarbonate diol are either an alkyloxy group or an aryloxy group.

12. The polycarbonate diol according to claim 1, wherein the Hazen color number value (APHA value: according to JIS K0071-1) of the polycarbonate diol is 100 or less.

13. The polycarbonate diol according to claim 1, wherein the molecular weight distribution (Mw/Mn) of the polycarbonate diol is 1.5 to 3.5.

14. A method, comprising:
reacting the polycarbonate diol according to claim 1 and a polyisocyanate to obtain a prepolymer; and
reacting the prepolymer with a chain extender.

15. A method, comprising:
mixing the polycarbonate diol according to claim 1, a polyisocyanate, and a chain extender together at once; and
reacting the obtained mixture.

16. The polycarbonate diol according to claim 1, wherein 95% or more of molecular chain terminals of the polycarbonate diol are hydroxyl groups.

17. The method according to claim 6, wherein 95% or more of molecular chain terminals of the obtained polycarbonate diol are hydroxyl groups.

18. The polycarbonate diol according to claim 1, wherein the highest temperature during the reaction of (i), (ii), and (iii) is less than 180° C., wherein the number average molecular weight of the polycarbonate diol is 250 to 900, and wherein the molecular weight distribution (Mw/Mn) of the polycarbonate diol is 1.5 to 3.5.

* * * * *